(12) United States Patent
Donato et al.

(10) Patent No.: US 8,809,377 B2
(45) Date of Patent: Aug. 19, 2014

(54) DEUBIQUITINASE INHIBITORS AND METHODS FOR USE OF THE SAME

(75) Inventors: Nicholas J. Donato, Ann Arbor, MI (US); Christiane Wobus, Dexter, MI (US); Hollis D. Showalter, Ann Arbor, MI (US); Moshe Talpaz, Ann Arbor, MI (US); Jeffrey W. Perry, Ypsilanti, MI (US); Roderick J. Sorenson, Ann Arbor, MI (US); Mary X. O'Riordan, Ann Arbor, MI (US); Yafei Jin, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 12 days.

(21) Appl. No.: 13/241,802

(22) Filed: Sep. 23, 2011

(65) Prior Publication Data

US 2012/0077806 A1    Mar. 29, 2012

Related U.S. Application Data

(60) Provisional application No. 61/386,057, filed on Sep. 24, 2010.

(51) Int. Cl.
*A61K 31/444* (2006.01)
*A61K 31/4433* (2006.01)
*A61K 31/4436* (2006.01)
*A61K 31/4439* (2006.01)

(52) U.S. Cl.
USPC ........ 514/340; 514/342; 514/343; 546/268.1; 546/276.4; 546/345

(58) Field of Classification Search
CPC .. C07D 213/57; C07D 401/12; C07D 413/12; C07D 417/12
USPC ................... 546/268.1, 276.4, 345
See application file for complete search history.

(56) References Cited

U.S. PATENT DOCUMENTS

| 2005/0277680 A1 | 12/2005 | Priebe et al. |
| 2007/0232668 A1 | 10/2007 | Priebe et al. |
| 2010/0152143 A1 | 6/2010 | Priebe et al. |

FOREIGN PATENT DOCUMENTS

| WO | WO-2005/058829 A1 | 6/2005 |
| WO | WO-2008/005954 A2 | 1/2008 |

OTHER PUBLICATIONS

Bartholomeusz et al., Activation of a novel Bcr/Abl destruction pathway by WP1130 induces apoptosis of chronic myelogenous leukemia cells, Blood, 109(8):3470-8 (2007).
Bryk et al., Selective killing of nonreplicating mycobacteria, Cell Host Microbe, 3(3): 137-45 (2008).
Bryk et al., Triazaspirodimethoxybenzoyls as selective inhibitors of mycobacterial lipoamide dehydrogenase, Biochemistry, 49(8):1616-27 (2010).
Casenghi et al., New approaches to filling the gap in tuberculosis drug discovery, New approaches to filling the gap in tuberculosis drug discovery, PLoS Med., 4(11): e293 (2007).
Darby et al., Killing of non-replicating *Mycobacterium tuberculosis* by 8-hydroxyquinoline, J. Antimicrob. Chemother., 65(7):1424-7 (2010).
De Carvalho et al., Nitazoxanide kills replicating and nonreplicating *Mycobacterium tuberculosis* and evades resistance, J. Med. Chem., 52(19):5789-92 (2009).
Edelmann et al., Ubiquitin and ubiquitin-like specific proteases targeted by infectious pathogens: emerging patterns and molecular principles, Biochim. Biophys. Acta, 1782:809-16 (2008).
Hu et al., Structure of the *Mycobacterium tuberculosis* proteasome and mechanism of inhibition by a peptidyl boronate, Mol. Microbiol., 59(5):1417-28 (2006).
Kapuria et al., A novel small molecule deubiquitinase inhibitor blocks Jak2 signaling through Jak2 ubiquitination, Cell Signal., 23(12):2076-85 (2011).
Kapuria et al., Deubiquitinase inhibition by small-molecule WP1130 triggers aggresome formation and tumor cell apoptosis, Cancer Res., 70(22):9265-76 (2010).
Kapuria et al., Protein cross-linking as a novel mechanism of action of a ubiquitin-activating enzyme inhibitor with anti-tumor activity, Biochem. Pharmacol., 82(4):341-9 (2011).
Kline et al., Substituted 2-imino-5-arylidenethiazolidin-4-one inhibitors of bacterial type III secretion, J. Med. Chem., 51(22):7065-74 (2008).
Lin et al., Fellutamide B is a potent inhibitor of the *Mycobacterium tuberculosis* proteasome, Arch. Biochem. Biophys., 501(2):214-20 (2010).
Lin et al., Inhibitors selective for mycobacterial versus human proteasomes, Nature, 461(7264):621-6 (2009).
Lindner, Dubiquitination in virus infection, Virology, 362:245-56 (2007).
Love et al., Mechanism, biology and inhibitors of dubiquitinating enzymes, Nat. Chem. Biol., 3(11):697-705 (2007).

(Continued)

*Primary Examiner* — Brian McDowell
(74) *Attorney, Agent, or Firm* — Marshall, Gerstein & Borun LLP

(57) ABSTRACT

Disclosed herein are methods of inhibiting a deubiquitinase (DUB), methods of treating pathogenic infections (e.g., viral, bacterial, and/or parasitic), methods of inhibiting cell proliferation, methods of treating a neurodegenerative disease, methods of treating one or more symptoms of a neurodegenerative disease or a genetic disorder, and compounds, wherein the compound can have a structure of formula (III):

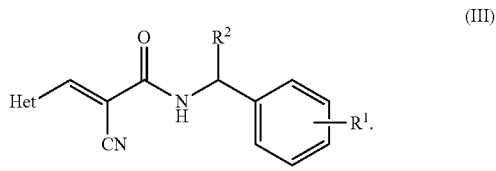

(III)

22 Claims, No Drawings

(56) References Cited

OTHER PUBLICATIONS

Mullally et al., Pharmacophore model for novel inhibitors of ubiquitin isopeptidases that induce p53-independent cell death, Molecular Pharmacol., 62(2):351-8 (2002).

Nathan et al., Tuberculosis, 88 Suppl 1: S25-33 (2008).

Rolfe et al., the ubiquitin-mediated proteolytic pathway as a therapeutic area, J. Mol. Med., 75:5-17 (1997).

Schwickart et al., Deubiquitinase USP9X stabilizes MCL1 and promotes tumour cell survival, Nature, 463(7277):103-7 (2010).

Sun et al., Bcr-Abl ubiquitination and Usp9x inhibition block kinase signaling and promote CML cell apoptosis, Blood, 117(11):3151-62 (2011).

Verstovsek et al., WP1066, a novel JAK2 inhibitor, suppresses proliferation and induces apoptosis in erythroid human cells carrying the JAK2 V617F mutation. Clin. Cancer Res., 14(3):788-96 (2008).

Bartholomeusz et al., Degrasyn activates proteasomal-dependent degradation of c-Myc, Cancer Res., 67(8):3912-8 (2007).

DEUBIQUITINASE INHIBITORS AND METHODS FOR USE OF THE SAME

CROSS REFERENCE TO RELATED APPLICATIONS

This application claims the benefit of U.S. provisional application Ser. No. 61/386,057, filed Sep. 24, 2010, the disclosure of which is incorporated by reference in its entirety.

BACKGROUND

Ubiquitination is a covalent post-translational modification of cellular proteins involving a complex enzymatic cascade. Emerging evidence suggests that many enzymes of the ubiquitination cascade are differentially expressed or activated in several diseases, and may therefore be appropriate therapeutic targets.

Protein ubiquitination is a dynamic two-way process that can be reversed or regulated by deubiquitinating (deubiquitinase, DUB) enzymes. The human genome codes for nearly 100 proteins with putative DUB activity which can be broadly divided into two main sub-groups: ubiquitin C-terminal hydrolase (UCH) and the ubiquitin-specific proteases (USP). USPs comprise the largest subclass of DUBs in humans, while only 4 known UCH DUBs have been described. DUBs primarily serve to counterbalance ubiquitin-protein conjugation and also facilitate the cleavage of ubiquitin from its precursors and unanchored polyubiquitin chains. Thus, DUBs regulate and maintain the homeostasis of free ubiquitin pools in the cell. Several DUBs have been reported to regulate deubiquitination of histones, DNA damage repair, cellular proliferation (USP2) and cytokine signaling (DUB-A). DUBs such as USP14, Uch37 and RPN11 have been shown to associate with the regulatory sub-unit of the proteasome (19S) and edit polyubiquitin chains on proteasome substrates.

SUMMARY

Disclosed herein are methods of inhibiting DUBs. Methods are additionally or alternatively directed to inhibiting a UCH catalytic domain. Further disclosed herein are methods of treating a pathogenic infection and methods of treating a condition due to a pathogenic infection. Also disclosed herein are methods of inhibiting proliferation or decreasing survival of a cell. Further disclosed herein are methods of treating a neurodegenerative disorder or symptoms of a neurodegenerative disorder. Also disclosed herein are methods of treating symptoms of a genetic disorder.

Compounds useful in the disclosed methods include compound having a formula:

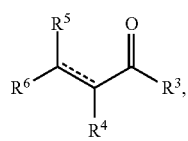

(I)

wherein the dashed line indicates an optional double bond; $R^3$ is aminoalkylenearyl or substituted aminoalkylenearyl; $R^4$ is selected from the group consisting of CN, amino, substituted amino, amido, substituted amido, alkylenethioether, substituted alkylenethioether, alkyl, substituted alkyl, azide, alkyleneazide, or substituted alkyleneazide; $R^5$ is selected from the group consisting of hydrogen, alkyl, substituted alkyl, alkenyl, substituted alkenyl, alkynyl, substituted alkynyl, alkoxy, substituted alkoxy, alkylenearyl, substituted alkylenearyl, thioether, substituted thioether, amino, substituted amino, halide, hydroxy, nitro, and SH; and $R^6$ is selected from the group consisting of aryl, substituted aryl, heteroaryl, substituted heteroaryl, heterocycloalkenyl, substituted heterocycloalkenyl, heterocycloalkyl, substituted heterocycloalkyl, alkylenearyl, substituted alkylenearyl, alkyleneheteroaryl, substituted alkyleneheteroaryl, alkylenheterocycloalkenyl, substituted alkyleneheterocycloalkenyl, alkyleneheterocycloalkyl, and substituted alkyleneheterocycloalkyl, or a salt thereof.

In various cases, the compounds useful in the disclosed methods include compounds having a formula (II), (IIa), or (III):

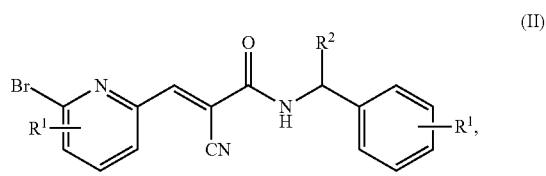

(II)

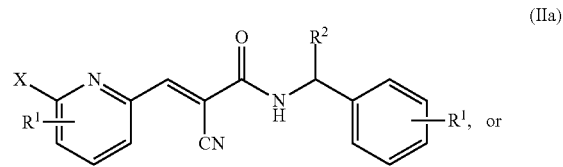

(IIa)

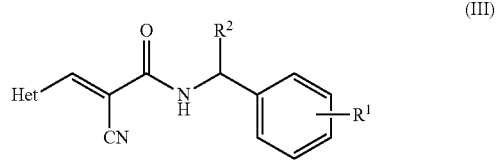

(III)

wherein each $R^1$ is selected from the group consisting of H, amido, substituted amido, halide, $(CH_2)_m R^9$, $-NH(CH_2)_m R^9$, $-NHC(O)(CH_2)_m R^9$, $-C(O)NH(CH_2)_m R^9$ and $-O(CH_2)_m R^9$ and cannot each be hydrogen for the compound of formula (II); X is fluoro or chloro; $R^2$ is alkyl, substituted alkyl, cycloalkyl, substituted cycloalkyl, aryl, substituted aryl, heteroaryl, or substituted heteroaryl, Het is heteroaryl or substituted heteroaryl excluding 2-pyridyl; $R^9$ is amino, substituted amino, hydroxy, alkoxy, substituted alkoxy, cycloheteroalkyl, or substituted cycloheteroalkyl; and m is 2, 3, or 4, or salt thereof. Any specific compound described below can be used in one or more of the described methods.

Further disclosed herein a compounds having a formula (II), (IIa), or (III)

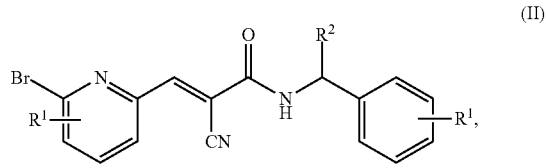

(II)

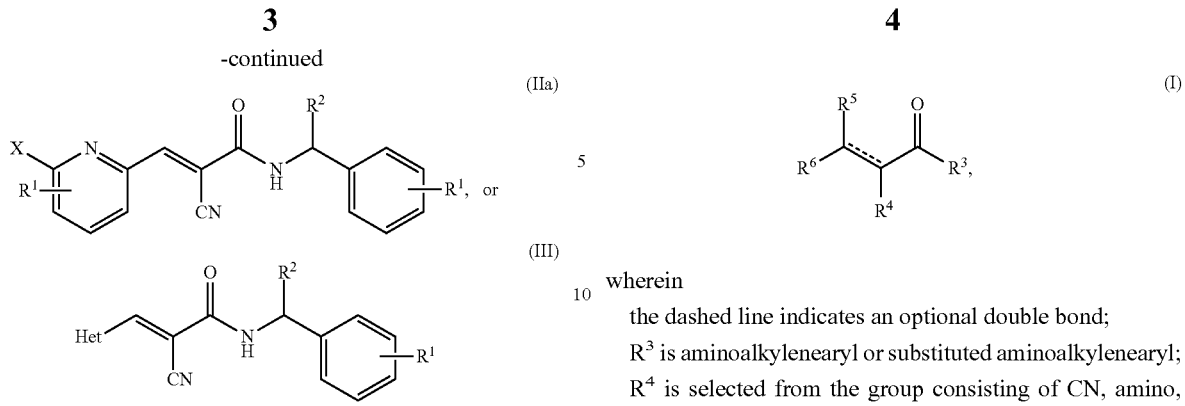

wherein each $R^1$ is selected from the group consisting of H, amido, substituted amido, halide, $(CH_2)_m R^9$, —NH$(CH_2)_m R^9$, —NHC(O)$(CH_2)_m R^9$, —C(O)NH$(CH_2)_m R^9$ and —O$(CH_2)_m R^9$ and cannot each be hydrogen for the compound of formula (II); X is fluoro or chloro; $R^2$ is alkyl, substituted alkyl, cycloalkyl, substituted cycloalkyl, aryl, substituted aryl, heteroaryl, or substituted heteroaryl, Het is heteroaryl or substituted heteroaryl excluding 2-pyridyl; $R^9$ is amino, substituted amino, hydroxy, alkoxy, substituted alkoxy, cycloheteroalkyl, or substituted cycloheteroalkyl; and m is 2, 3, or 4, or salt thereof.

DETAILED DESCRIPTION

Protein ubiquitination is a precisely controlled process that requires the participation of several enzymes that modify lysine residues on target proteins with monomeric or polymeric chains of ubiquitin (Ub). The ubiquitin pathway enzymes are mediators of eukaryotic cell cycle timing, protein destruction and signal transduction. Recent studies suggest that Ub regulation is also critical at various stages of the prokaryotic and viral life cycle and within the eukaryotic host cells as well. Therefore disruption or inhibition of specific Ub regulatory enzymes may have anti-microbial activity.

Owing to the diverse role of DUBs in the regulation of proteins involved in transformation, cell cycle regulation, apoptotic protection and drug resistance, DUBs appear to represent appropriate therapeutic targets. Recently, down regulation of USP2 and USP9x were shown to inhibit tumor cell growth by promoting cyclin D1 and MCL-1 degradation, respectively suggesting silencing of specific DUBs in tumor cells may be a safe and effective therapy in oncogene-addicted or drug-resistant cells. Other studies firmly establish a role for DUBs in a broad spectrum of diseases including cancer, viral and bacterial pathogenesis as well as neurodegenerative disorders. Although few compounds have been described with DUB modulatory activity, most report anti-tumor, anti-proliferative or anti-viral activity associated with DUB inhibition (e.g., UCH-L1 and USP7, SARS protease).

Thus, disclosed herein are methods of inhibiting a DUB, methods of inhibiting a UCH catalytic domain, methods of inhibiting or preventing a pathogenic infection, methods of inhibiting survival or proliferation of a cell, methods of treating a neurodegenerative disorder, methods of treating one or more symptoms of a neurodegenerative disorder, methods of treating one or more symptoms of a genetic disorder, and compounds that can inhibit a DUB. In methods provided, the DUB is contacted with a compound, e.g., of formula (I) or salt thereof wherein the dashed line indicates an optional double bond;

$R^3$ is aminoalkylenearyl or substituted aminoalkylenearyl;

$R^4$ is selected from the group consisting of CN, amino, substituted amino, amido, substituted amido, alkylenethioether, substituted alkylenethioether, alkyl, substituted alkyl, azide, alkyleneazide, or substituted alkyleneazide;

$R^5$ is selected from the group consisting of hydrogen, alkyl, substituted alkyl, alkenyl, substituted alkenyl, alkynyl, substituted alkynyl, alkoxy, substituted alkoxy, alkylenearyl, substituted alkylenearyl, thioether, substituted thioether, amino, substituted amino, halide, hydroxy, nitro, and SH; and $R^6$ is selected from the group consisting of aryl, substituted aryl, heteroaryl, substituted heteroaryl, heterocycloalkenyl, substituted heterocycloalkenyl, heterocycloalkyl, substituted heterocycloalkyl, alkylenearyl, substituted alkylenearyl, alkyleneheteroaryl, substituted alkyleneheteroaryl, alkyleneheterocycloalkenyl, substituted alkyleneheterocycloalkenyl, alkyleneheterocycloalkyl, and substituted alkyleneheterocycloalkyl.

Deubiquitinases (DUBs)

Deubiquitinating enzymes (i.e., deubiquitinases or DUBs) are typically a cysteine protease and may be classified into subgroups as ubiquitin-specific proteases (USP) and ubiquitin C-terminal hydrolases (UCH). Examples of DUBs include, for instance, USP5, USP6, USP4, USP8, USP13, USP2, USP11, USP14, USP7, USP9X, USP10, USP1, USP12, USP16, USP15, USP17, USP19, USP20, USP3, USP9Y, USP18, USP21, USP22, USP33, USP29, USP25, USP36, USP32, USP26, USP24, USP42, USP46, USP37, USP28, USP47, USP38, USP44, USP50, USP35, USP30, Mername-AA088peptidase, Mername-AA091 peptidase, USP45, USP51, USP34, USP48, USP40, USP31, Mername-AA129peptidase, USP49, USP17-like peptidase, USP54, USP53, USP39, UCH-L1, UCH-L3, UCH-BAP1, UCH37, Cezanne deubiquitinating peptidase, Cezanne2, tumor necrosis factor alpha-induced protein 3, TRABID protein, VCP (p97)/p47-interacting protein, otubain1, otubain2, CylD protein, SENP1 peptidase, SENP3 peptidase, SENP6 peptidase, SENP2 peptidase, SENP5peptidase, SENP7peptidase, SENP8peptidase, SENP4peptidase, Poh1 peptidase, Jab1/MPN domain metalloenzyme, Mername-AA 165 peptidase, Mername-AA 166 peptidase, Mername-AA 167 peptidase, Mername-AA168 protein, COP9 signalosome subunit6, 26S proteasome non-ATPase regulatory subunit7, eukaryotic translation initiation factor3 subunit5, IFP38 peptidase homologue.

Other DUBs contemplated include autophagin (ATG), ovarian tumor (OTU) domain proteins, Josephin-domain (JD) or Machado-Joseph disease (MJD) proteins, ubiquitin-like protein-specific protease (ULP), and JAMM (Jab1/MPN domain-associated metalloisopeptidase) domain proteins.

Specific DUB Inhibitors

Compounds that are used in methods disclosed herein include compounds, or salts thereof, of formula (I)

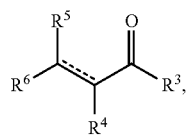

wherein
the dashed line indicates an optional double bond;
$R^3$ is aminoalkylenearyl or substituted aminoalkylenearyl;
$R^4$ is selected from the group consisting of CN, amino, substituted amino, amido, substituted amido, alkylenethioether, substituted alkylenethioether, alkyl, substituted alkyl, azide, alkyleneazide, or substituted alkyleneazide;
$R^5$ is selected from the group consisting of hydrogen, alkyl, substituted alkyl, alkenyl, substituted alkenyl, alkynyl, substituted alkynyl, alkoxy, substituted alkoxy, alkylenearyl, substituted alkylenearyl, thioether, substituted thioether, amino, substituted amino, halide, hydroxy, nitro, and SH; and
$R^6$ is selected from the group consisting of aryl, substituted aryl, heteroaryl, substituted heteroaryl, heterocycloalkenyl, substituted heterocycloalkenyl, heterocycloalkyl, substituted heterocycloalkyl, alkylenearyl, substituted alkylenearyl, alkyleneheteroaryl, substituted alkyleneheteroaryl, alkyleneheterocycloalkenyl, substituted alkyleneheterocycloalkenyl, alkyleneheterocycloalkyl, and substituted alkyleneheterocycloalkyl.

In some cases, the dashed line indicates a double bond. In various cases, specific $R^3$ moieties contemplated include $R^3$ is selected from the group consisting of

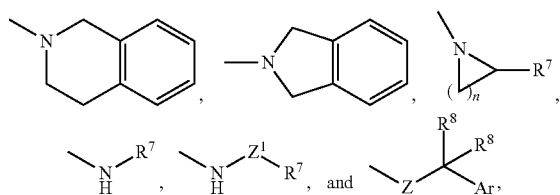

or an optionally substituted moiety thereof; $R^7$ is selected from the group consisting of 2-pyridyl, 3-pyridyl, 4-pyridyl, a monosaccharide, a monosaccharide derivative, aryl, and alkylenearyl, or an optionally substituted moiety thereof; each $R^8$ is independently selected from the group consisting of hydrogen, alkyl, substituted alkyl, cycloalkyl, substituted cycloalkyl, aryl and substituted aryl; Ar is aryl or substituted aryl; Z is alkylene, substituted alkylene, amino, or substituted amino; $Z^1$ is alkylene or substituted alkylene; and n is 1, 2, 3, or 4. In some cases, specific $R^6$ moieties contemplated include 2-pyridyl, 3-pyridyl, 4-pyridyl, phenyl, 1-piperdinyl, 2-(2H)-pyranyl, and 2-(2H)-thiopyranyl, or a substituted moiety thereof. In some specific cases, $R^6$ is 2-pyridyl or substituted 2-pyridyl. In various specific cases, $R^4$ is CN.

In some cases, $R^3$ is

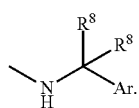

In some specific cases, Ar is phenyl or substituted phenyl.

Some specific compounds contemplated include the following structures,

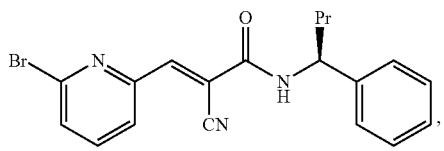

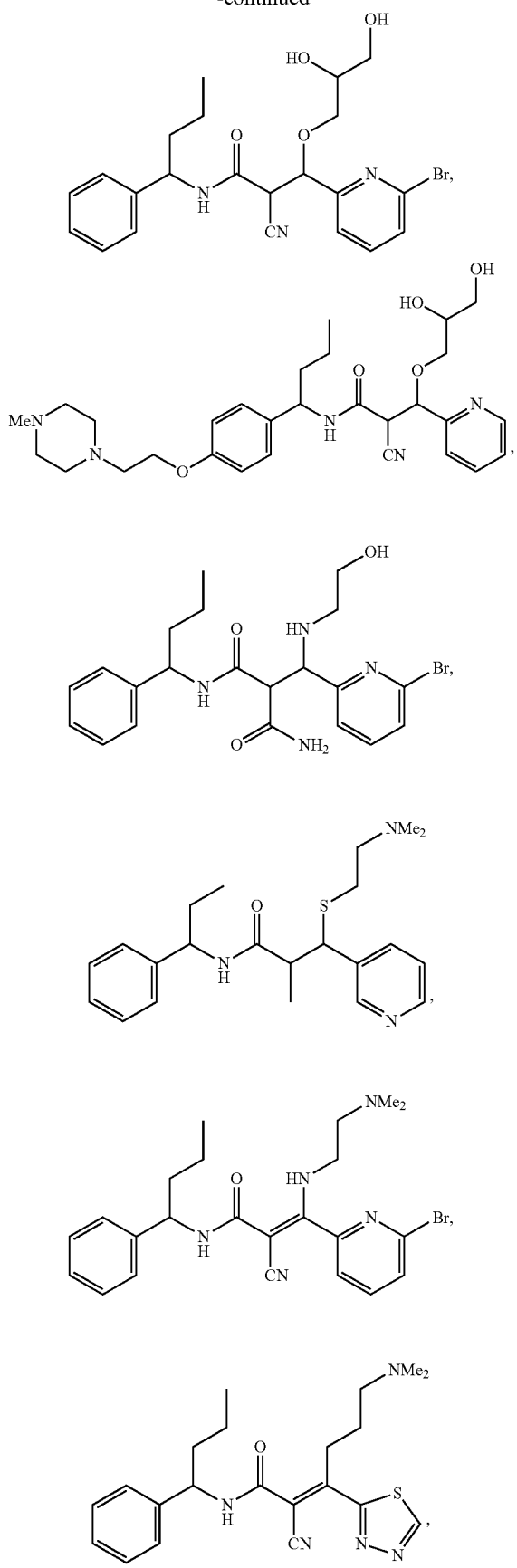
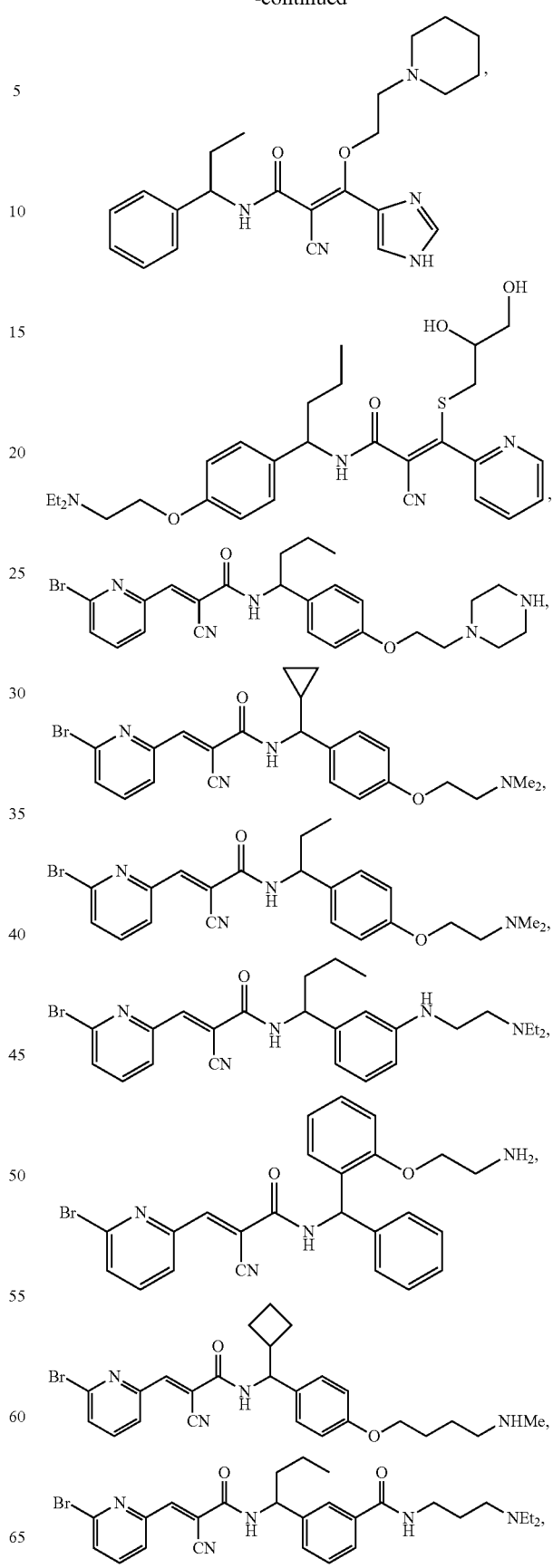

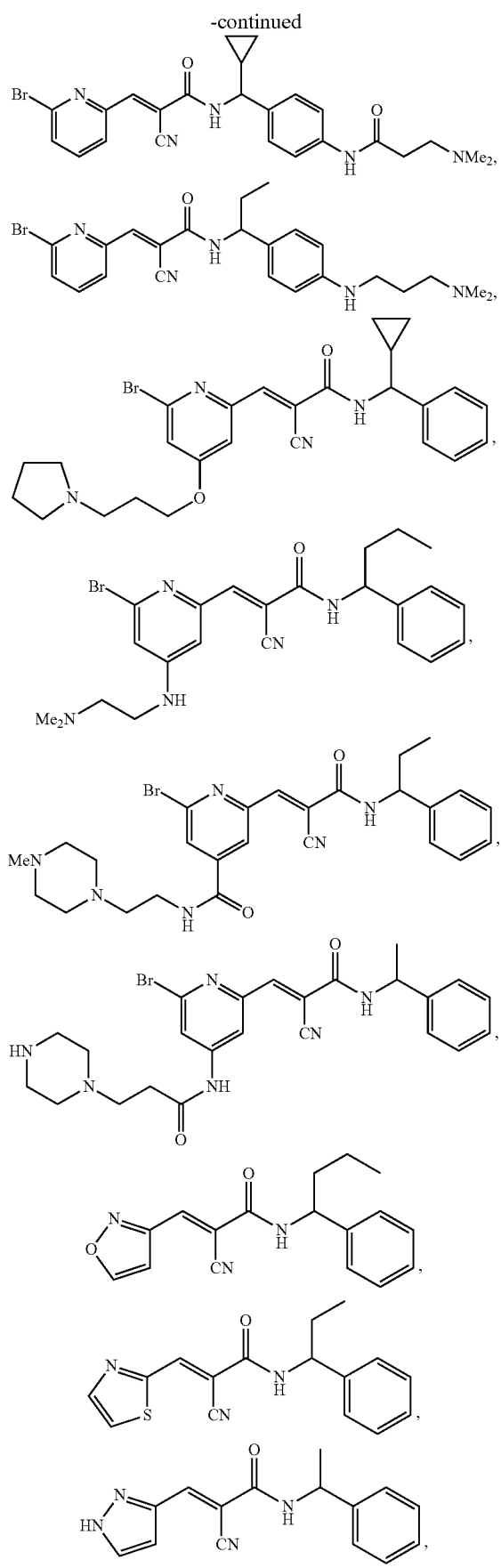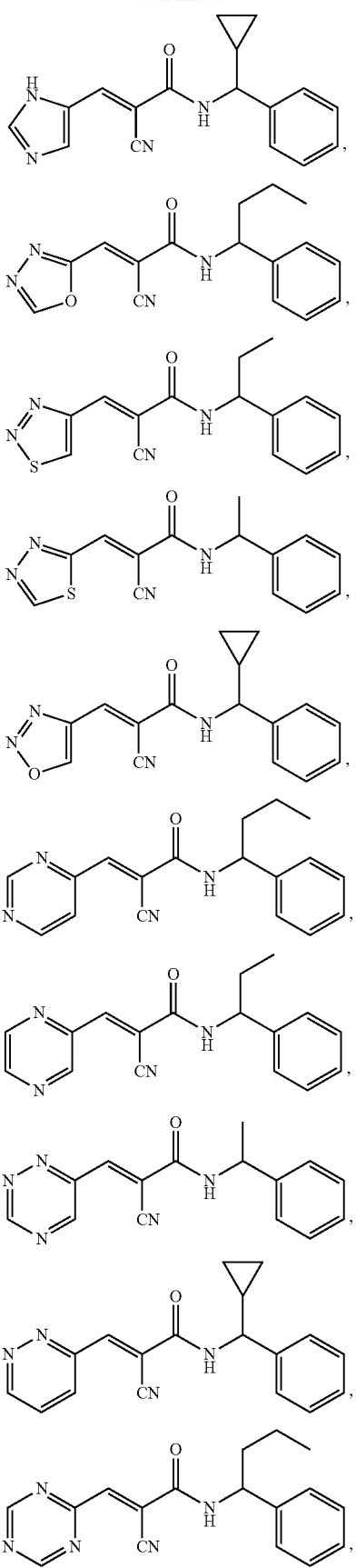

-continued
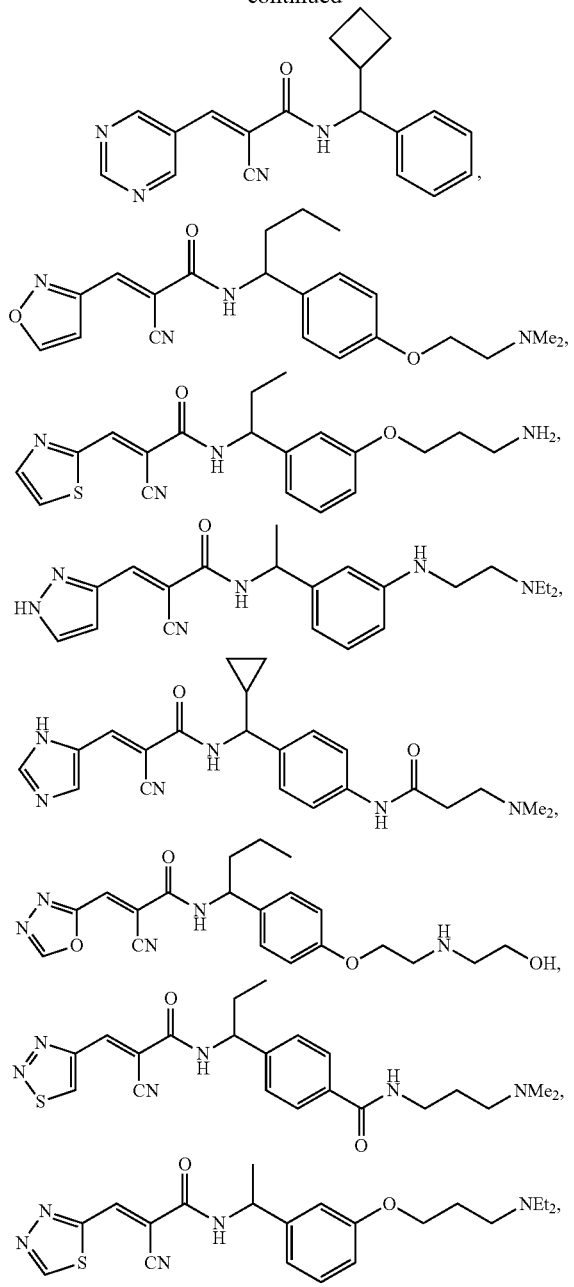
-continued
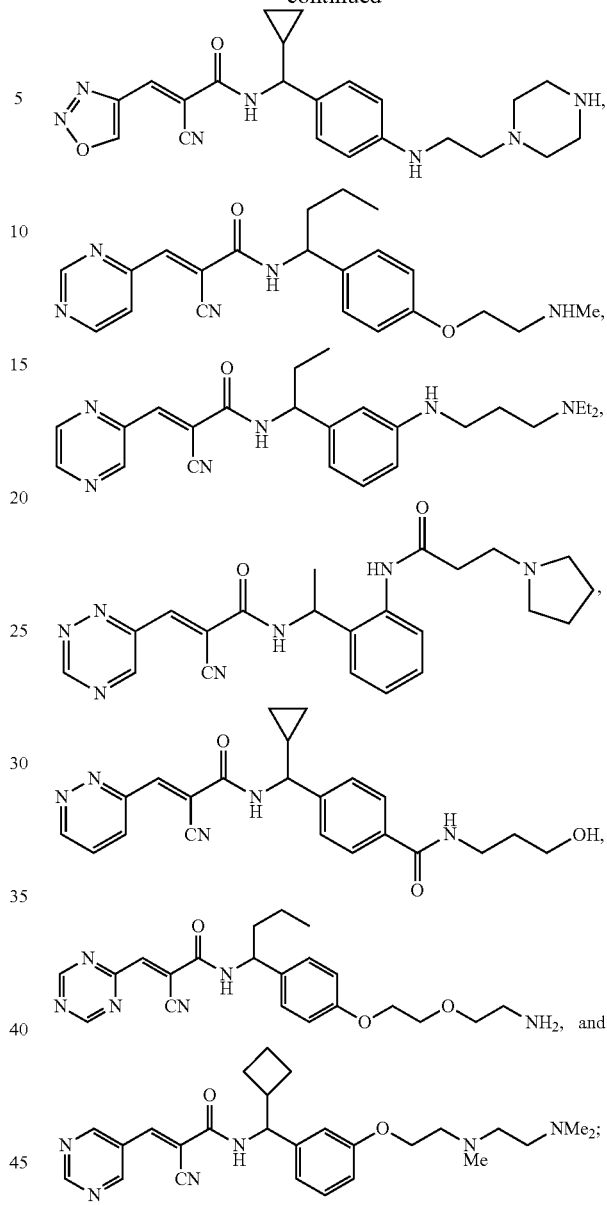
or salt thereof.
Further contemplated inhibitors include
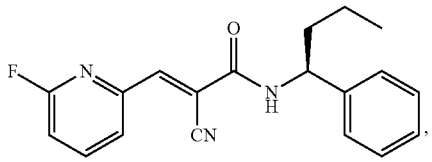 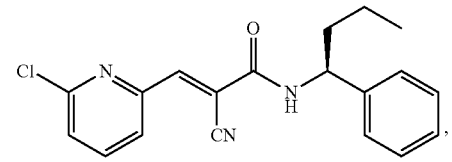
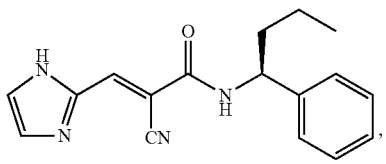 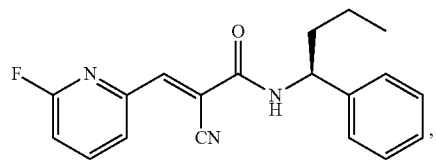

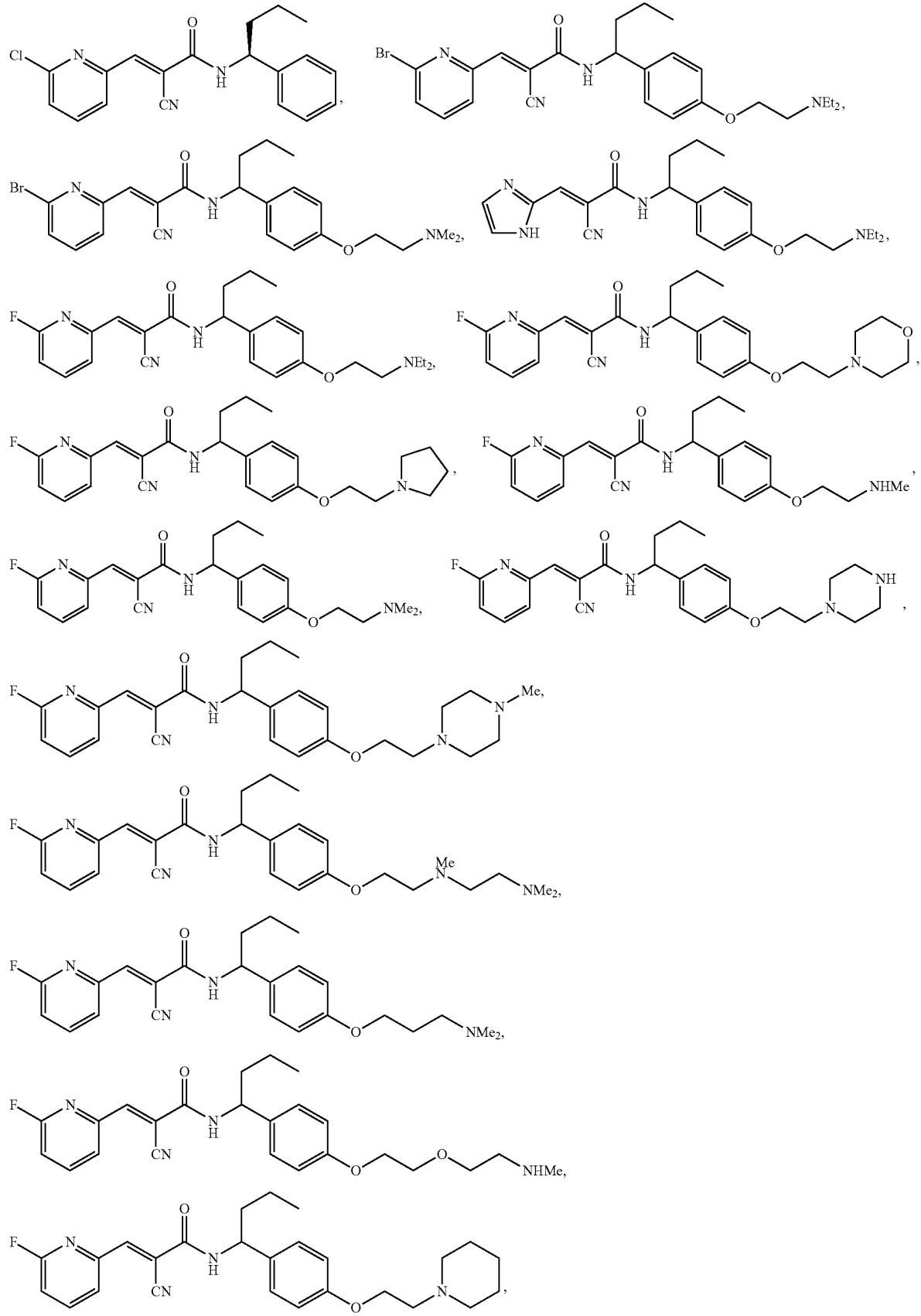

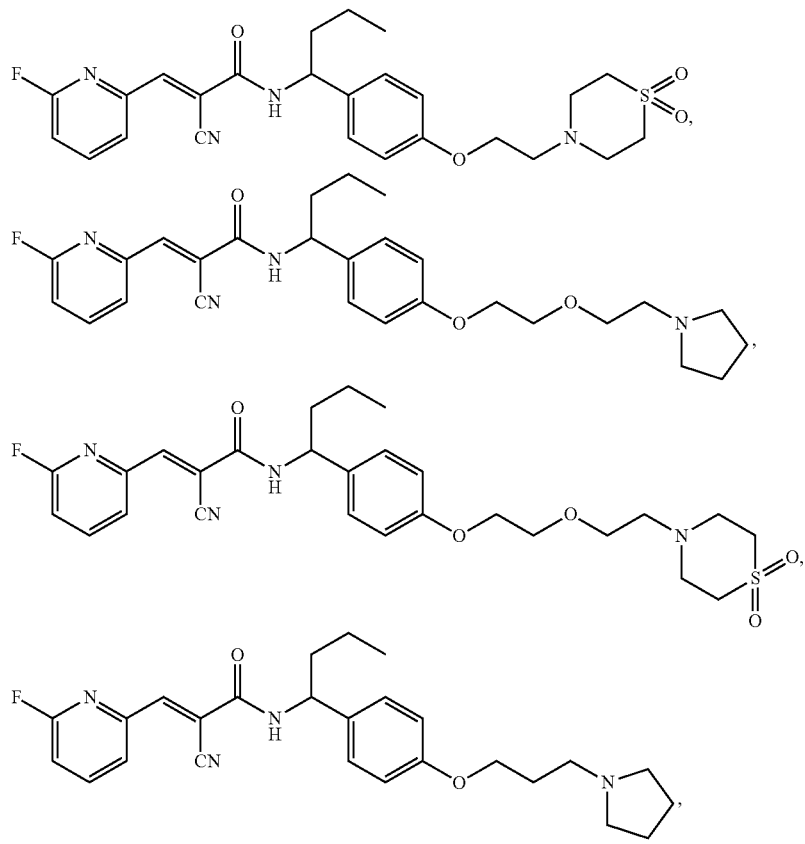
or a salt thereof. Further contemplated are inhibitors having a structure of
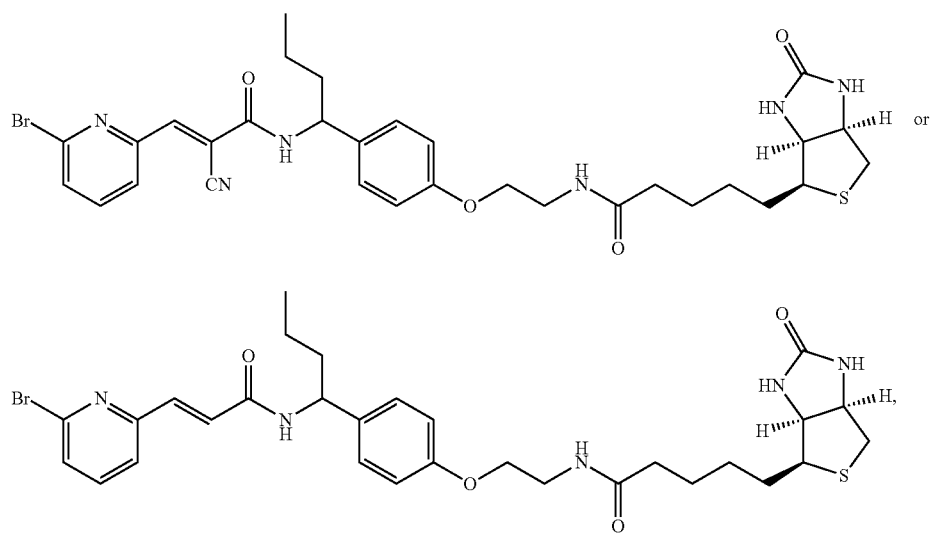
or a salt thereof.
In some embodiments, the compound of formula (I) is a compound of formula (II), (IIa), or (III), or salt thereof:

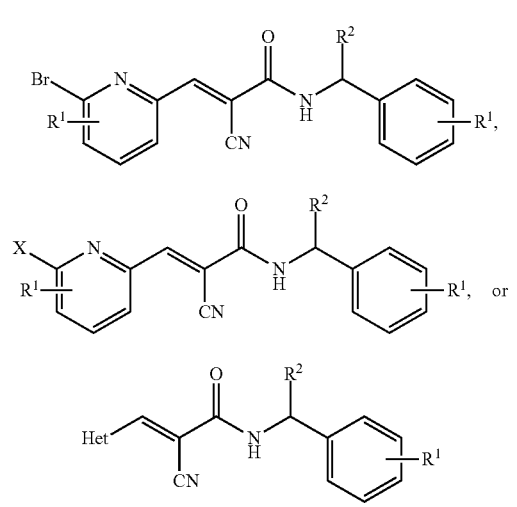

(II)

(IIa)

(III)

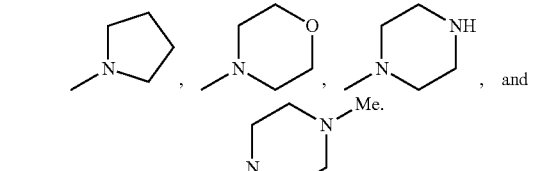

, and

In some cases, the compound of formula (II) or (III) specifically excludes compounds having a structure

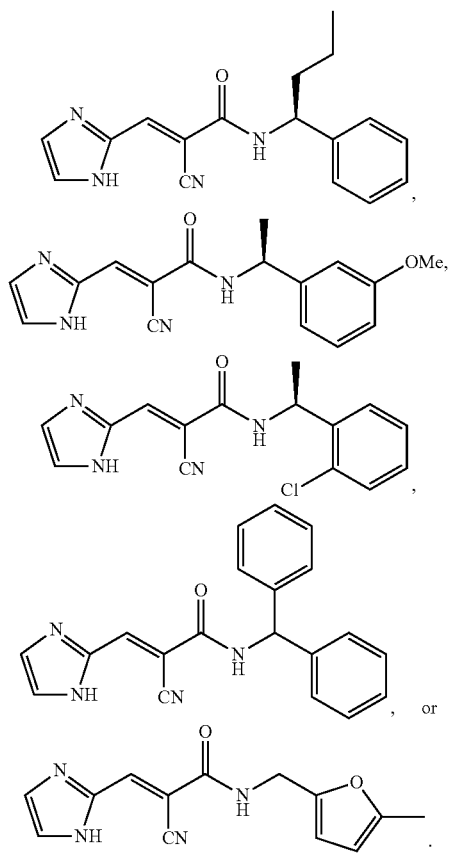

wherein each $R^1$ is selected from the group consisting of H, amido, substituted amido, halide, $(CH_2)_m R^9$, —NH $(CH_2)_m R^9$, —NHC(O)$(CH_2)_m R^9$, —C(O)NH$(CH_2)_m R^9$ and —O$(CH_2)_m R^9$ and cannot each be hydrogen for the compound of formula (II); X is fluoro or chloro; $R^2$ is alkyl, substituted alkyl, cycloalkyl, substituted cycloalkyl, aryl, substituted aryl, heteroaryl, or substituted heteroaryl, Het is heteroaryl or substituted heteroaryl excluding 2-pyridyl; $R^9$ is amino, substituted amino, hydroxy, alkoxy, substituted alkoxy, cycloheteroalkyl, or substituted cycloheteroalkyl; and m is 2, 3, or 4, or salt thereof. In various cases, $R^1$ is selected from the group consisting of H, —$(CH_2)_m R^9$, —NH $(CH_2)_m R^9$, —NHC(O)$(CH_2)_m R^9$, —C(O)NH$(CH_2)_m R^9$ and —O$(CH_2)_m R^9$. In various cases, $R^1$ is selected from the group consisting of —O$(CH_2)_m NEt_2$; —O$(CH_2)_m NMe_2$; —O$(CH_2)_m NHEt$; —O$(CH_2)_m NHMe_2$;

—O$(CH_2)_m$morpholinyl; —O$(CH_2)_m$ substituted morpholinyl; —O$(CH_2)_m$sulfoxymorpholinyl; —O$(CH_2)_m$substituted sulfoxymorpholinyl; —O$(CH_2)_m$pyrrolidinyl; —O$(CH_2)_m$ substituted pyrrolidinyl; —O$(CH_2)_m$piperazinyl; —O$(CH_2)_m$substituted piperazinyl; —O$(CH_2)_m$piperidinyl; —O$(CH_2)_m$substituted piperidinyl; —O$(CH_2)_m$N(Me) $(CH_2)_2 NMe_2$; —O$(CH_2)_m$N(Me)$(CH_2)_2$NHMe; —O $(CH_2)_m$N(Me)$(CH_2)_2$NEt$_2$; —O$(CH_2)_m$N(Me)$(CH_2)_2$NHEt; —O$(CH_2)_m$O$(CH_2)_2$NMe; —O$(CH_2)_m$O$(CH_2)_2$NHMe; —O$(CH_2)_m$O$(CH_2)_2$NEt$_2$; —O$(CH_2)_m$O$(CH_2)_2$NHEt, —O$(CH_2)_m$O$(CH_2)_2$heterocycloalkyl; and —O$(CH_2)_m$O $(CH_2)_2$substituted heterocycloalkyl. In various cases, $R^1$ is —O$(CH_2)_m$NH(CO)alkylene-biotin. In various cases, the compound is a compound of formula (II) or (III).

In some cases, $R^2$ is $C_{1-6}$ alkyl or $C_{3-6}$ cycloalkyl, and is optionally substituted with one or more of hydroxy, amino, substituted amino, alkoxy, and substituted alkoxy. In certain cases, $R^1$ of the compound of formula (II) or (IIa) is selected from the group consisting of H—$(CH_2)_m R^9$, —NH $(CH_2)_m R^9$, —NHC(O)$(CH_2)_m R^9$, —C(O)NH$(CH_2)_m R^9$ and —O$(CH_2)_m R^9$ and —O$(CH_2)_m R^9$. In various cases, $R^1$ is selected from the group consisting of H, amide, substituted amide, and halide. In some embodiments, $R^9$ is selected from the group consisting of OH, $NH_2$, NHMe, $N(Me)_2$, $N(Et)_2$, O$(CH_2)_2 NH_2$, NH$(CH_2)_2$OH, N(Me)$(CH_2)_2 N(Me_2)$, forty carbon atoms, including, but not limited to, methyl, ethyl, n-propyl, isopropyl, n-butyl, isobutyl, tert-butyl, n-hexyl, and the like. Alkyls of one to six carbon atoms are also contemplated. The term "alkyl" includes "bridged alkyl," i.e., a bicyclic or polycyclic hydrocarbon group, for example, norbornyl, adamantyl, bicyclo[2.2.2]octyl, bicyclo[2.2.1] heptyl, bicyclo[3.2.1]octyl, or decahydronaphthyl. Alkyl groups optionally can be substituted, for example, with hydroxy (OH), halide, thiol (SH), aryl, heteroaryl, cycloalkyl, heterocycloalkyl, and amino. It is specifically contemplated that in the compounds described herein the alkyl group consists of 1-40 carbon atoms, preferably 1-25 carbon atoms, preferably 1-15 carbon atoms, preferably 1-12 carbon atoms, preferably 1-10 carbon atoms, preferably 1-8 carbon atoms, and preferably 1-6 carbon atoms. "Heteroalkyl" is defined similarly as alkyl, except the heteroalkyl contains at least one heteroatom independently selected from the group consisting of oxygen, nitrogen, and sulfur.

As used herein, the term "cycloalkyl" refers to a cyclic hydrocarbon group, e.g., cyclopropyl, cyclobutyl, cyclohexyl, and cyclopentyl. "Heterocycloalkyl" is defined similarly as cycloalkyl, except the ring contains one to three heteroatoms independently selected from the group consisting of oxygen, nitrogen, and sulfur. Nonlimiting examples of heterocycloalkyl groups include piperdine, tetrahydrofuran, tetrahydropyran, dihydrofuran, morpholine, thiophene, and the like. Cycloalkyl and heterocycloalkyl groups can be saturated or partially unsaturated ring systems optionally substituted with, for example, one to three groups, independently selected from the group consisting of alkyl, alkyleneOH, C(O)NH$_2$, NH$_2$, oxo (=O), aryl, haloalkyl, halo, and OH. Heterocycloalkyl groups optionally can be further N-substituted with alkyl, hydroxyalkyl, alkylenearyl, or alkyleneheteroaryl.

The term "alkenyl" used herein refers to a straight or branched chain hydrocarbon group of two to ten carbon atoms containing at least one carbon double bond including, but not limited to, 1-propenyl, 2-propenyl, 2-methyl-1-propenyl, 1-butenyl, 2-butenyl, and the like. The term "cycloalkenyl" refers to a cycloalkyl group having one or more double bonds. "Heterocycloalkenyl" refers to a cycloalkenyl group having one or more heteroatoms (e.g., N, S, O, or combinations thereof).

The term "alkynyl" used herein refers to a straight or branched chain hydrocarbon group of two to ten carbon atoms containing at least one carbon triple bond including, but not limited to, 1-propynyl, 2-propynyl, 1-butynyl, 2-butynyl, and the like.

The term "halide" used herein refers to fluoro, chloro, bromo, or iodo.

The term "alkylene" used herein refers to an alkyl group having a substituent. For example, the term "alkylene aryl" refers to an alkyl group substituted with an aryl group. The alkylene group is optionally substituted with one or more substituent previously listed as an optional alkyl substituent. For example, an alkylene group can be —CH$_2$CH$_2$— or —CH$_2$—.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, OCF$_3$, NO$_2$, CN, NC, OH, alkoxy, amino, CO$_2$H, CO$_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, OCF$_3$, NO$_2$, CN, NC, OH, alkoxy, amino, CO$_2$H, CO$_2$alkyl, aryl, and heteroaryl. In some cases, the heteroaryl group is substituted with one or more of alkyl and alkoxy groups. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl. As used herein, heteroaryl is interchangeably used with the term "Het." In some cases, "Het" is selected from the group consisting of

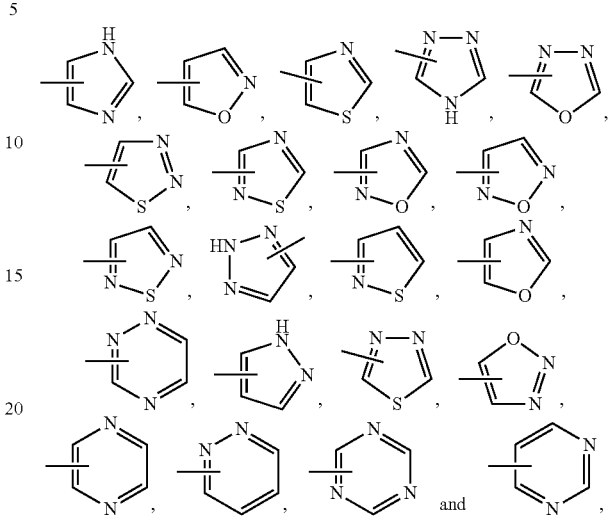

or a substituted moiety thereof. In some cases, Het excludes 2-pyridyl, 3-pyridyl, and/or 4-pyridyl. In certain cases, Het is substituted with one or more of alkyl, alkoxy, hydroxy, amino, and substituted amino.

The term "alkoxy" used herein refers to straight or branched chain alkyl group covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "thioalkyl" used herein refers to one or more thio groups appended to an alkyl group.

The term "thioether" used herein refers to straight or branched chain alkyl or cycloalkyl group covalently bonded to the parent molecule through an —S— linkage. Examples of thioether groups include, but are not limited to, —SCH$_3$, —SCH$_2$CH$_3$, —SCH$_2$CH$_2$CH$_3$, —SCH(CH$_3$)$_2$, —SCH$_2$CH$_2$CH$_2$CH$_3$, —SCH$_2$CH(CH$_3$)$_2$, —SC(CH$_3$)$_3$ and the like.

The term "hydroxyalkyl" used herein refers to one or more hydroxy groups appended to an alkyl group.

The term "azide" refers to a —N$_3$ group. The term "nitro" refers to a —NO$_2$ group.

The term "amino" as used herein refers to —NR$_2$, where R is independently hydrogen, optionally substituted alkyl, optionally substituted heteroalkyl, optionally substituted cycloalkyl, optionally substituted heterocycloalkyl, optionally substituted aryl or optionally substituted heteroaryl. Non-limiting examples of amino groups include NH$_2$, NH(CH$_3$), and N(CH$_3$)$_2$. In some cases, R is independently hydrogen or alkyl.

The term "amido" as used herein refers to —C(O)NH$_2$, —C(O)NR$_2$, —NRC(O)R or —NHC(O)H, where each R is independently hydrogen, optionally substituted alkyl, optionally substituted heteroalkyl, optionally substituted cycloalkyl, optionally substituted heterocycloalkyl, optionally substituted aryl or optionally substituted heteroaryl. In some cases, the amido group is —NHC(O)alkyl or —NHC(O)H. In various cases, the amido group is —C(O)NH(alkyl) or —C(O)NH(substituted alkyl). A non-limiting example of an amido group is —NHC(O)CH$_3$.

As used herein, a substituted group is derived from the unsubstituted parent structure in which there has been an exchange of one or more hydrogen atoms for another atom or group. A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl, and (B) alkyl, heteroalkyl, cycloalkyl, heterocycloalkyl, aryl, amino, amido, carbonyl, thiocarbonyl, alkoxycarbonyl, silyl, sulfonyl, sulfoxyl, alkoxy, aryloxy, and heteroaryl, substituted with at least one substituent selected from:

(i) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl, and (ii) alkyl, heteroalkyl, cycloalkyl, heterocycloalkyl, aryl, amino, amido, carbonyl, thiocarbonyl, alkoxycarbonyl, silyl, sulfonyl, sulfoxyl, alkoxy, aryloxy, and heteroaryl, substituted with at least one substituent selected from:

(a) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl, and (b) alkyl, heteroalkyl, cycloalkyl, heterocycloalkyl, aryl, amino, amido, carbonyl, thiocarbonyl, alkoxycarbonyl, silyl, sulfonyl, sulfoxyl, alkoxy, aryloxy, and heteroaryl, substituted with at least one substituent selected from —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl.

The term "carboxy" or "carboxyl" used herein refers to —COOH or its deprotonated form —COO$^-$. $C_{1-10}$carboxy refers to optionally substituted alkyl or alkenyl groups having a carboxy moiety. Examples include, but are not limited to, —CH$_2$COOH, —CH$_2$CH(COOH)CH$_3$, and —CH$_2$CH$_2$CH$_2$COOH.

The term "alkoxycarbonyl" refers to —(CO)—O-alkyl, wherein the alkyl group can optionally be substituted. Examples of alkoxycarbonyl groups include, but are not limited to, methoxycarbonyl group, ethoxycarbonyl group, propoxycarbonyl group, and the like.

The term "alkylcarbonyl" refers to —(CO)-alkyl, wherein the alkyl group can optionally be substituted. Examples of alkylcarbonyl groups include, but are not limited to, methylcarbonyl group, ethylcarbonyl group, propylcarbonyl group, and the like.

The term "sulfonamido" refers to —SO$_2$NR$_2$, wherein R is independently hydrogen, optionally substituted heteroalkyl, optionally substituted cycloalkyl, optionally substituted heterocycloalkyl, optionally substituted aryl or optionally substituted heteroaryl. In some cases, the sulfonamido group is —SO$_2$NR$_2$ where R is independently hydrogen or an optionally substituted alkyl. Examples of a sulfonamido group include, but are not limited to, —SO$_2$N(CH$_3$)$_2$ and —SO$_2$NH$_2$.

The term "sulfonyl" refers to —SO$_2$R, where R is independently hydrogen or an optionally substituted alkyl, optionally substituted heteroalkyl, optionally substituted cycloalkyl, optionally substituted heterocycloalkyl, optionally substituted aryl or optionally substituted heteroaryl. In some cases, a sulfonyl group is —SO$_2$alkyl, wherein the alkyl group can optionally be substituted. One example of a sulfonyl group is methylsulfonyl (e.g., —SO$_2$CH$_3$).

The term "sulfoxyl" refers to —SOR, where each R is independently hydrogen or an optionally substituted alkyl, optionally substituted heteroalkyl, optionally substituted cycloalkyl, optionally substituted heterocycloalkyl, optionally substituted aryl or optionally substituted heteroaryl. One example of a sulfonyl group is methylsulfonyl (e.g., —SOCH$_3$).

In some cases, the substituent group(s) is (are) one or more group(s) individually and independently selected from alkyl, cycloalkyl, aryl, heterocyclyl, heteroaryl, hydroxy, alkoxy, aryloxy, mercapto, alkylthio, arylthio, cyano, halo, carbonyl, thiocarbonyl, alkoxycarbonyl, nitro, silyl, trihalomethanesulfonyl, trifluoromethyl, and amino, including mono and di substituted amino groups, and the protected derivatives thereof.

The protecting groups that can form the protective derivatives of the above substituents are known to those of skill in the art and can be found in references such as Greene and Wuts, *Protective Groups in Organic Synthesis;* 3$^{rd}$ Edition, John Wiley and Sons: New York, 2006. Wherever a substituent is described as "optionally substituted" that substituent can be substituted with the above-described substituents.

Asymmetric carbon atoms can be present. All such isomers, including diastereomers and enantiomers, as well as the mixtures thereof, are intended to be included in the scope of the disclosure herein. In certain cases, compounds can exist in tautomeric forms. All tautomeric forms are intended to be included in the scope of the disclosure herein. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated.

The salts, e.g., pharmaceutically acceptable salts, of the disclosed therapeutics may be prepared by reacting the appropriate base or acid with a stoichiometric equivalent of the therapeutic.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Similarly, pharmaceutically acceptable derivatives (e.g., esters), metabolites, hydrates, solvates and prodrugs of the therapeutic may be prepared by methods generally known to those skilled in the art. Thus, another embodiment provides compounds that are prodrugs of an active compound. In general, a prodrug is a compound which is metabolized in vivo (e.g., by a metabolic transformation such as deamination, dealkylation, de-esterification, and the like) to provide an active compound. A "pharmaceutically acceptable prodrug" means a compound which is, within the scope of sound medical judgment, suitable for pharmaceutical use in a patient without undue toxicity, irritation, allergic response, and the like, and effective for the intended use, including a pharmaceutically acceptable ester as well as a zwitterionic form, where possible, of the therapeutic. As used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates. Examples of pharmaceutically-acceptable prodrug types are described in Higuchi and Stella, *Prodrugs as Novel Delivery Systems*, Vol. 14 of the A.C.S. Symposium Series, and in Roche, ed., *Bioreversible Carriers in Drug Design*, American Pharmaceutical Association and Pergamon Press, 1987, both of which are incorporated herein by reference.

The compounds and compositions described herein may also include metabolites. As used herein, the term "metabolite" means a product of metabolism of a compound of the embodiments or a pharmaceutically acceptable salt, analog, or derivative thereof, that exhibits a similar activity in vitro or in vivo to a disclosed therapeutic. The compounds and compositions described herein may also include hydrates and solvates. As used herein, the term "solvate" refers to a complex formed by a solute (herein, the therapeutic) and a solvent. Such solvents for the purpose of the embodiments preferably should not negatively interfere with the biological activity of the solute. Solvents may be, by way of example, water, ethanol, or acetic acid.

Methods of Treatment

Methods disclosed herein include methods of treating a disorder, such as a disorder associated with DUB activity or a disorder affected by modulation of DUB activity, or use of a compound disclosed herein in the preparation of a medicament to treat a disorder associated with DUB activity and/or affected by modulation of DUB activity. Further contemplated are methods of treatment wherein a UCH catalytic domain is inhibited. Specific disorders contemplated include pathogenic infections, cancer, developmental and neurodegenerative disorders, Riddle syndrome, Parkinson's disease, Alzheimer's Disease, and genetic disorders requiring or modulated by DUBs, e.g. Fanconi anemia.

In some cases, provided herein are methods that further include identifying a subject having a disorder affected by modulation of activity of a DUB and administering to the subject a compound as disclosed herein.

In various cases, the methods provided herein are prophylactic methods, and a compound or composition as disclosed herein is administered prior to onset of a disorder. In certain cases, the method further comprises identifying a subject at risk of contracting a disorder associated with DUB activity and/or affected by DUB modulation (e.g., a virus, bacterium, and/or parasite as disclosed herein), and administering an effective amount of a compound as disclosed herein.

In some cases, provided herein are methods of inhibiting a pathogenic infection in a cell comprising administering a compound as disclosed herein in an amount that inhibits the pathogenic infection. In various cases, the cell is contacted with the compound. In some embodiments, the cell is an animal cell, or more specifically a mammalian cell or avian cell, or even more specifically a human cell. In various cases, the method comprises treating a condition due to a pathogenic infection. Pathogenic infections contemplated as described elsewhere herein. In various embodiments, the method further comprises identifying a human with a pathogenic infection and/or a condition due to a pathogenic infection and administering an effective amount of a compound as disclosed herein to inhibit the pathogenic infection.

In some cases, provided herein are methods of inihibiting proliferation of a cell comprising contacting the cell with an effective amount of a compound as disclosed herein to inhibit proliferation. In some cases, the cell is a cancer cell. Cancer cells contemplated are described elsewhere herein. In various cases, the compound inhibits a DUB endogenous to the cell and inhibits proliferation.

In various cases, provided herein are methods of treating a neurodegenerative disease comprising administering an effective amount of a compound as disclosed herein to a subject in need thereof. Neurodegenerative diseases contemplated are described elsewhere herein. In some cases, the method treats one or more symptoms of the neurodegenerative disease.

Also disclosed herein are methods of treating one or more symptoms of a genetic disorder comprising administering an effective amount of a compound as disclosed herein to a subject in need thereof. In various cases, the compound inhibits a DUB such that one or more symptoms of the genetic disorder are ameliorated. Genetic disorders contemplated are described elsewhere herein.

In some cases, the methods disclosed herein further comprises administering a second therapeutic agent. The second therapeutic agent can be administered at the same time as the compound as disclosed herein, or at a different time (e.g., separated by a time period of about 1 hour to about 12 hours). In cases where the agents are administered at the same time, the agents can be co-formulated, or formulated in separate formulations but given at the same time or within about 30 minutes of each other. Contemplated second agents include, e.g., an antiviral, antiparasitic, antibacterial, anticancer agent, agent that treats one or more symptoms of a genetic disorder, and/or an agent that treats a neurodegenerative disorder.

Pathogenic Infections

The methods and compounds disclosed herein are useful in treating pathogenic infections, e.g., preventing, inhibiting and/or ameliorating a pathogenic infection or symptom of a pathogenic infection. In some cases, the methods and compounds disclosed herein are useful in treating a condition due to a pathogenic infection.

Intentional contamination of the food and water supplies represents a major threat to the health and health-related services in the US population as a whole and to our armed forces serving throughout the world. Many of the category B water- and food-borne pathogens have specific properties, e.g. low infectious dose, high stability, that make them attractive candidates for this type of bioterrorism. To thwart this potential threat, methods or agents that provide protection or prophylaxis against these defined pathogens are urgently needed. Ideally, agents that provide protection against a wide spectrum of threats would be desirable. The compounds disclosed herein have broad activity against multiple pathogens. For example, WP1130 is a potent inhibitor of diverse category A and B pathogens, and related family members, specifically murine norovirus, *Listeria monocytogenes* and *Toxoplasma gondii* infection as well as Norwalk virus replication. In addition, it also exhibits antiviral activity against Encephalomyocarditis virus, Sindbis virus and La Crosse virus. In certain cells WP1130 inhibits a deubiquitinase and this action results in accumulation of ubiquitinated proteins in the cytoplasmic and aggresomal compartment of the cell. This can establish an inhospitable environment for pathogen infection or replication within the target cell. Thus, WP1130 is used as an antimicrobial inhibitor that can effectively suppress multiple pathogens. This compound and others of formula (I), (II), (IIa) and/or (III) block the infectivity of category A and/or B pathogens, and/or related family members.

Contemplated are pathogens that use a DUB in their infection mechanism. In some cases, the pathogen uses a DUB endogenous to the infected cell. In various cases, the pathogen uses a DUB endogenous to the pathogen.

Contemplated diseases or disorders due to a pathogenic infection include gastroenteritis, encephalitis, respiratory tract infections (e.g., SARS, influenza), virus-induced cancers, rabies, hemorrhagic fevers (e.g., Crimean-Congo, Dengue), Rift valley fever, listeriosis, or toxoplasmosis. Also contemplated diseases or disorders due to a pathogenic infection include meningitis, myocarditis, hepatitis, bacterimia, and skin infections.

Contemplated pathogens include viral, bacterial, fungal, and parasitic pathogens. Contemplated pathogenic viruses include a calicivirus (e.g., norovirus, sapovirus), a picornavirus, a Togavirus, a Bunyavirus, a Rhabdovirus, a herpes virus, an adenovirus, an arterivirus, a coronavirus, a flavivirus, a paramyxovirus, a papillomavirus, a virus encoding for an ovarian tumor (OTU)-like protease, a baculovirus, or a nairovirus. Other contemplated pathogenic viruses include polyoma viruses and retroviruses.

Specific viruses contemplated include encephalomyocarditis virus (EMCV), Sindbis virus (SiNV), La Crosse virus (LaCV), Norwalk virus, Epstein-Barr (EBV), herpesvirus, Dengue virus, respiratory syncytial virus (RSV), papillomavirus, and influenza. Further specific viruses contemplated include cytomegalovirus, BK virus, hepatitis C virus, and HIV.

Contemplated bacteria include *Chlamydia*, *Escherichia*, *Salmonella*, *Yersinia*, *Burkholderia*, *Haemophilus*, *Listeria*, and *Mycobacterium*. Other bacteria contemplated include *Staphylococcus aureus*, or more specifically methicillin-resistant Staph aureus (MRSA).

Contemplated parasites or fungi include *Plasmodium falciparum*, *Toxoplasma gondii*, *Entamoeba histolytica*, *Giardia lamblia*, *Trypanosoma brucei*, *Trypanosoma cruzi*, *Cestoda*, *Clonorchis*, *Opisthorchis*, *Strongylocides*, *Candida*, *Aspergillus*, and *Cryptococcus*.

Cancer

The methods and compounds disclosed herein are useful in treating cancer, e.g., preventing, inhibiting and/or ameliorating a cancer or symptom of cancer. In some cases, the method of treating the cancer comprises inhibiting of a DUB, e.g., a DUB involved in survival or proliferation of the cancer. In various cases, the compound for treating the cancer is WP1130:

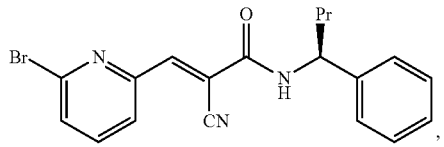

where Pr indicates an n-propyl group.

Specific cancers contemplated include, but are not limited to, chronic myelogenous leukemia (CML), melanoma, acute lymphocytic leukemia, chronic lymphocytic leukemia, acute myelogenous leukemia, B-cell lymphoma, mantle cell lymphoma, multiple myeloma, plasma cell dyscrasia, myeloproliferative disorders, glioblastoma, Kaposi's sarcoma, and nasopharyngeal carcinoma (EBV). Other cancers contemplated include lung cancer, colon cancer, pancreatic cancer, breast cancer, prostate cancer, and solid tumors.

Dosing and Pharmaceutical Formulations

The terms "therapeutically effective amount" and "prophylactically effective amount," as used herein, refer to an amount of a compound sufficient to treat, ameliorate, or prevent the identified disease or condition, or to exhibit a detectable therapeutic, prophylactic, or inhibitory effect. The effect can be detected by, for example, an improvement in clinical condition, reduction in symptoms, or by any of the assays or clinical diagnostic tests described herein. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

Dosages of the therapeutic can alternately be administered as a dose measured in mg/kg. Contemplated mg/kg doses of the disclosed therapeutics include about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg.

As herein, the compounds described herein may be formulated in pharmaceutical compositions with a pharmaceutically acceptable excipient, carrier, or diluent. The compound or composition comprising the compound is administered by any route that permits treatment of the disease or condition. One route of administration is oral administration. Additionally, the compound or composition comprising the compound may be delivered to a patient using any standard route of administration, including parenterally, such as intravenously, intraperitoneally, intrapulmonary, subcutaneously or intramuscularly, intrathecally, topically, transdermally, rectally, orally, nasally or by inhalation. Slow release formulations may also be prepared from the agents described herein in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

Administration may take the form of single dose administration, or a compound as disclosed herein can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition.

In an embodiment, the pharmaceutical compositions are formulated with one or more pharmaceutically acceptable excipient, such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders. A pharmaceutical composition can also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

The pharmaceutical compositions described herein are formulated in any form suitable for an intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents (e.g., sodium carboxymethylcellulose, methylcellulose, hydroxypropyl methylcellulose, sodium alginate, polyvinylpyrrolidone, gum tragacanth, gum acacia); dispersing or wetting agents (e.g., a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate)); and thickening agents (e.g., carbomer, beeswax, hard paraffin or cetyl alcohol). The suspensions may also contain one or more preservatives (e.g., acetic acid, methyl or n-propyl p-hydroxy-benzoate); one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using those suitable dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compounds described herein may be formulated for oral administration in a lipid-based formulation suitable for low solubility compounds. Lipid-based formulations can generally enhance the oral bioavailability of such compounds.

As such, pharmaceutical compositions comprise a therapeutically or prophylactically effective amount of a compound described herein, together with at least one pharmaceutically acceptable excipient selected from the group consisting of medium chain fatty acids and propylene glycol esters thereof (e.g., propylene glycol esters of edible fatty acids, such as caprylic and capric fatty acids) and pharmaceutically acceptable surfactants, such as polyoxyl 40 hydrogenated castor oil.

In some embodiments, cyclodextrins may be added as aqueous solubility enhancers. Exemplary cyclodextrins include hydroxypropyl, hydroxyethyl, glucosyl, maltosyl and maltotriosyl derivatives of α-, β-, and γ-cyclodextrin. A specific cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the invention in the composition.

Combination Therapy

The methods of the embodiments also include the use of a compound or compounds as described herein together with one or more additional therapeutic agents for the treatment of disease conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In some cases, a compound disclosed herein is administered and/or formulated with a second therapeutic—e.g., an antiviral agent, an antibacterial agent, an antiparasitic agent, and/or a chemotherapeutic (e.g, an anti-cancer agent).

Antiviral agents contemplated for use include, without limitation, acyclovir, docosanol, ribarivin, interferons, and the like; cellulose acetate, carbopol and carrageenan, pleconaril, amantidine, rimantidine, fomivirsen, zidovudine, lamivudine, zanamivir, oseltamivir, brivudine, abacavir, adefovir, amprenavir, arbidol, atazanavir, atripla, cidofovir, combivir, edoxudine, efavirenz, emtricitabine, enfuvirtide, entecavir, famciclovir, fosamprenavir, foscarnet, fosfonet, ganciclovir, gardasil, ibacitabine, imunovir, idoxuridine, imiquimod, indinavir, inosine, integrase inhibitor, lamivudine, lopinavir, loviride, mk-0518, maraviroc, moroxydine, nelfinavir, nevirapine, nexavir, nucleotide and/or nucleoside analogues, oseltamivir, penciclovir, peramivir, podophyllotoxin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, morpholino oligonucleotides, ribozyme, protease inhibitors, assembly inhibitors (e.g., rifampicin), and zidovudine.

Antibacterial agents contemplated for use include, without limitation, antibiotics of the β-lactam group such as natural penicillins, semisynthetic penicillins, natural cephalosporins, semisynthetic cephalosporins, cephamycins, 1-oxacephems, clavulanic acids, penems, carbapenems, nocardicins, monobactams; tetracyclines, anhydrotetracyclines, anthracyclines; aminoglycosides; nucleosides such as N-nucleosides, C-nucleosides, carbocyclic nucleosides, blasticidin S; macrolides such as 12-membered ring macrolides, 14-membered ring macrolides, 16-membered ring macrolides; ansamycins; peptides such as bleomycins, gramicidins, polymyxins, bacitracins, large ring peptide antibiotics containing lactone linkages, actinomycins, amphomycin, capreomycin, distamycin, enduracidins, mikamycin, neocarzinostatin, stendomycin, viomycin, virginiamycin; cycloheximide; cycloserine; variotin; sarkomycin A; novobiocin; griseofulvin; chloramphenicol; mitomycins; fumagillin; monensins; pyrrolnitrin; fosfomycin; fusidic acid; D-(p-hydroxyphenyl)glycine; D-phenylglycine; enediynes; benzylpenicillin (potassium, procaine, benzathine), phenoxymethylpenicillin (potassium), phenethicillin potassium, propicillin, carbenicillin (disodium, phenyl sodium, indanyl sodium), sulbenicillin, ticarcillin disodium, methicillin sodium, oxacillin sodium, cloxacillin sodium, dicloxacillin, flucloxacillin, ampicillin, mezlocillin, piperacillin sodium, amoxicillin, ciclacillin, hectacillin, sulbactam sodium, talampicillin hydrochloride, bacampicillin hydrochloride, pivmecillinam, cephalexin, cefaclor, cephaloglycin, cefadroxil, cephradine, cefroxadine, cephapirin sodium, cephalothin sodium, cephacetrile sodium, cefsulodin sodium, cephaloridine, cefatrizine, cefoperazone sodium, cefamandole, vefotiam hydrochloride, cefazolin sodium, ceftizoxime sodium, cefotaxime sodium, cefmenoxime hydrochloride, cefuroxime, ceftriaxone sodium, ceftazidime, cefoxitin, cefmetazole, cefotetan, latamoxef, clavulanic acid, imipenem, aztreonam, tetracycline, chlortetracycline hydrochloride, demethylchlortetracycline, oxytetracycline, methacycline, doxycycline, rolitetracycline, minocycline, daunorubicin hydrochloride, doxorubicin, aclarubicin, kanamycin sulfate, bekanamycin, tobramycin, gentamycin sulfate, dibekacin, amikacin, micronomicin, ribostamycin, neomycin sulfate, paromomycin sulfate, streptomycin sulfate, dihydrostreptomycin, destomycin A, hygromycin B, apramycin, sisomicin, netilmicin sulfate, spectinomycin hydrochloride, astromicin sulfate, validamycin, kasugamycin, polyoxin, blasticidin S, erythromycin, erythromycin estolate, oleandomycin phosphate, tracetyloleandomycin, kitasamycin, josamycin, spiramycin, tylosin, ivermectin, midecamycin, bleomycin sulfate, peplomycin sulfate, gramicidin S, polymyxin B, bacitracin, colistin sulfate, colistinmethanesulfonate sodium, enramycin, mikamycin, virginiamycin, capreomycin sulfate, viomycin, enviomycin, vancomycin, actinomycin D, neocarzinostatin, bestatin, pepstatin, monensin, lasalocid, salinomycin, amphotericin B, nystatin, natamycin, trichomycin, mithramycin, lincomycin, clindamycin, clindamycin palmitate hydrochloride, flavophospholipol, cycloserine, pecilocin, griseofulvin, chloramphenicol, chloramphenicol palmitate, mitomycin C, pyrrolnitrin, fosfomycin, fusidic acid, bicozamycin, tiamulin, or siccanin. In some cases, the antiviral agent blocks virulence products. In such cases, the bacteria is prevented from secreting its virulence factors (toxins etc.) and the immune system can clear the bacteria. See, e.g., Lin et al., *Arch Biochem Biophys.* 2010 Sep. 15; 501(2):214-20. Epub 2010 Jun. 15; Darby et al., *J Antimicrob Chemother.* 2010 July; 65(7): 1424-7. Epub 2010 Apr. 30; Bryk et al, *Biochemistry.* 2010 Mar. 2; 49(8):1616-27; Lin et al., *Nature.* 2009 Oct. 1; 461 (7264):621-6. Epub 2009 Sep. 16; de Carvalho et al., *J Med Chem.* 2009 Oct. 8; 52(19):5789-92; Nathan et al., *Tuberculosis* (Edinb). 2008 August; 88 Suppl 1:S25-33; Bryk, et al., *Cell Host Microbe.* 2008 Mar. 13; 3(3):137-45; Casenghi, et al., *PLoS Med.* 2007 Nov. 6; 4(11):e293; Hu et al., *Mol Microbiol.* 2006 March; 59(5):1417-28; and Kline et al., *J Med Chem.* 2008 Nov. 27; 51(22):7065-74.

Anti-parasitic agents contemplated for use include, without limitation, 2-bromo-2-nitropropane-1,3-diol (BNPD), β-nitrostyrene (BNS), dodecylguanidine hydrochloride, 2,2-dibromo-3-nitrilopropionamide (DBNPA), glutaraldehyde, isothiazolin, methylene bis(thiocyanate), triazines, n-alkyl dimethylbenzylammonium chloride, trisodium phosphate-based, antimicrobials, tributyltin oxide, oxazolidines, tetrakis (hydroxymethyl)phosphonium sulfate (THPS), phenols, chromated copper arsenate, zinc or copper pyrithione, carbamates, sodium or calcium hypochlorite, sodium bromide, halohydantoins (Br, Cl), pyrimethamine, sulfadiazine, sulfadoxine, clindamycin, and spiramycin or mixtures thereof.

Chemotherapeutic agents contemplated for use include, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; non-steroidal antiandrogens such as flutamide; kinase inhibitors, histone deacetylase inhibitors, methylation inhibitors, proteasome inhibitors, monoclonal antibodies, oxidants, anti-oxidants, telomerase inhibitors, BH3 mimetics, ubiquitin ligase inhibitors, stat inhibitors, and nanoparticles.

The invention will be more fully understood by reference to the following examples which detail exemplary embodi-

EXAMPLES

Anti Cancer Assessment of DUB Inhibitors

Chronic myelogenous leukemia (CML) is associated with a chromosomal abnormality in the hematopoietic stem cell that results in the expression of Bcr-Abl with unregulated tyrosine kinase activity. These observations supported the development and clinical testing of the first Bcr-Abl kinase inhibitor, imatinib, which demonstrated remarkable clinical efficacy in CML patients. Imatinib is the frontline therapy for CML and other Bcr-Abl expressing leukemias and most patients treated with imatinib in chronic phase achieve a complete cytogenetic response. However, molecular studies of imatinib treated patients in remission demonstrate that Bcr-Abl expression is still detectable in most cases and discontinuation of imatinib therapy often results in disease relapse. Limited duration of imatinib response is also common in advanced CML patients and imatinib resistance can occur in any stage of the disease. Acquired imatinib resistance and disease progression are frequently characterized by Bcr-Abl mutations and post-translational modification that effect imatinib binding and kinase inhibition. Some of the molecular changes in imatinib resistant disease can be overcome with second generation tyrosine kinase inhibitors which bind Bcr-Abl with higher affinity or inhibit imatinib insensitive kinases associated with resistance. However, the activity of these inhibitors can also be limited by mutations and other mechanisms. Some evidence suggests that Bcr-Abl can function as a protein scaffold to organize signaling complexes that are not fully dependent on kinase activity. These observations suggest that compounds that modulate Bcr-Abl protein levels may be more effective and appropriate for CML therapy in some settings.

WP1130, a small molecule DUB inhibitory activity, rapidly induces ubiquitination of Bcr-Abl, resulting in its re-localization from the cytoplasm into compact, intracellular protein complexes called aggresomes. This modification results in the loss of downstream Bcr-Abl oncogenic signaling. WP1130 directly inhibits Usp9x, a deubiquitinase recently reported to regulate the stability of Mcl-1, an anti-apoptotic protein expressed in many tumor, including hematological malignancies. Mcl-1 is associated with drug resistance and survival in hematopoietic malignancies. WP1130-mediated Usp9x inhibition is associated with reduced Mcl-1 levels, and together with blocked Bcr-Abl kinase signaling, results in the rapid onset of apoptosis. These results suggest that targeting specific ubiquitin cycle regulators may emerge as a novel therapeutic approach to inhibit oncoprotein signaling and reduce elevated apoptotic thresholds.

The mechanism of action of WP1130 as an anti-cancer treatment was investigated. By screening multiple kinases expressed and activated in CML cells, only Bcr-Abl down-regulation in CML cells was detected. Thorough examination showed that WP1130 action is initiated in the cytoplasmic fraction of the cell, which may partially explain the selectivity for the predominantly cytoplasmic Bcr-Abl protein. Other kinases, such as Jak2, Lyn and PI3-K are reported to be detected in the membrane fraction or associated with transmembrane receptors. Analysis of several tumor types supports the observed selectivity of WP1130 for specific cytoplasmic kinases as transmembrane kinases such as the HER family, c-kit and Flt-3 are insensitive to WP1130. However, in hematologic tumors that do not express Bcr-Abl, Jak2 undergoes rapid ubiquitination and aggresomal trafficking in response to WP1130. This may explain the reported Jak/Stat inhibitory activity of WP1130 and less active derivatives such as WP1066 and WP1034. Based on the activities reported here and previous observations, WP1130 initiates a series of events that result in the ubiquitination of proteins such as Bcr-Abl. This modification signals for proteins to traffic or transfer to organelles and in the case of Bcr-Abl, the aggresome appears to be the main site for transfer. Aggresomes are typically formed in response to protein misfolding or overload and are proposed to be cytoprotective by reducing the potential for excess protein to interfere with cellular metabolism. However, in the case of Bcr-Abl, loss of signaling, even for short intervals, is associated with the onset of CML cell apoptosis. In this regard, WP1130 initiated compartmentalization of Bcr-Abl converts a cytoprotective process into a cytodestructive one. Based on the observed inhibition of DUB activity by WP1130 it appears that DUB targets may be associated with the observed WP1130 activity.

A subset of DUB enzymes may underlie some of the protein ubiquitination and apoptotic activity of WP1130. Although no major change in total DUB activity in CML cells was detected after WP1130 contact, inhibition of specific DUBs, such as Usp9x, was detected. Usp9x activity was sensitive to WP1130 in assays from intact cells, cell lysates and enzyme preparations at concentrations necessary to induce Bcr-Abl trafficking and apoptosis. Recent reports suggest that Usp9x increases Mcl-1 stability, extending its half-life by preventing its proteasomal destruction through de-ubiquitination (see, e.g., Schwickart, et al., *Nature,* 463:103-107 (2010). A reduction in Mcl-1 levels in WP1130 treated cells paralleled inhibition of Usp9x activity. To determine whether Usp9x inhibition was also associated with Bcr-Abl trafficking, Usp9x was silenced in CML cells and demonstrated Mcl-1 down-regulation but no effect on Bcr-Abl ubiquitination or its cellular localization. While Usp9x expression and activity are highly relevant to Mcl-1 control in multiple tumors, it may also be of high significance to the sustained viability of CML stem cells that are only moderately responsive to Bcr-Abl kinase inhibition. Multiple studies have shown that early leukemogenic progenitors overexpress Mcl-1 as a consequence of activation of a number of upstream cascades including Bcr-Abl and cytokine-mediated Stat activation.

Until recently, the role of Usp9x as a modulator of Mcl-1 activity in transformed cells was unknown but inhibitors of Usp9x are of therapeutic importance in a number of settings. In this regard, WP1130 is highly suited for CML based therapy as it has indirect effects on Bcr-Abl signaling through kinase sequestration into aggresomes and direct inhibition of Usp9x activity, which may be essential in stabilizing CML stem cell survival. In light of the importance of Usp9x in control of Mcl-1 levels, compounds like WP1130 are useful in overcoming apoptotic resistance associated with Usp9x activity and Mcl-1 protection.

All compounds were made up as 20 mM stock solutions (in DMSO), stored frozen at −20° C. and diluted into aqueous media just before use. Other reagents used in this study were obtained from the following sources: Bortezomib (Millennium Pharmaceuticals; Cambridge, Mass.); Mini-Complete and PhosSTOP inhibitory cocktails (Roche Applied Science, Indianapolis, Ind.); Ub-AMC, Hemagglutinin-tagged ubiquitin vinyl methyl sulfone (HA-UbVs), Suc-LLVY-AMC, Boc-LRR-AMC, MG-132, Lactacystin and 20S human proteasome (BostonBiochem, Cambridge, Mass.). Affinity matrices of Rap80-agarose and Ataxin-agarose beads and purified poly-ubiquitin chains (K-48/K-63 linked) were also obtained from Boston Biochem. 17-Allylamino-17-demethoxygeldanamycin (17-AAG) was purchased from LC Laboratories (Woburn, Mass.).

Cell Lines and Patient Samples—

K562, K562R, BV-173, BV-173R and WDT-2 cell lines were grown and maintained as previously described. BaF3 cells were maintained in the same media, supplemented with 1 ng/ml IL-3 (PeproTech, Rocky Hill, N.J.). BaF3 cells were also transformed with unmutated or mutant Bcr-Abl as previously described or transformed with an upstream eGFP coding sequence inserted in frame into the Bcr-Abl expression vector. All cells were cultured and maintained at 37° C. in a humidified atmosphere.

Patient specimens were from CML patients derived from patients when imatinib therapy failed to continually control their disease. Mononuclear cells were isolated from blood samples by density centrifugation (Ficoll-Hypaque), washed with PBS, resuspended in cell culture media (RPMI-1640, 10% fetal bovine serum) and incubated overnight at 37° C. in a 5% $CO_2$ incubator before treatment with inhibitors.

Plasmids and Electroporation—

The eGFP coding region was cloned from pLEGFPc by PCR using a 5' primer with an EcoR1 restriction site: GAATTCCGCCACCATGGTGAGCAAGGGCG (SEQ ID NO: 1) and a 3' primer with an EcoRV restriction site: GATATCGACTTGTACAGCTCGTCCATGCCGAGAGTG (SEQ ID NO: 2). The pBSsk+ vector containing p210Bcr/Abl cDNA (derived from pSG5) was digested with ClaI and EcoRI and the EcoR1 site was blunted. The eGFP fragment was digested with ClaI and EcoRV and ligated into pBSsk+/p210Bcr/Abl to generate the 5' tagged eGFPp210Bcr/Abl. The pMX/eGFPp210Bcr/Abl was constructed by ligation of the eGFPp210Bcr/Abl into the pMXpuro vector with the deletion of the IRES eGFP using EcoRI and NotI. BaF3 cells were electroporated with pMX/eGFPp210Bcr/Abl or pMX/eGFPp120Bcr/Abl-T315I (constructed by subcloning from the pSG5-Bcr/Abl/T315I vector using Kpn1/BsrG1 sites). All mutations and vector inserts were confirmed by sequencing. Cells were selected for puromycin resistance (2 µg/ml; 2 weeks) and enriched for Bcr-Abl expression by fluorescence-activated cell sorting of eGFP positive cells (FACSCANTO-II, Becton Dickenson). Bcr-Abl expression and cytokine-independence were confirmed by immunoblotting and apoptotic induction by imatinib incubation but not IL-3 withdrawal.

Lysate Preparation, Antibodies and Western Blotting—

Total cell lysates were prepared by boiling and sonicating cell pellets in 1× Laemmli reducing sample buffer. To prepare detergent soluble and insoluble fractions, cells were lysed in cold isotonic lysis buffer [10 mM Tris-HCl (pH 7.5), 0.5% Triton X-100, 150 mM NaCl along with Mini-Complete and PhosSTOP] for 15 min on ice and centrifuged 10 min at 20,000 RCF. The clarified supernatant was used as the detergent soluble cell fraction. The residual pellet was washed and extracted in Laemmli reducing sample buffer and briefly sonicated to derive the detergent insoluble fraction. Equal volumes of cellular lysate or equal protein amounts were electrophoresed on SDS-PAGE gels and transferred to nitrocellulose membranes (Whatmann, Dassel, Germany). Proteins were detected by immunoblotting.

Antibodies used in this study were purchased from the following sources: anti-pY-Stat5, pY-CrkL, anti-PARP, anti-Mcl-1 (Cell Signaling Technology, Danvers, Mass.), anti-actin (Sigma-Aldrich, St. Louis, Mo.); polyclonal anti-ABL (K12), monoclonal anti-ABL (SH2 domain; 8E9), anti-ubiquitin clone P4D1, anti-HSP90, anti-HSP70, anti-Jak2, anti-CrkL, anti-α-tubulin, horseradish peroxidase—conjugated goat anti-rabbit/mouse/rat IgG (Santa Cruz Biotechnology, Santa Cruz, Calif.); anti-HA clone 3F10 (Roche Applied Science Indianapolis, Ind.) and anti-Usp9x (Bethyl Laboratories, Montgomery, Tex.).

Proteasome Activity Assay—

Fluorogenic substrate Suc-LLVY-AMC was used to assay for the chymotryptic-like activity of the 20S proteasome. To assay for in vivo proteasome inhibition cells were treated with WP1130 (5 µM) or MG132 (5 µM) for 2 hours and lysed in ice-cold lysis buffer (50 mM HEPES, pH 7.5, 5 mM EDTA, 150 mM NaCl, 1% Triton X-100). Lysates were clarified by centrifugation at 20,000 RCF for 10 min and equal amounts of protein from each sample were incubated at 37° C. with 100 µM fluorogenic substrate. To assay for direct inhibition of the 20S proteasome in vitro, purified 20S human proteasome (200 ng) was incubated with WP1130 (5 µM), MG132 (5 µM) or Lactacystin (5 µM) for 30 min at 37° C. before addition of the substrates. Fluorescence intensity was measured using a spectrophotometer at excitation 360 nm & emission 460 nm. Assays were performed in triplicate, and statistical significance was determined with a paired Student's t test.

Reactive Oxygen Species Assay (ROS)—

Leukemic cells ($1\times10^6$) were treated with DMSO, WP1130 (5 µM) or a positive [$H_2O_2$ (0.5 mM)] or negative [DTT (1 mM)] effector of ROS content for 2 hours at 37° C. Cells were washing and resuspended in PBS containing 10 µM DCFDA and further incubated for an additional 15 min in the dark. After washed in PBS, cells were transferred to individual wells of a 96-well plate and fluorescence intensity was measured using a spectrophotometer at excitation 492 nm & emission 520 nm. Assays were performed in triplicate, and statistical significance was determined with a paired Student's t test.

Confocal Microscopy—

Control and treated eGFP-Bcr/Abl transformed BaF3 cells were washed twice in PBS, followed by fixation using 4% formaldehyde for 15 min. The cells were spun onto poly-lysine coated slides using a Cytopro centrifuge (Wescor, Logan, Utah) and permeabilized in 0.5% Triton X-100 for 5 min. Slides were then incubated in blocking solution (5% goat serum) for 1 h at room temperature. Incubation with the primary antibodies (1:100) was carried out for 4 h at room temperature or overnight at 4° C., and the slides were washed three times with 0.2% Triton X-100/PBS buffer. Alexa-Fluor anti-mouse and Alexa-Fluor anti-rabbit immunoglobulin antibodies were used as secondary antibodies. The slides were washed three times and the nucleus was stained with Hoechst 33342. Images were acquired using an Olympus confocal microscope FV-500 (Tokyo, Japan).

In Vitro Debuiquitination Assays—Ub-AMC Protease Assay.

Cells were lysed in ice cold DUB buffer containing 50 mM Tris-HCl, pH 7.5, 0.5% NP-40, 5 mM $MgCl_2$, 150 mM NaCl and 1 mM phenylmethylsulfonylfluoride. Briefly, 5 µg of clarified lysate from untreated or treated cells was incubated with 500 nM Ub-AMC in a 100 µL reaction volume at 37° C. and the release of AMC fluorescence was recorded at ex/em 380/480 using a spectrofluorometer. USP9x was immunoprecipitated from 500 µg of cell lysate and incubated in DUB buffer containing NEM, WP1130 or DMSO in a 100 µL reaction volume for 30 min. The reaction was initiated by the addition of 500 nM Ub-AMC and the release of AMC-fluorescence was recorded.

Ub Chain Disassembly.

In vitro disassembly of purified polyubiquitin chains (K-48/K-63 linked) was performed as previously described.

Five µg of lysate from untreated or WP1130 treated cells were prepared in DUB buffer and incubated with K48- or K-63 linked chains (1 µg) for 10 min at 37° C. The extent of chain disassembly was assessed by ubiquitin immunoblotting.

Deubiquitinase Labeling Assays

To assay for changes in activity of cellular deubiquitinase enzymes, leukemic cells were lysed in DUB buffer (50 mM Tris pH 7.4, 5 mM $MgCl_2$, 150 mM NaCl) for 10 min at 4° C. The lysates were centrifuged at 20,000 RCF for 10 min and the supernatant was used for DUB labeling. Equal amounts of lysate were incubated with 500 ng of HA-UbVs for 1 hr at room temperature, followed by boiling in reducing sample buffer and resolving by SDS-PAGE. HA immunoblotting was used to detect DUB labeling.

To determine the selectivity for Bcr-Abl, several kinases expressed in CML cells were assessed for WP1130-mediated down-regulation (at 5 µM WP1130 for 2 hours)—including Bcr-Abl, c-Abl, BCR, Actin, Jak2, gp130, Lyn, Akt, Pt-3K, Jnk, Erk1/2. Only Bcr-Abl protein levels were reduced upon WP1130 treatment, suggesting specificity for this chimeric protein. eGFP-Bcr-Abl transformed BaF3 cells were left untreated or treated with 5 µM imatinib or WP1130 for 2 hours before analyzing equal protein cell lysate for Bcr-Abl and actin. eGFP-tagged Bcr-Abl (WT) was expressed in BaF3 cells and rapid down-regulation of the ectopically expressed Bcr-Abl upon WP1130 treatment was detected. Stable BaF3 cell lines expressing WT and T315I variants of Bcr-Abl were established and exhibited high sensitivity to WP1130-mediated apoptosis in both cases. BaF3 cells transformed by eGFP-Bcr-Abl without (W/T) or with the T315I Bcr-Abl mutation were treated with imatinib or WP1130 at the indicated concentration for 72 hours before assessing cell growth and survival by MTT staining. The effects of WP1130 on eGFP-Bcr-Abl were investigated by fluorescent microscopy. A rapid accumulation of eGFP-Bcr-Abl into compact, high density Bcr-Abl clusters were observed after WP1130 incubation.

Hsp90 inhibition by geldenamycin and analogues has been reported to affect Bcr-Abl stability and cellular distribution. The anti-proliferative effects of Hsp90 inhibitor (17-AAG) was compared to those of WP1130. Both WP1130 and 17-AAG displayed anti-proliferative effects in CML lines expressing either WT Bcr-Abl (BV-173) or T315I mutant Bcr-Abl (BV-173R) but distinctions in the onset of apoptosis were observed. A reduction in Hsp90 and Bcr-Abl association was noted in 17-AAG treated cells, which can lead to Bcr-Abl down-regulation through ubiquitination. However, treatment with WP1130 resulted in an increased association between Bcr-Abl and Hsp90, suggesting a distinct mechanism for Bcr-Abl down-regulation. The impact of WP1130 and 17-AAG on cellular ubiquitinated protein levels and Hsp70 protein levels was assessed, as Hsp90 inhibition results in Hsp70 induction. 17-AAG had no effect on ubiquitinated protein levels but lead to the induction of Hsp70. WP1130 induced a rapid increase in ubiquitinated proteins in the detergent soluble cell fraction with substantial accumulation in the detergent insoluble fraction at later time points. Hsp70 levels were also increased in WP1130 treated cells, but were not associated with Hsp90 inhibition.

BV-173 cells were treated with 5 µM WP1130 for 0, 1 or 2 hours before assessing Bcr-Abl, pY-Stat5, and Jak2 protein levels in total cell lysates, detergent-soluble and insoluble fractions. BV-173 and BV-173R cells were treated with 5 µM WP1130 for 2 hours before detergent soluble and insoluble cell lysates were blotted for Bcr-Abl (K12 antibody). K562R cells were treated with 5 µM WP1130 for 2 hours before proteins derived from the total cell fraction, detergent-soluble and insoluble fractions were probed for Bcr-Abl, Jak2, pY-Lyn, and Lyn. BaF3 cells transformed with eGFP-Bcr-Abl with the T315I mutation were treated with 5 µM WP1130 for 0, 0.5, 1, 2, 4, or 6 hours before detergent soluble cell lysates were immunoblotted for Bcr-Abl, pY-Stat5, Stat5, and PARP. Mononuclear cells from two CML patients that were progressing on imatinib therapy were treated with 5 µM WP1130 for 4 hours before equal volume cell lysates representing the detergent soluble and insoluble cell fraction were probed for Bcr-Abl. The detergent soluble cell fraction was also immunoblotted for Bcr-Abl substrate phosphoproteins (pY-Stat5, pY-CrkL) and their total protein levels. Since ubiquitination can mediate protein degradation and intracellular trafficking, Bcr-Abl content in WP1130 treated cells was examined. WP1130 treatment resulted in a rapid and near complete trafficking of Bcr-Abl from the detergent soluble to insoluble cell fraction. Compartmentalization of Bcr-Abl into the insoluble fraction was associated with loss of phosphorylation of Stat5 without affecting Jak2. However, no significant change in the Bcr-Abl protein content in whole cell extracts was noted. Increased Bcr-Abl protein content in the detergent insoluble cell fraction was also observed in imatinib-resistant CML cells, such as BV-173R expressing T315I-Bcr-Abl and K562R overexpressing Lyn kinase. Neither Jak2 nor Lyn detergent solubility were affected by WP1130 in these cells. In BaF3 transfectants expressing Bcr-Abl, loss of Bcr-Abl from the detergent soluble fraction was associated with reduced substrate phosphorylation (pY-Stat5) and the onset of apoptosis (PARP cleavage). Bcr-Abl in primary CML cells from imatinib resistant patients was also observed to translocate to the detergent insoluble fraction following WP1130 incubation and was associated with loss of Bcr-Abl substrate (pY-Stat5, pY-CrkL) phosphorylation. The detergent insoluble fraction is highly enriched in cytoskeletal proteins and components of cellular structures called aggresomes. These results suggest that WP1130 blocks Bcr-Abl substrate phosphorylation through compartmentalization of Bcr-Abl.

K562 cells were incubated with 5 µM WP1130 for 30 min before detergent soluble cell extracts were subjected to Hsp90 immunoprecipitation followed by immunoblotting for Bcr-Abl, ubiquitin or Hsp90. K562 cells were incubated with WP1130 (5 µM), $H_2O_2$ (500 mM) or DTT (1 mM) for 2 hr at 37° C. Cells were then washed and re-plated in media containing DCFDA for 20 min at 37° C. DCFDA fluorescence was read and used as a measure of ROS production in treated samples. Similar results were obtained in two additional CML cell lines (WDT-2, BV-173). K562 cells were left untreated or treated with 5 µM of WP1130 or MG-132 for 2 h at 37° C. Protein lysates were incubated with proteasome substrate and activity was determined by fluorogenic substrate cleavage. Purified 20S proteasome was incubated with 5 µM MG-132, Lactacystin or WP1130 before assaying proteasome activity. Similar results were obtained with 2 additional CML cell lines. K562 cells were treated with 50 nM bortezomib or 5 µM WP1130 before equal volumes of lysate from the detergent-soluble, insoluble and total cell lysate were immunoblotted for Bcr-Abl or ubiquitin. Both Bz and WP increased ubiquitin content but only WP affected Bcr-Abl and detergent insoluble ubiquitinated protein levels. Ubiquitinated protein content can be increased as a consequence of proteasome inhibition, loss of protein chaperone activity or increased cellular oxidation leading to protein misfolding. However, the loss of Hsp90 association with Bcr-Abl was not detected and no elevated reactive oxygen species in WP1130 treated cells was observed. Further, WP1130 did not suppress either 20S proteasome activity in intact CML cells or purified 20S proteasome subunit preparations, eliminating the possibility that WP1130 acts as a proteasome inhibitor. WP1130 was compared to the potent 20S proteasome inhibitor bortezomib to determine whether they shared impact on protein ubiquitination and Bcr-Abl compartmentalization. Both compounds increased ubiquitinated protein content but only WP1130 induced accumulation of detergent insoluble ubiquitinated proteins. WP1130 treatment lead to the reduction in Bcr-Abl from the detergent soluble fraction and the appearance of Bcr-Abl in the detergent insoluble fraction, but no change in total Bcr-Abl content was noted. Bortezomib elevated ubiquitinated protein levels but had no effect on Bcr-Abl detergent solubility or protein levels.

To determine whether Bcr-Abl was ubiquitinated in WP1130 treated cells, CML cells were treated with WP1130 for short intervals (30 min) to allow recovery of Bcr-Abl from the detergent soluble fraction (for direct immunoprecipitation). WP1130 stimulates Bcr-Abl ubiquitination and trafficking in CML cells. WDT-2 cells were treated with vehicle alone (control) or 5 µM WP1130 for 30 min at 37° C. before equal volume cell lysates were resolved into total, detergent-soluble or detergent-insoluble fractions and probed for Bcr-Abl or ubiquitin. Equal protein (400 µg) detergent soluble cell lysate from WP treated or control cells was treated with 1% SDS at 60° C., diluted to 0.1% SDS and subjected to immunoprecipitation with anti-Abl (K12). The IP was washed, resolved on gels and immunoblotted for Abl or ubiquitin. K562 or BV-173 cells were treated with WP or control and equal protein detergent-soluble cell lysates were subjected to Abl immunoprecipitation and blotting for Abl and ubiquitin. An aliquot of the same lysate (200 µg) from control and treated cells was also subjected to affinity enrichment for K48-linked (Ataxin) or K63-linked (Rap80) ubiquitin polymers. Bound protein was eluted and subjected to Abl immunoblotting. eGFP-Bcr-Abl transformed BaF3 cells were treated with vehicle alone or 5 µM WP1130 for 4 hours before cells were fixed, cytospun onto slides and permeabilized. After blocking reactive sites, slides were incubated with anti-ubiquitin antibody (1:100), washed and antigen detected with Alexa-Fluor antibodies. The slides were washed again and stained for nucleus detection with Hoechst 33342. Bcr-Abl immunoblotting after immunoprecipitation from WP1130 treated cells demonstrated a moderate reduction in Bcr-Abl recovery from the detergent-soluble extract but a marked increase in its ubiquitination. Blotting confirmed a significant increase of Bcr-Abl and ubiquitinated proteins in the insoluble fraction from WP1130 treated cells. To determine whether Bcr-Abl modification by WP1130 was due to transfer of specific ubiquitin polymers to the kinase, soluble cell lysates were subjected to immunoprecipitation with agarose beads conjugated to proteins with high affinity for K48-linked (Ataxin) or K63-linked (Rap80) ubiquitin polymers and protein eluates were immunoblotted for Bcr-Abl. Recovery of Bcr-Abl/K63-linked ubiquitin polymers was more prominent in WP1130 treated cells and suggested that increased K63-linked ubiquitin polymers on Bcr-Abl underlies the signal for its translocation into detergent insoluble complexes.

To further assess Bcr-Abl ubiquitination and cellular distribution, eGFP-Bcr-Abl BaF3 transformants were examined by confocal microscopy. Treatment with WP1130 resulted in the clustering of Bcr-Abl and ubiquitin in juxta-nuclear complexes resembling aggresomes. Biochemical studies support the inclusion of other proteins defining the aggresome in complex with Bcr-Abl from WP1130 treated cells. These results suggest that WP1130 stimulates increased ubiquitination of Bcr-Abl (primarily with K63-linked polymers) to initiate its transfer to the aggresome.

A cross-conjugated α,β-unsaturated dienone with two sterically accessible electrophilic β-carbons is a molecular determinant of isopeptidase or deubiquitinase (DUB) inhibitor activity. The presence of these determinants in WP1130 prompted an investigation of its potential DUB inhibitory activity. Lysates derived from untreated or WP1130 treated cells were incubated with purified ubiquitin polymers ($Ub_1$-$Ub_5$) and the relative recovery of polymers was assessed by immunoblotting. Lysates derived from WP1130 treated CML cells showed a partial protection of both K48 and K63 linked ubiquitin polymers from disassembly, supporting the possibility of DUB inhibition by WP1130. To more closely examine DUB inhibition, lysates from untreated, WP1130 treated (1-8 hours) or N-ethylmaleimide [NEM] treated CML cells were incubated with fluorescent DUB substrate (Ub-AMC) and activity monitored over time. Lysates derived from cells treated with the non-specific DUB inhibitor NEM, completely blocked substrate hydrolysis whereas lysates from WP1130 treated CML cells showed limited effects on Ub-AMC hydrolyzing activity. These results suggested that WP1130-mediated ubiquitin changes may be mediated through inhibition of a single or limited subset of DUBs. To examine the impact on specific DUB activity, CML cells were treated with WP1130 and lysates were incubated with a HA-tagged irreversible DUB substrate, HA-UbVS, as described previously. The covalent modification of DUBs by this construct allows analysis of DUB activity by HA immunoblotting. Inhibition of DUB activity by WP1130 may be detected by a reduction in HA-labeling of WP1130-sensitive DUBs. Lysates from WP1130 treated cells showed a reduced capacity to label one prominent high MW DUB identified as Usp9x. Usp9x is predominantly expressed in the cytoplasmic, detergent-soluble, fraction and WP1130 treatment did not affect Usp9x recovery or protein content. To determine whether WP1130 directly affects Usp9x activity, CML cell lysates were incubated with WP1130 for 1 h before incubation with HA-UbVs DUB substrate and analysis by HA blotting. Usp9x labeling was completely blocked in the presence of WP1130, suggesting direct Usp9x inhibition. Other DUBs, denoted by arrows, were also affected by WP1130, suggesting that WP1130 targets additional DUBs with, as yet, unknown specificity or selectivity. To confirm direct DUB inhibition, Usp9x was immunoprecipitated, washed extensively and incubated with WP1130 before assessing DUB activity using the fluorescent DUB substrate, Ub-AMC. The rate of substrate hydrolysis was measured and compared in DMSO and WP1130 incubated assays to estimate the percent DUB inhibition by WP1130. Normal IgG immunoprecipitates and treatment of Usp9x immunoprecipitates with NEM did not result in substrate hydrolysis. When compared to control reactions, WP1130 reduced Usp9x activity by >80%, demonstrating that WP1130 functions as a subset specific DUB inhibitor with activity against Usp9x.

Recent reports demonstrate that Usp9x controls Mcl-1 deubiquitination and degradation. To determine whether Usp9x inhibition by WP1130 affects Mcl-1 levels in CML cells, total cell extracts were immunoblotted for Mcl-1. WP1130 reduced Mcl-1 levels in a temporal fashion that paralleled Usp9x inhibition and was active in both imatinib sensitive and resistant CML cells. To determine whether Bcr-Abl or Jak2 inhibition could also reduce Usp9x activity, CML cells were treated with WP1130, Bcr-Abl selective (imatinib), Jak2 selective (TG101209) or multi-kinase inhibitor (dasatinib) for 4 hours before cell lysates were subjected to HA-UbVs labeling and direct Usp9x immunoblotting. In vitro treatment of cell lysates with WP1130 (5 µM, 30 min) was also included to confirm direct Usp9x inhibition.

WP1130 effectively reduced Usp9x activity while none of the kinase inhibitors examined had significant Usp9x inhibitory activity.

DUB Inhibition in Leukemia and Myeloma

Ubiquitination and ubiquitin-like protein modification play a major role in directing the fate and function of most cellular proteins. Several key enzymes in these pathways are amplified, or modified in diseased cells and provides rationale for development of small molecules that inhibit or modulate their activity. Major advances have been made in selective targeting of specific enzymes in these pathways; some with clinical impact. Due to the specialized role of DUBs in the ubiquitin cycle and their emerging role in control of multiple signaling pathways and oncoproteins, DUB inhibitors are useful anti-cancer agents. In view of the ability of WP1130 to induce accumulation of polyubiquitinated proteins and promotes tumor cell apoptosis WP1130 was identified as a useful anti-cancer agent.

Peptide based potent, irreversible inhibitors of DUBs, such as ubiquitin aldehyde and ubiquitin vinyl sulfone (UbVS), are known. However, their therapeutic potential is limited by their high molecular weight and limited cellular bioavailability. Other small molecule compounds, such as D12-prostaglandin J2 were initially shown to inhibit ubiquitin iso-peptidase activity in cells ($IC_{50}$ about 30 μM) and cause cellular accumulation of ubiquitinated proteins and cell death. A key molecular determinant required for DUB inhibitory activity, α,β-unsaturated ketone with sterically accessible β-carbon, was noted in this compound and lead to the identification of additional inhibitors with similar activities, such as dibenzylideneacetone (DBA; $IC_{50}$ about 20-40 μM), curcumin ($IC_{50}$ about 80-100 μM) and shikoccin (NSC-302979; $IC_{50}$ about 15 μM). However, the profile of specific DUBs affected by these compounds has not been described.

Using multiple in vivo and in vitro assays, mechanistic evidence is provided herein that WP1130 acts as a partially selective DUB inhibitor. The data herein show that WP1130 suppresses the activities of major cellular deubiquitinases such as USP5, UCH-L1, USP9x, USP14 and UCH37. Inhibition of multiple DUBs is likely to induce multiple predictable cellular changes, such as: (i) increased accumulation of polyubiquitinated proteins/unanchored polyubiquitin chains, (ii) decline in the pool of monomeric ubiquitin, (iii) slower rate of polyubiquitin disassembly, (iv) an overall decrease in individual DUB activities, and (v) effect cellular levels/activities of DUB regulated oncoproteins, such as p53 and Mcl-1. USP5 and UCH37 are known to deubiquitinate both K48-linked and K63-linked polyubiquitinated proteins.

A marked increase in cellular ubiquitinated proteins, arising either due to proteasome inhibition or loss of cellular DUB activity can trigger aggresome formation. Formation of aggresomes under conditions of stress results in a temporary cellular cytoprotective event, relocating vast amounts of accumulated ubiquitinated proteins to the aggresomal insoluble fraction. Data suggests that WP1130 treatment causes accumulation of polyubiquitinated Jak2 and Bcr-Abl into detergent insoluble aggresomes, thereby suppressing tumor cell proliferation.

Therefore, trafficking of oncoproteins which play a crucial role in proliferation, survival and growth factor signaling into the aggresome, where they are unable to function, is predicted to be detrimental to tumor cells. However, the DUB(s) that play a crucial role in regulating these oncogenic kinases is not currently known. By xenograft mouse models of CML and melanoma, WP1130 treatment effectively suppresses tumor growth in vivo. Together these observations indicate that WP1130 acts as a therapeutic agent through its effects on DUB activity.

It is noteworthy that several of the DUBs targeted by WP1130 have recently been shown to be key regulators of the stability and turnover of specific oncogenes and apoptotic regulators, including Mcl-1 and p53. Other DUBs are suggested to play a direct role in transformation and control of ubiquitinated protein entry into the proteasome. Still others that may be targeted by WP1130 have recently been shown to play a role in unregulated cell growth and tumor cell oncogene addiction.

Cell Culture, Chemical Reagents and Enzymes—

Human multiple myeloma MM1.S and mantle cell lymphoma Z138 cells were grown in RPMI-1640 supplemented with 10% fetal bovine serum (FBS) (Invitrogen, Carlsbad, Calif.). Adherent cell lines such as human embryonic kidney 293T (HEK293T) cells were cultivated in Dulbecco modified essential medium (DMEM) containing 10% FBS. All cells were cultured and maintained at 37° C. in a humidified atmosphere. RPMI-1640 and DMEM were purchased from HyClone (Thermo Fisher Scientific, Waltham, Mass.).

Plasmid and siRNA Transfection—

HEK293T cells ($10^5$ cells/well) were seeded into 6-well plates 24 hours prior to transfection. 500 ng of HA-tagged ubiquitin (WT/63O/48O) was used to transfect per well using Fugene HD (Roche) following the manufacturer's protocol. After overnight incubation following transfection, the cells were split into 2 wells and incubated for an additional 24 hours before being treated with vehicle alone (DMSO) or WP1130.

ON-TARGETplus siRNA (Thermo-scientific-Dharmacon) for USP9x and USPS (30 nM each) were used to knockdown USP9x and USP5 in HEK293T cells using Lipofectamine 2000. Protein levels were estimated after 72 hours of transfection by western blotting.

Western Blotting—

Whole cell lysates were prepared by boiling and sonicating the cell pellets in 1× Laemmli reducing sample buffer. To prepare detergent soluble and insoluble fractions, cells were lysed in cold isotonic lysis buffer [10 mM Tris-HCl (pH 7.5), 0.5% Triton X-100, 150 mM NaCl along with Mini-Complete and PhosSTOP] for 15 min on ice and centrifuged 10 minutes at 20,000 RCF. The clarified supernatant was used as a source of the detergent soluble cell fraction. The detergent insoluble fraction was extracted by the sonication of residual pellet in equal volumes of boiling 1× Laemmli reducing sample buffer. Equal volumes of cellular lysate or equal protein amounts were electrophoresed on SDS-PAGE gels.

Antibodies used in this study were purchased from following sources: anti-actin (Sigma-Aldrich, St. Louis, Mo.); anti-ubiquitin clone P4D1, anti-HDAC6, anti-HSP90, anti-HSP70, anti-20S proteasome, anti-HDAC6, goat anti-rabbit/mouse/rat IgG-conjugated horseradish peroxidase (Santa Cruz Biotechnology, Santa Cruz, Calif.); anti-flotillin1, anti-MCL1 (BD Biosciences, San Jose, Calif.); anti-p53 (Millipore, Billerica, Mass.); anti-USP9x, anti-USPS (Bethyl laboratories, Montgomery, Tex.); anti-PARP (Cell signaling Technology, Danvers, Mass.); anti-HA clone 3F10 (Roche Applied Science Indianapolis, Ind.).

Sub-Cellular Fractionation—

Z138 cells were either treated with 5 μM WP1130 or DMSO for 2 hours, followed by their lysis and processing to isolate the cytosolic, membrane, nuclear and cytoskeletal fractions. The ProteoExtract Subcellular Proteome Extraction Kit (Calbiochem, San Diego, Calif.) was used to extract each fraction according to the manufacturer's instruction. Markers for each fraction were included to assess the purity of each fraction.

Confocal Microscopy—

HEK293T cells treated with WP1130 or DMSO for 4 hours were washed twice in PBS, followed by fixation using 4% formaldehyde for 15 min. The cells were permeabilized in 0.5% Triton X-100 for 5 min. Slides were then incubated in blocking solution (5% goat serum) for 1 h at room temperature. Incubation with the primary antibodies (1:100) was carried out overnight at 4° C., and the slides were washed three times with 0.2% Triton X-100/PBS buffer. Alexa-Fluor anti-mouse and Alexa-Fluor anti-rabbit immunoglobulin antibodies were used as secondary antibodies. The slides were washed three times and stained for nucleus detection with Hoechst 33342. Images were acquired using an Olympus FluoView™ 500 (Tokyo, Japan). Images represent grouped Z-stacks (Z=0.5 μm) from each sample.

Cell Proliferation Assessment by MTT and Apoptosis Analysis—

Cells were seeded in a 96-well plate at 5,000 cells per well in the presence of increasing concentration of WP1130 for 3 days in a $CO_2$ incubator at 37° C. 20 μL of 5 g/L 3-(4,5-dimethylthiazol-2-yl)-2,5-diphenyltetrazolium bromide (MTT) solution was added to each well for 2 h at 37° C. The cells were then lysed in 10% SDS-buffer and absorbance at 570 nm relative to a reference wavelength of 630 nm was determined with a microplate reader. The concentrations resulting in 50% inhibition of cell growth ($IC_{50}$ values) were calculated.

Annexin V and propidium iodide (PI) staining were used to measure apoptosis in WP1130 treated cells. Briefly, $10^5$/mL cells were harvested from tissue culture plates and centrifuged at 2500 rpm for 5 min at room temperature. Media supernatant was removed and cells were washed once in PBS. Cells were then resuspended in 0.4 ml of cold Annexin V binding buffer and Annexin V-FITC and propidium iodide were added. Samples were incubated at room temperature for 10 min in the dark, filtered through nylon mesh, and analyzed by flow cytometry using a FacScan analyzer (Becton-Dickinson, San Jose, Calif.).

Purified DUBs at optimal concentrations (USPS; 20 nM, UCH-L1; 20 nM, UCH-L3; 5 nM, USP9x; immunoprecipitated from 500 μg Z138 cell lysate) were incubated in DUB buffer containing WP1130, vehicle alone (DMSO) or 1 mM NEM (positive control for DUB inhibition) in a 100 μL reaction volume for 30 min. The reaction was initiated by the addition of 500 nM Ub-AMC and the release of AMC-fluorescence was recorded at ex/em 380/480 using a spectrofluorometer.

Deubiquitinase Labeling Assays—

To assay for changes in activity of cellular deubiquitinase enzymes, Z138 and HEK293 cells were lysed in DUB buffer (50 mM Tris pH 7.4, 5 mM $MgCl_2$, 150 mM NaCl) for 10 min at 4° C. The lysates were centrifuged at 20,000 RFC for 10 min and the supernatant was used for DUB labeling. Equal amounts of lysate were incubated with 500 ng of HA-UbVs for 1 hr at room temperature, followed by boiling in reducing sample buffer and resolving by SDS-PAGE. After protein transfer to nitrocellulose membranes, HA immunoblotting was used to detect DUB labeling.

Mantle cell lymphoma Z138 cells displayed high apoptotic sensitivity to WP1130 ($IC_{50}$ about 1 μM), evident by the appearance of cleaved PARP after 2-4 hours of treatment. Direct comparison of WP1130 with AG490 or bortezomib, which is clinically active in mantle cell tumors, illustrated distinctions in the apoptotic onset and activity of each compound. Like bortezomib, WP1130 displayed potent anti-proliferative properties against various other tumor cell lines of myeloid and lymphoid origin as well as HEK293 cells.

Analysis of whole cell extracts (WCE) from WP1130 treated Z138 cells showed a marked and concentration-dependent accumulation of ubiquitinated proteins. A similar increase in protein ubiquitination was seen in other WP1130 treated cells including K562, MM.1S, HeLa and HEK293. In contrast to WP1130 and the proteasome inhibitor bortezomib, Z138 cells treated with AG490 did not induce a change in cellular protein ubiquitination, even after longer incubation intervals, suggesting distinct mechanisms of action for WP1130 and its parent AG490 compound.

A time-dependent accumulation of ubiquitinated proteins into both the detergent soluble and insoluble fraction of Z138 cells was observed after WP1130 incubation. Bortezomib did not induce significant accumulation of insoluble ubiquitinated proteins, with only minimal ubiquitin content change in the detergent insoluble fraction even after 8 hours of treatment. These results suggested distinct mechanisms and downstream effectors of protein ubiquitination in WP1130 and bortezomib treated cells. Since the accumulation of ubiquitinated proteins can occur following proteasome inhibition, the impact of WP1130 on 20S proteasome activity was assessed. WP1130 incubation (5 μM, 2 hr) caused no significant decline in proteasome chymotryptic-like activity in vivo (p-value>0.07) and in vitro (p-value>0.78) while MG-132 (a known proteasome inhibitor) substantially inhibited proteasome activity in either assay. These results suggest that unlike MG-132 or bortezomib, WP1130 does not directly block 20S proteasomal activity. Oxidative stress has also been implicated in accumulation of ubiquitinated proteins. However, no increase in the generation of reactive-oxygen species in WP1130 treated cells was observed.

To further define the ubiquitin linkages accumulating in response to WP1130, HEK293T cells were transfected with plasmids expressing HA-tagged variants of ubiquitin (WT/K48Only/K63Only). Treatment of HEK293T transfectants with WP1130 showed increased accumulation of ubiquitinated proteins containing both K48- and K63-linked poly-ubiquitin chains. Proteasomal inhibition leads to the accumulation of proteins containing K48-linked ubiquitin chains, while having limited impact on K63-linked ubiquitin chains.

Aggresome Formation—

Ubiquitinated insoluble aggregates of protein are commonly associated with perinuclear structures called aggresomes. Proteasome inhibition, unfolded protein response, heat shock response or oxidative stress can lead to aggresome formation. Aggresomes are rich in HSP90/70, 20S proteasome and HDAC6 content in conjunction with poly-ubiquitinated proteins. Since a rapid accumulation of ubiquitinated proteins was noted in the detergent insoluble fraction of WP1130 treated cells, a subcellular fractionation was performed to identify the sub-cellular compartment that is enriched in ubiquitinated protein after treatment. While all cell fractions showed some change in ubiquitinated protein content, the cytoskeletal compartment of WP1130 treated cells showed marked accumulation of ubiquitinated protein conjugates. Sub-cellular fractionation studies showed the presence of aggresome marker proteins in the cytoskeletal fraction enriched in ubiquitinated proteins after WP1130 treatment. To confirm that WP1130 treatment induces formation of bona fide aggresomes, HEK293 cells were stained with key aggresome markers such as ubiquitin, DACE and 20S proteasome. Juxta-nuclear deposition of poly-ubiquitinated proteins, co-localizing with markers of aggresomes was observed in WP1130 treated cells.

WP1130 Acts as Deubiquitinase Inhibitor—

Inhibition of cellular deubiquitinases could lead to an increase in high molecular weight ubiquitinated proteins in the absence of proteasome inhibition. A rapid depletion of monomeric ubiquitin was observed in Z138 cells treated with 5 µM WP1130 over 2 hours and a subsequent increase in the levels of unanchored/free polyubiquitin chains ($Ub_{4-5}$) in cells treated with WP1130. In contrast, bortezomib treatment did not significantly affect the level of free ubiquitin or unanchored ubiquitin chains. This observation suggests that WP1130 may reduce ubiquitin recycling and amass ubiquitinated proteins through inhibition of deubiquitinase activity. To directly assess the impact of WP1130 on DUB activity in treated cells, cell lysates from control and treated cells were incubated with ubiquitin-AMC and fluorescence generated as a consequence of substrate cleavage was measured as an indicator of DUB activity. Z138 cells were treated with 5 µM WP1130, 50 nM bortezomib, 1 mM NEM or untreated for 1, 2, or 4 hours before extracts (5 µg) were incubated with fluorogenic substrate. Treatment with WP1130 significantly reduced DUB activity in Z-138 cells by nearly 50% by 4 hours (p-value 0.0095). Interestingly, no change in DUB activity in bortezomib treated cells was observed, while NEM (a known DUB inhibitor) suppressed cellular DUB activity by 80% within 1 hr.

The effect of WP1130 treatment on in vitro deubiquitination/disassembly of purified K48-linked or K63-linked polyubiquitin chains was evaluated. Lysates from WP1130 treated (2 hr) or untreated cells were incubated with 1 µg of unanchored polyubiquitin chains for 5, 10 and 15 min at 37° C. Lysates from untreated cells displayed an almost complete disassembly of polyubiquitin chains in contrast to the limited disassembly observed with lysates from WP1130 treated cells. Lack of chain disassembly of both K48- and K63-linked polyubiquitin chains from the lysates of WP1130 treated cells is in agreement with previous observations of increased accumulation of both types of ubiquitin linkages upon WP1130 treatment. These results suggest that WP1130 treatment inhibits cellular DUB enzyme/s required for the breakdown of both K48- and K63-specific ubiquitin linkages.

WP1130 Inhibits Deubiquitinase Enzymes In Vitro—

Hemagglutinin-tagged ubiquitin vinyl methyl sulfone (HA-UbVs) acts as a DUB suicide substrate, forming a covalent adduct with active DUB enzymes. Specific cellular DUBs can be identified by anti-HA blotting, as previously shown in various cell types. Changes in specific DUB activities are measurable by monitoring HA-labeling in lysates from control and treated cells. Z138 cells were treated with WP1130 at 1, 5, or 10 µM or AG490 at 250 µM for 1 hours and lysed. 20 µg of clarified supernatant was incubated with 200 nM of HA-UbVS for 1 hr at 37° C. A dose-dependent and time reduction in the labeling of DUBs representing USP9x, USPS, USP14 and UCH37 was seen in cells treated with WP1130. In contrast, no change in DUBs labeling was noted in cells treated with AG490, confirming distinctions in the activity and mechanism of action of the parental tyrphostin and WP1130. An in vitro analysis using cell lysates was performed to investigate direct DUB inhibition by WP1130. Briefly, untreated Z138 cell lysates were incubated with 5 µM WP1130 or vehicle alone for one hour at 37° C., followed by labeling with HA-UbVs. Incubation of cell lysate with WP1130 showed a reduction of HA-labeling of the same DUBs as those noted in intact cells, suggesting that WP1130 caused direct DUB inhibition.

To determine whether WP1130 directly inhibits DUB activity, purified DUBs such as USP5, UCH-L1 and UCH-L3 were incubated with vehicle alone or WP1130 for 30 min in DUB buffer at 37° C. USP9x was immunoprecipitated from Z138 cell lysates, prepared in DUB buffer and the beads were incubated with vehicle alone or WP1130 for 30 min. Ub-AMC (500 nM) was added to each reaction and fluorescence was monitored every minute for up to 30 minutes. The maximum fluorescence observed at the end of the linear phase of substrate cleavage in control and WP1130 treated DUBs was used as a gauge to estimate DUB activity and % inhibition. Treatment with 5 µM WP1130 reduced the activities of USP9x, USP5 and UCH-L1 by 80% or more. No inhibition was observed against UCH-L3 activity, suggesting that WP1130 may be partly selective. The loss of USP5 activity was confirmed using HA-UbVs labeling, which demonstrated about 80% reduction in HA labeling upon incubation with WP1130.

DUBs Modulate Pro- and Anti-Apoptotic Protein Levels—

USP5 is known to play a major role in maintaining the levels of unanchored polyubiquitin chains. Loss of USP5 has been reported to stabilize p53, due to the accumulation of free polyubiquitin chains which compete with ubiquitinated p53. There is a positive correlation between the increased levels of MCL-1 and USP9x in lymphomas and other tumors. siRNA mediated knockdown of USP9x led to rapid degradation of MCL-1, and sensitization of tumor cells to apoptotic stimuli.

An increase in p53 protein levels was observed upon WP1130 treatment. Co-treatment of Z138 cells with cycloheximide (50 µg/mL) and WP1130 confirmed the stabilization rather than induction of p53 protein. Furthermore, a rapid decline in MCL-1 levels upon WP1130 treatment was observed. To re-confirm the role played by USP9x and USP5 in regulating the levels of MCL-1 and p53 respectively, a siRNA based knockdown of USP9x and USP5 in HEK293T cells was performed. Loss of USP9x led to about 50% decline in MCL-1 levels while loss of USP5 showed about 2-fold increase in p53 levels. Together these results demonstrate that WP1130 inhibits selective cellular DUB activities, modulating the stability of both anti- and pro-apoptotic proteins.

DUB Inhibition by WP1130 Induces Apoptosis—

WP1130 contains α,β-unsaturated carbonyl group that can hypothetically interact with sulfhydryl of cysteines found in the active sites of DUBs through a Michael addition reaction (see, e.g., Straus, et al., *Medicinal Research Reviews*, 21:185-210 (2001)). However, similar carbonyl groups are found in AG490 but this molecule possesses no apparent DUB inhibitory activity in cells. Z138 cells were incubated with WP1130 at 0.3-5 µM, in the presence and absence of 1 mM DTT. Interestingly, a complete loss of WP1130-induced apoptosis and its associated anti-proliferative effects was observed in the presence of DTT. This observation correlates with the loss of induced ubiquitination and DUB inhibition by WP1130 in the presence of DTT. The loss of WP1130-induced apoptosis and DUB inhibitory activity in the presence of DTT suggests that suppression of active DUBs by WP1130 directly accounts for the apoptotic effects of WP1130.

WP1051 and WP1052 represent two earlier chemical analogues of WP1130. While WP1051 was effective in suppressing tumor cell proliferation (although at high doses than WP1130), WP1052 failed to show any anti-tumor properties. This was unexpected as WP1051 and WP1052 are chemically identical but structurally distinct isomers. Since apoptosis/anti-proliferative properties of WP1130 are related to its ability to suppress cellular DUBs and induce accumulation of ubiquitinated proteins, WP1051 and 1052 were investigated whether they can affect protein ubiquitination and DUB activity. Treatment of Z138 cells with the indicated concentrations of WP1051 and 1052 showed that while WP1051 can induce accumulation of ubiquitinated proteins in a dose-dependent fashion, WP1052 failed to show any affect on ubiquitinated proteins. The DUB labeling profile in lysates from cells treated with WP1051 or WP1052 were investigated and observed that while WP1051 could suppress the activity of a DUB corresponding to USP9x, WP1052 showed no DUB inhibition. These results demonstrate that DUB inhibition by this class of compounds exhibit a precise chemical structure-activity relationship.

Antiviral Activity of DUB Inhibitors

MNV replicates readily in primary or cultured murine macrophages and dendritic cells. In efforts to identify MNV entry inhibitors, ongoing investigation into the specific kinase(s) involved led to WP1130, an inducer of Jak2 kinase trafficking, and the chemically related compounds WP1051 and WP1052.

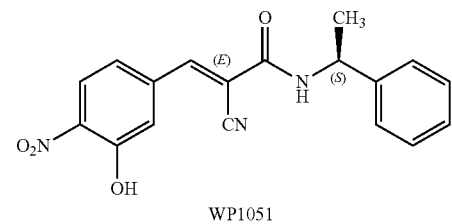

WP1051

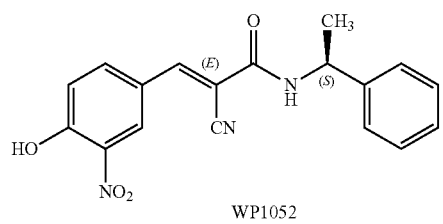

WP1052

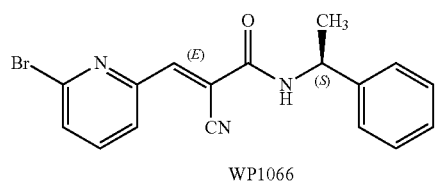

WP1066

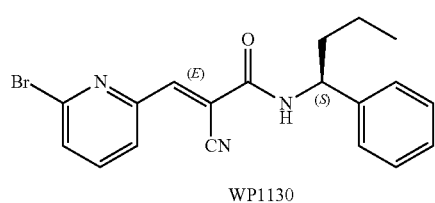

WP1130

Pre-treatment of MNV-1 infected RAW 264.7 cells with WP1130 or WP1051, but not the structurally-related WP1052 compound, reduced viral titers 8 and 12 hours postinfection (hpi) without affecting cell viability. RAW 264.7 cells were plated and allowed to attach overnight. The next day culture media was aspirated and replaced with media containing inhibitors (5 μM WP1130, 20 μM WP1052, or 20 μM WP1051) or DMSO vehicle control (no treat). After 30 minutes of preincubation at 37° C., cells were infected with MNV-1 (MOI 5) on ice. Virus was removed and compounds reapplied for 8 or 12 hours. Viral titers were determined by plaque assay. Cell viability remained above 80% as determined by WST-1 (Roche). This level of inhibition (about 2 logs) of MNV-1 infection is similar to the inhibition seen in RAW 264.7 cells pre-treated with high doses of IFNα (1000 U/ml), a known and highly potent antiviral molecule. The life cycle of MNV-1 is estimated to be between 9 and 12 hours.

WP1130 Reduces Norwalk Virus (NV) Replication in a Replicon System

No robust cell culture system is available to study human norovirus infection, including Norwalk virus. Therefore, to study NV replication in cells and identify antivirals against the fastidious human noroviruses, NV replicon-bearing cells were developed. Briefly, plasmid NV101, which contains a cloned cDNA consensus sequence of the RNA genome of NV, was engineered to encode the neomycin resistance gene within ORF2, the major capsid protein. The resulting plasmid was designated pNV-Neo. RNA transcripts from pNV-Neo were transfected into Huh-7. Viable cell colonies were selected in the presence of G418 and designated as HG23 cells. Expression of full length genomic and subgenomic NV RNA species (sense and anti-sense) and non-structural proteins was confirmed by Northern blot analysis and immunofluorescence assay and Western blot analysis, respectively. Using the replicon-haboring cells, WP1130 was examined for anti-NV effects. HG23 cells were treated with 5 μM WP1130 to examine its effects on NV replication. Interferon (IFN)-alpha, a potent antiviral molecule, was used in this study as a positive control. At 48 hr post-treatment, NV genome was analyzed with qRT-PCR. Total RNA was prepared for quantitative real time PCR to detect NV genome and β-actin. The reduction of NV genome by the inhibitor was calculated compared to that with mock-treatment and afterwards each genome level was normalized to the level of β-actin. The non-specific cytotoxic effects on HG23 cells by WP1130 were monitored using the cell cytotoxicity assay kit (AnaSpec, San Jose, Calif.). WP1130 showed a significant anti-NV effect in HG23 cells at 5 μM similar to the level seen for IFNα. However, compound associated cytotoxicity in HG23 cells was observed only at concentrations higher than 10 μM. Thus, WP1130 has antiviral activity against murine and human noroviruses, a group of viruses for which no antiviral drugs are currently available.

WP1130 has Broad Antiviral Activity

Based on the data that WP1130 blocked norovirus replication, it was investigated whether it also exhibited broader antiviral activity. Using a range of viruses with RNA genomes, WP1130 was shown to also block infection of encephalomyocarditis virus (EMCV), Sindbis virus (SiNV), La Crosse virus (LaCV) but not Vesicular Stomatitis Virus (VSV). EMCV is a (+)-sense RNA virus in the picornavirus family, the most closely related virus family to caliciviruses (including noroviruses). Sindbis virus is a (+)-sense RNA viruses in the Togavirus family (related to the Eastern/Western/Venezuelan equine encephalitis viruses found in the Americas). The category B La Crosse virus and Vesicular Stomatitis Virus are RNA viruses with a (−) sense genome that are members of the Bunyavirus family (e.g. hantaviruses, Rift valley fever virus, Crimean-Congo Hemorrhagic fever virus) and Rhabdovirus family (e.g. Rabies virus), respectively. While the polarity of the viral genome does not appear to determine the effectiveness of WP1130, this data demonstrates the broad antiviral potential of WP1130. More importantly, WP1130 is active against members of virus families containing category A (hantavirus, rift valley fever virus), B (Eastern/Western/Venezuelan equine encephalitis viruses), and C (Rabies, Crimean-Congo Hemorrhagic fever virus) agents.

WP1130 Anti-Bacterial Activity

*Listeria monocytogenes* is a Gram-positive rod-shaped bacterium that causes potentially fatal listeriosis after consumption of contaminated food. It is a facultative intracellular pathogen that infects non-phagocytic and phagocytic cells, including the murine macrophage cell line RAW 264.7. Intracellular replication occurs after bacteria escape from phagosomes. Because of its intracellular life style, WP1130 was tested for its effectiveness against this food-borne pathogen. Murine macrophages were infected with *L. monocytogenes* after pre-treatment with WP1130 or treated with this compound after infection as a control. RAW 264.7 cells were plated and allowed to attach overnight. Culture media was aspirated the next day and replaced with media containing 5 µM WP1130 or DMSO vehicle control. After 30 minutes of preincubation at 37° C., cells were infected with *L. monocytogenes* strain 10403S (MOI 1) for 30 minutes at 37° C. Cells were washed three times in PBS and media containing 10 µg/ml Gentamicin and WP1130 was added back to the cells. For post-treatment, WP1130 was applied 1 hour after infection. At eight hours post-infection, RAW 264.7 cells were lysed in sterile water and bacteria plated onto growth media plates. Colony forming units (CFUs) were determined after 24 hour incubation at 37° C. and normalized to the vehicle control. Cell viability remained above 80% as determined by WST-1 (Roche). Significantly fewer bacteria were able to grow when cells were pre-treated with WP1130 compared to vehicle control or post-treatment. Interestingly, WP1130 treatment 1 hour postinfection did not lead to a decrease in colony forming units, indicating the compound affects an early time point during the *Listeria* life cycle. These data demonstrate that in addition to its antiviral activity, WP1130 has anti-bacterial properties, making it a good candidate for a broad spectrum antimicrobial agent.

WP1130 Anti-Parasitic Activity

*Toxoplasma gondii* is a species of parasitic protozoa and is the causative agent of toxoplasmosis. Current medications to prevent and treat toxoplasmosis exhibit limited efficacy and potentially serious side effects. *T. gondii* is an obligate intracellular pathogen that infects virtually any nucleated cell. The parasite has two forms, tachyzoite and bradyzoites. Haploid tachyzoites rapidly divide and reversibly transform into latent bradyzoites to produce intracellular tissue cysts, the hallmark of chronic infections. During infection, *Toxoplasma* creates a subcellular compartment called a parasitophorous vacuole that serves as a platform for modulating host cell functions. Thus, WP1130 was tested for its anti-parasitic function.

Primary human foreskin fibroblasts (HFF) were infected with trachyzoites in the presence of WP1130 or vehicle control for 24 hours. HFF cells were plated and allowed to attach overnight. The next day the culture media was aspirated and replaced with media containing 5 µM WP1130 or DMSO vehicle control. 1.25×10$^5$ tachyziotes (RH strain) (MOI=1) were added to each well of a chamber slide in the presence of WP1130 or vehicle control. At 24 hours post infection, cells were fixed in 4% paraformaldehyde for fifteen minutes. Cells were then washed with PBS and analyzed by immunofluorescence microscopy. Parasites were stained with an anti-SAG 1 antibody (the immunodominant surface antigen of *T. gondii*) followed by an Alexa 594-labeled secondary antibody and DAPI. For quantitative analysis the number of parasites/vacuole were counted. Immunofluorescence analysis of infected cells showed that WP1130 significantly reduced the number of parasites per vacuole, demonstrating WP1130 blocks parasite replication. Together these data demonstrate that WP1130 exhibits antimicrobial activity in multiple different cell types, including primary cells, and against a diverse range of pathogens.

Anti-Viral Activity of WP1130 Derivative

RAW 264.7 cells or primary bone marrow derived macrophages from Swiss Webster mice were plated and allowed to attach overnight. The next day culture media was aspirated and replaced with media containing inhibitors (5 µM WP1130 or 5 µM WPDTT) or DMSO (vehicle control). Cells were treated with IFN-β as a positive anti-viral control. After 30 minutes of preincubation at 37° C., cells were infected with MNV-1 (MOI 5) on ice. Virus was removed and compounds reapplied for 8 or 12 hours. Similar reductions in viral titers were seen with WPDTT as compared to WP1130.

WP1130 Antiviral Activity Without Host Cytotoxicity

RAW 264.7 cells were pre-treated with increasing concentrations of WP1130 prior to MNV-1 infection. Viral titers and cell viability (WST-1 viability assay, Roche) were compared 12 hours postinfection for each concentration. The anti-viral $EC_{50}$ activity was estimated at 1.9 µM while the $IC_{50}$ for viability was estimated to be 7.6 µM. These values were used to calculate a therapeutic index of about 4.0.

WP1130 Increases Protein Ubiquitination and Reduces Usp9x DUB Activity

RAW 264.7 cells were treated with 5 µM WP1130 for 2 hours before assessing ubiquitinated protein levels by immunoblotting equal protein cell lysates (20 µg) resolved by SDS-PAGE and probed with anti-ubiquitin. RAW264.7 cells were incubated with 5 µM WP1130 or vehicle alone (Control) for 2 hours before cell lysates were prepared and incubated with HA-UbVS (200 ng) for an additional hour. HA blotting was used to detect DUB activity. The membrane was subsequently blotted for Usp9x. The results demonstrate Usp9x inhibition by WP1130 incubation in RAW264.7 cells. HEK293 lysates were also subjected to immunoblotting for Usp9x.

WP1130 Inhibits MNV-1 Infection-Induced DUB Activity

RAW 264.7 cells were left untreated or treated with the indicated concentration of WP1130 for 2 hours before cells were mock infected or MNV-1 infected (MOI=5). Cells were incubated at 37° C. for an additional 2 hours before cell lysates were prepared and incubated with HA-UbVS (200 ng) for an additional hour. HA blotting was used to detect DUB activity. The activity of several DUBs was increased by MNV-1 infection. The results also demonstrate that anti-viral effective WP1130 concentrations block DUB activity induced by MNV-1 infection. Lower concentrations of WP1130 (1.25 µM) were ineffective in blocking MNV-1 or DUB activation associated with MNV-1 infection. These results suggest that WP1130 anti-viral activity was associated with blocking DUB activation induced by MNV-1 infection.

Chemical Synthesis Routes

The compounds disclosed herein can be prepared by any means readily available to the ordinarily skilled chemist. A suggested route for some of the compounds is shown below in the following schemes, and the ordinarily skilled artisan can readily modify these synthetic schemes to arrive at the compounds described herein.

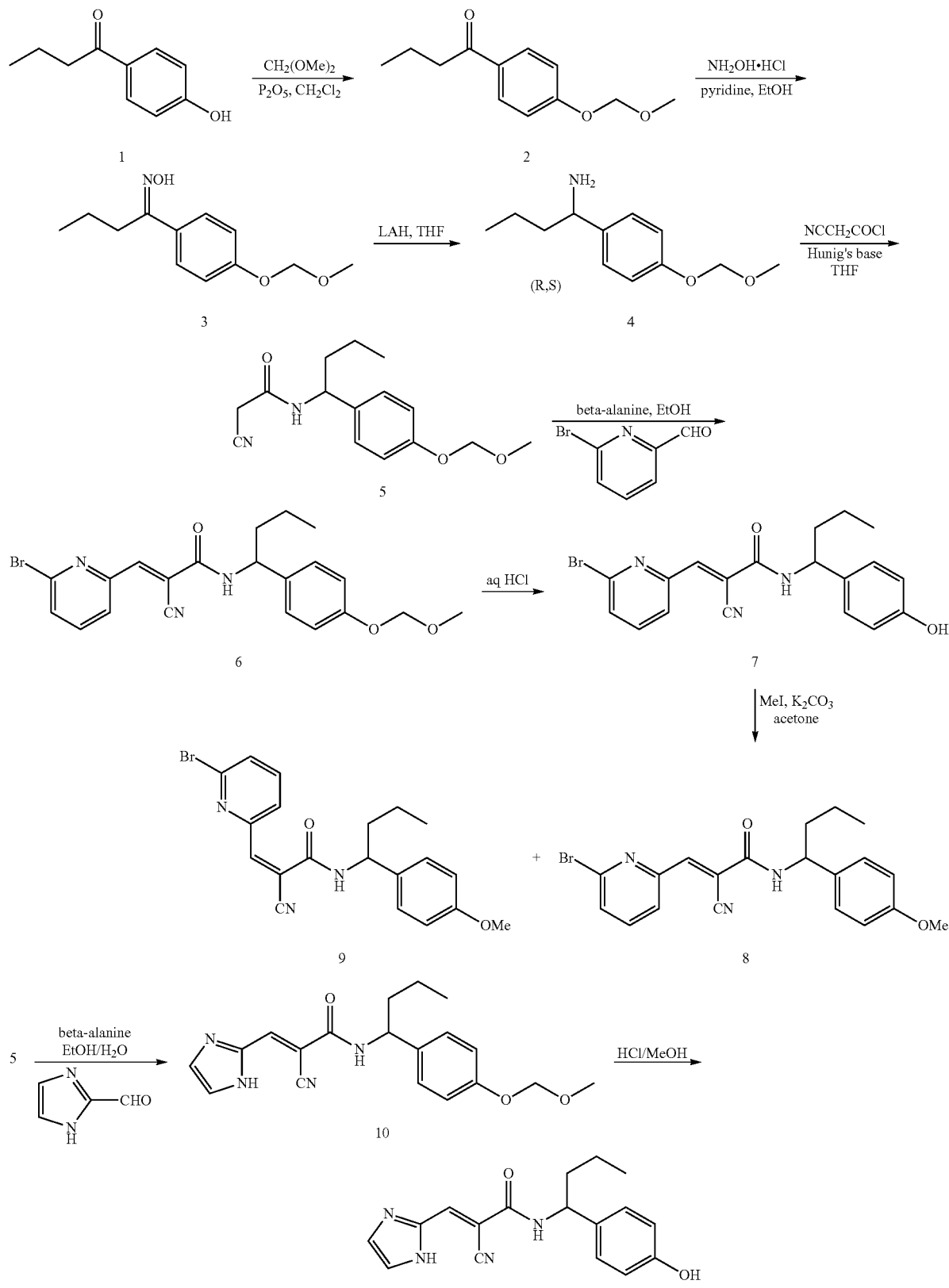

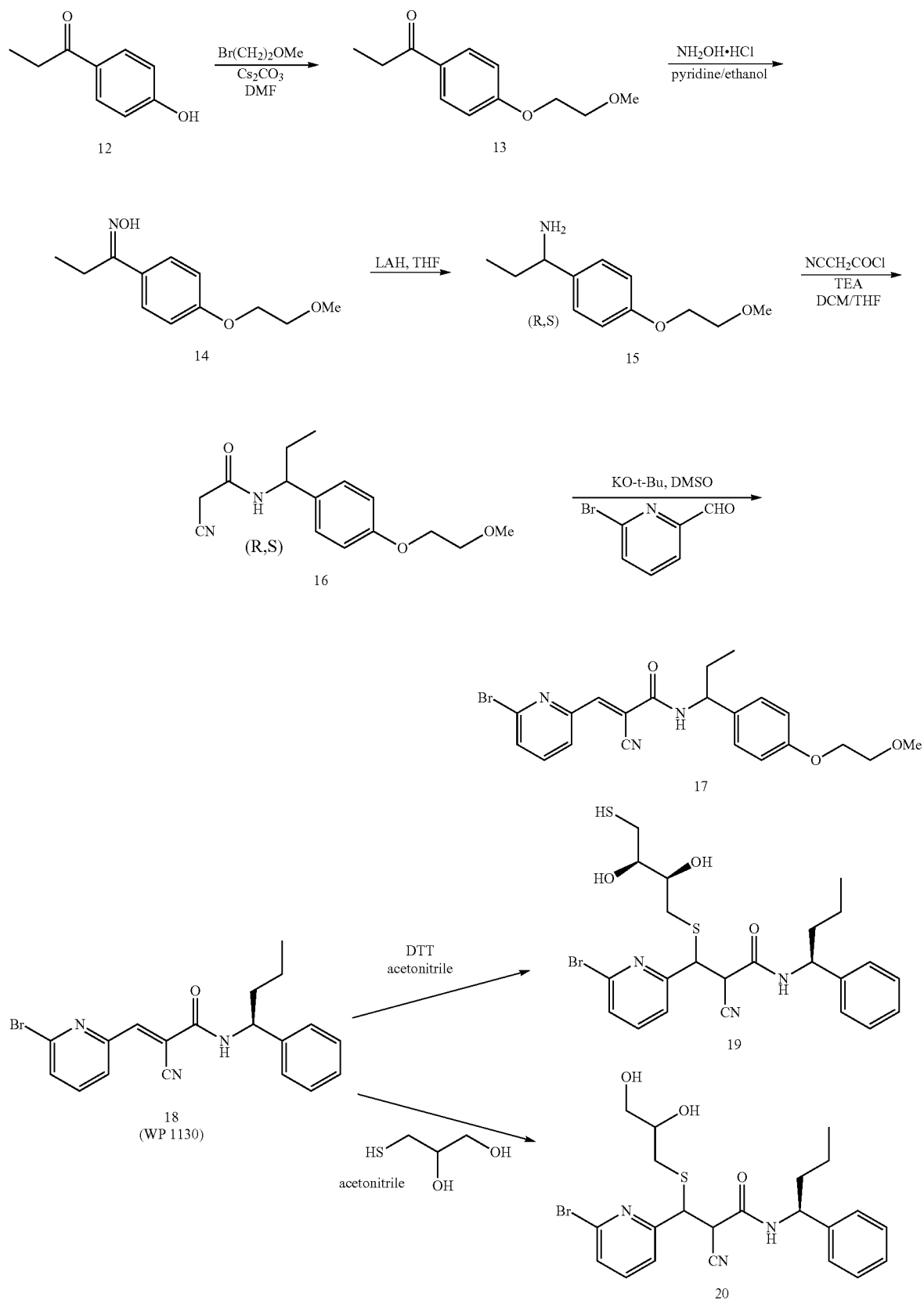
Scheme 2

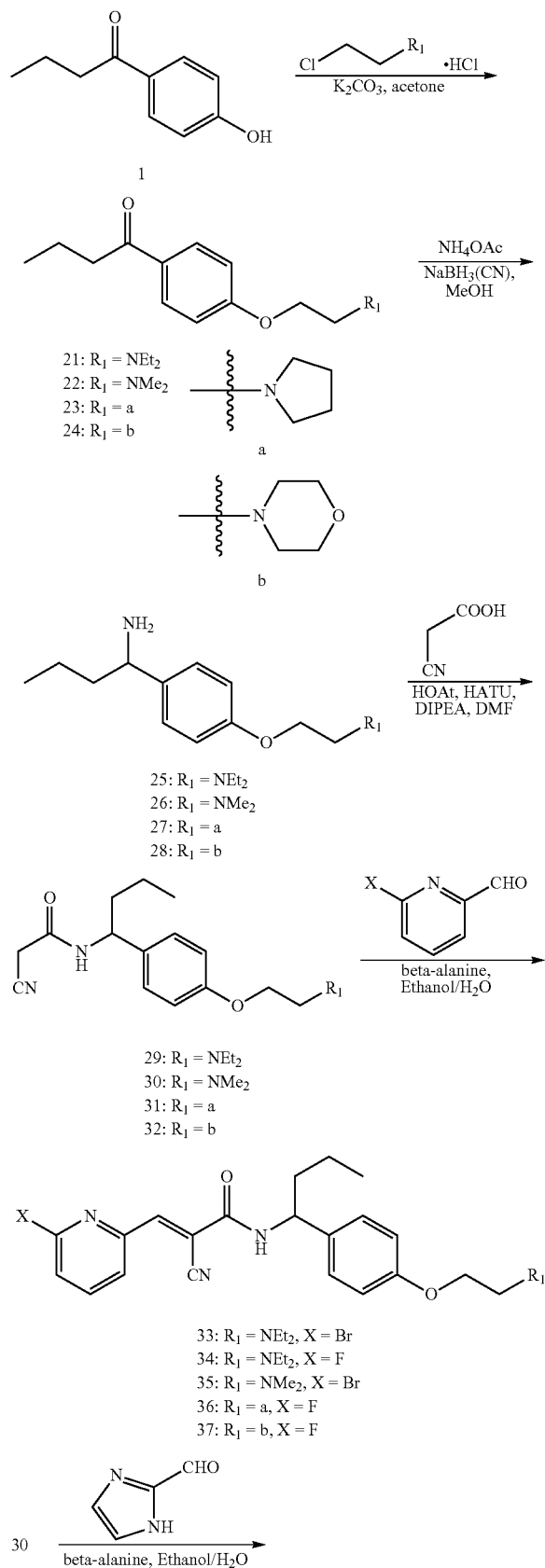

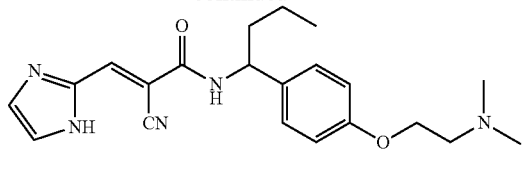

38

1-(4-(Methoxymethoxy)-phenyl)butan-1-one (2)

Phosphorus pentoxide (21.6 g, 152 mmol) was added to a stirred solution of methylal (41.7 g, 548 mmol) and 4-hydroxybutyrophenone (1; 5.0 g, 30.5 mmol) in dichloromethane (180 mL) under nitrogen at room temperature. After 48 hours the mixture was poured into ~500 mL of ice-cold 2M aq sodium carbonate and stirred well. The aq. layer was reintroduced to the reaction flask to react with the dark residual sludge (foaming), then recombined with the workup mixture. After thorough mixing, the layers were allowed to separate. The organic layer was drawn off and the aq layer extracted with a small amount of dichloromethane. The combined extracts were washed with water then saturated brine and dried over magnesium sulfate. The solvent was removed in vacuo to afford 5.7 g of clear amber oil. The product was flash chromatographed on a column (35×75 mm) of silica gel, eluting with Hxa/EtOAc/acetone 8:1:1 to afford 4.1 g (65%) of thin, clear colorless oil; homogeneous by TLC, $R_f$=0.40 plus 1 g of clear yellow oil of slightly lesser purity

1-(4-(Methoxymethoxy)phenyl)butan-1-one oxime (3)

Hydroxylamine hydrochloride (2.7 g, 39.4 mmol) was added to a stirred solution of 1-(4-(methoxymethoxy)-phenyl)butan-1-one (4.1 g, 19.7 mmol) and pyridine (94.67 g, 59.1 mmol) in ethanol (30 mL), and the mixture heated to reflux for 1.5 hours then allowed to cool. Most of the ethanol was removed by concentration under reduced pressure, and the residue was partitioned between water and dichloromethane. The layers were separated and the aq phase extracted 2× with dichloromethane. The combined extracts were washed twice with water, then with saturated brine and dried over magnesium sulfate. The solvent was removed in vacuo, leaving 5.1 g of slightly cloudy, colorless syrup, which was flash chromatographed on a column (50×70 mm) of silica gel eluting with Hxa/EtOAc/acetone 8:1:1 to afford 3.4 g (77%) of snow-white crystalline solid; mp 74-76° C.

1-(4-(Methoxymethoxy)phenyl)butan-1-amine (4)

A solution of 1-(4-(methoxymethoxy)phenyl)butan-1-one oxime (3.4 g, 15.2 mmol) in tetrahydrofuran (50 mL) was added drop-wise to a stirred suspension of lithium aluminum hydride (1.83 g, 45.7 mmol) in tetrahydrofuran (100 mL) at room temp under nitrogen. After the initial foaming subsided the mixture was gradually heated to reflux. After 7 hours under reflux the mixture was allowed to cool, and an additional 1.0 g of lithium aluminum hydride was added to the mixture, which was reheated at reflux for 4 hours and then again allowed to cool. An additional 0.2 g of lithium aluminum hydride was added and the mixture was reheated at reflux for 1 hour and then allowed to cool. 3 mL of water was added drop-wise, followed by 3 mL of 15% aq sodium hydroxide, and then 9 mL of water. After stirring until the precipitate was well-granulated, the mixture was filtered and the residue washed twice with tetrahydrofuran. The filtrate/washings were concentrated in vacuo and the residue dissolved in dichloromethane and dried over magnesium sulfate. The solvent was removed in vacuo, leaving 2.9 g of purplish syrupy residue, which was flash chromatographed on a column (50×90 mm) of silica gel, eluting with Hxa/EtOAc/acetone 8:1:1 to afford 0.4 g of pure product as a clear golden oil, plus 1.4 g (57% total) of material of slightly lesser purity.

2-Cyano-N-(1-(4-(methoxymethoxy)phenyl)butyl)acetamide (5)

Oxalyl chloride (1.03 g, 8.15 mmol) was added drop-wise at ice bath temperature under nitrogen to a stirred solution of cyanoacetic acid (0.67 g, 7.9 mmol) in tetrahydrofuran (15 mL) to which 1-2 drops of DMF had been added. The mixture was stirred for an hour, then added slowly in one portion to a stirred solution of 1-(4-(methoxymethoxy)phenyl)butan-1-amine (1.1 g, 5.3 mmol) in THF (15 mL) at ice bath temperature under nitrogen. The mixture was allowed to warm gradually to room temperature and after 20 hours was stirred into 50 mL of saturated aq sodium bicarbonate and extracted 3× with dichloromethane. The combined extracts were washed with saturated brine, dried over magnesium sulfate, and concentrated in vacuo, leaving 1.5 g of dark violet syrup. The product was flash chromatographed on a column (50×70 mm) of silica gel (43-60 μm) eluting with Hxa/EtOAc 1:1 to afford 1.0 g (69%) of clear, dark oil; homogeneous by TLC.

(E)-3-(6-Bromopyridin-2-yl)-2-cyano-N-(1-(4-(methoxymethoxy)phenyl)butyl)acrylamide (6)

β-Alanine (1.42 g, 16 mmol) and 6-bromopyridine-2-carboxaldehyde (744 mg, 4 mmol) were added successively to a stirred solution of 2-cyano-N-(1-(4-(methoxymethoxy)phenyl)butyl)acetamide (276 mg, 1.0 mmol) in ethanol/water (28 mL/17 mL) at room temp. After 72 hours TLC (in 25% EtOAc/Hexane) showed a single product and some starting materials. The mixture was partitioned between aqueous sodium bicarbonate and ethyl acetate. The separated organic layer was washed with sat. brine and dried with sodium sulfate and concentrated to give a light amber oil (830 mg) as crude product. The crude material was purified by flash chromatography to afford the title compound as a yellow oil (253 mg) in 57% yield. $^1$H NMR (500 MHz, CDCl$_3$) δ 7.59 (dd, J=7.9, 7.5 Hz, 1H), 7.52 (d, J=8.0 Hz, 1H), 7.27 (d, J=8.6 Hz, 2H), 7.22 (d, J=7.4 Hz, 1H), 6.96 (d, J=8.6 Hz, 2H), 6.82 (s, 1H), 5.19 (s, 2H), 3.85 (t, J=7.6 Hz, 1H), 3.49 (s, 3H), 1.67 (m, 2H), 1.39 (m, 2H), 0.94 (t, J=7.3 Hz, 3H); Mass spec ES+; m/z=444.0 (m+1) and 466.0 (m+Na$^+$).

(E)-3-(6-Bromopyridin-2-yl)-2-cyano-N-(1-(4-hydroxyphenyl)butyl)acrylamide (7)

3-(6-bromopyridin-2-yl)-2-cyano-N-(1-(4-(methoxymethoxy)phenyl)butyl)acrylamide (14 mg, 0.031 mmol) was dissolved into HCl/MeOH (1.25 M, 2 mL). This solution was stirred at room temperature for 18 hours. TLC (in 50% EtOAc/Hexane) showed a single product. The mixture was partitioned between aqueous sodium bicarbonate and ethyl acetate. The separated organic layer was washed with sat. brine and dried with sodium sulfate and concentrated to give a light amber solid (20 mg) as crude product. The crude material was purified by preparative TLC to afford the title compound as a light yellow solid (12 mg) in 95% yield. $^1$H NMR (500 MHz, CDCl$_3$/CD$_3$OD) δ 7.55 (dd, J=7.8, 7.5 Hz, 1H), 7.48 (d, J=8.0 Hz, 1H), 7.18 (d, J=7.4 Hz, 1H), 1H), 7.07 (d, J=7.4 Hz, 2H), 6.78 (s, 1H), 6.68 (d, J=8.3 Hz, 1H), 3.78 (t, J=7.6 Hz, 1H), 1.62 (m, 2H), 1.34 (m, 2H), 0.88 (t, J=7.3 Hz, 3H). $^1$H NMR (500 MHz, CDCl$_3$/CD$_3$OD) δ 161.9, 157.2, 151.4, 142.0, 140.8, 139.0, 131.9, 129.4, 128.9, 124.5, 116.5, 115.8, 115.2, 49.5, 29.2, 20.09, 13.7; Mass spec ES+; m/z=422 (m+Ma$^+$); mp (195° C. decomposition starts). Elemental analysis: C=56.73%, H=4.51%, N=10.33%. (calc: C=57.01%, H=4.53%, N=10.50%).

3-(6-Bromopyridin-2-yl)-2-cyano-N-(1-(4-methoxyphenyl)butyl)acrylamide (8 and 9)

To a solution of 3-(6-bromopyridin-2-yl)-2-cyano-N-(1-(4-hydroxyphenyl)butyl)acrylamide (21 mg, 0.05 mmol) in acetone was added MeI (32.6 μL, 0.52 mmol) and potassium carbonate powder (7.25 mg, 0.05 mmol). The resulting mixture was stirred at room temperature for 4 hours before the addition of ethyl acetate. The organic solution was then washed with water (1×), saturated brine (1×), dried over sodium sulfate and concentrated to give a yellow oil as the crude product. The crude material was purified with preparative TLC plate to afford (E)-3-(6-bromopyridin-2-yl)-2-cyano-N-(1-(4-methoxyphenyl)butyl)acrylamide (8) as a light yellow solid (9.2 mg, 42% yield) and (Z)-3-(6-bromopyridin-2-yl)-2-cyano-N-(1-(4-methoxyphenyl)butyl)acrylamide (9) as a white solid (4.4 mg, 20% yield). Mass spec ES+, m/z=414.0 (m+H$^+$). E-isomer (8): $^1$H NMR (500 MHz, CDCl$_3$/CD$_3$OD) δ 7.59 (t, J=7.7, 1H), 7.52 (d, J=8.0, 1H), 7.27 (d, J=8.7, 2H), 7.22 (d, J=7.4, 1H), 6.83 (d, J=8.9, 2H), 6.81 (s, 1H), 3.89-3.83 (m, 2H), 3.81 (s, 3H), 1.65 (dd, J=15.4, 7.9, 2H), 1.39 (dd, J=15.1, 7.5, 2H), 0.94 (t, J=7.4, 3H). Z-isomer (9): $^1$H NMR (500 MHz, CDCl$_3$) δ 7.83 (s, 1H), 7.79 (d, J=7.6, 1H), 7.61 (t, J=7.8, 1H), 7.52 (d, J=7.9, 1H), 7.15 (d, J=8.8, 2H), 6.93 (d, J=8.8, 2H), 3.84 (s, 3H), 3.84-3.79 (m, 2H), 1.57 (dd, J=14.8, 7.1, 5H), 1.37 (dq, J=15.0, 7.5, 2H), 0.94 (t, J=7.4, 3H).

(E)-2-Cyano-3-(1H-imidazol-2-yl)-N-(1-(4-(methoxymethoxy)phenyl)butyl)acrylamide (10)

β-Alanine (71.3 mg, 0.8 mmol) and 1H-imidazole-2-carbaldehyde (19.2 mg, 0.2 mmol) were added successively to a stirred solution of 2-cyano-N-(1-(4-(methoxymethoxy)phenyl)butyl)acetamide (5; 27.6 mg, 0.1 mmol) in ethanol/water (2.0 mL/0.8 mL) at room temp. After 72 hours TLC (in 50% EtOAc/Hexane) showed a single product formed. The mixture was partitioned between aqueous sodium bicarbonate and ethyl acetate. The separated organic layer was washed with sat. brine and dried with sodium sulfate and concentrated to give a light amber oil (55 mg) as crude product. The crude material was purified by column chromatography to afford the titled compound as a yellow oil (23 mg) in 65% yield. $^1$H NMR (500 MHz, CDCl$_3$) δ 10.59 (s, 1H), 8.14 (s, 1H), 7.42 (s, 1H), 7.23 (s, 1H), 7.17-7.13 (m, 2H), 7.12-7.07 (m, 2H), 5.22 (s, 2H), 3.86-3.75 (m, 2H), 3.51 (s, 3H), 1.64-1.53 (m, 2H), 1.36 (m, 2H), 0.93 (t, J=7.3, 3H). Mass spec ES+, m/z=355.1 (m+H$^+$).

(E)-2-Cyano-N-(1-(4-hydroxyphenyl)butyl)-3-(1H-imidazol-2-yl)acrylamide (11)

(E)-2-cyano-3-(1H-imidazol-2-yl)-N-(1-(4-(methoxymethoxy)phenyl)butyl)acrylamide (14.8 mg, 0.041 mmol) was dissolved into HCl/MeOH (1.25 M, 2 mL). This solution was stirred at room temperature for 18 hours. TLC showed a single product. The mixture was partitioned between aqueous sodium bicarbonate and ethyl acetate. The separated organic layer was washed with sat. brine and dried with sodium sulfate and concentrated to give a light amber solid (9 mg) as crude product. The crude material was recrystallized from ethyl acetate/hexanes to afford the titled compound as a light yellow solid (6 mg) in 46% yield. $^1$H NMR (500 MHz, CDCl$_3$/CD$_3$OD) δ 7.84 (m, 1H), 7.28 (m, 1H), 7.18 (s, 1H), 6.99 (d, J=6.8, 2H), 6.82 (d, J=7.8, 2H), 3.73 (m, 2H), 1.53 (m, 2H), 1.30 (m, 2H), 0.88 (t, J=7.1, 3H). Mass spec ES+, m/z=311.1 (m+H$^+$).

1-(4-(2-Methoxyethoxy)phenyl)propan-1-one (13)

Cesium carbonate (5.7 g, 17.5 mmol) was added to a stirred solution of 4-hydroxypropiophenone (12; 2.5 g, 16.7 mmol) in dimethylformamide (25 mL) under nitrogen at room temperature, followed by bromomethyl methyl ether (1.43 g, 17.5 mmol). After 20 hours the mixture was stirred into 200 mL of water, and then extracted 3× with dichloromethane. The combined extracts were washed with water and then sat brine, and dried over magnesium sulfate. The solvent was removed in vacuo, leaving 3.4 g of pale yellow apparently crystalline solid; mp 31-35° C.; mass spec ES+m/z=209 (m+1).

1-(4-(2-Methoxyethoxy)phenyl)propan-1-one oxime (14)

Hydroxylamine hydrochloride (2.27 g, 32.7 mmol) was added to a stirred solution of 1-(4-(2-methoxyethoxy)phenyl)propan-1-one (3.4 g, 16.3 mmol) and pyridine (3.87 g, 49.0 mmol) in ethanol (25 mL) and the mixture heated at reflux for 4 hours then allowed to cool. Most of the ethanol was removed by concentration, and the residue was partitioned between water and dichloromethane. The layers were separated and the aqueous phase extracted 2× with dichloromethane. The combined extracts were washed twice with water, then with sat brine and dried over magnesium sulfate. The solvent was removed by concentration, and then the residue was dissolved in toluene and again concentrated; this process was repeated once more, and the residue was dried under in vacuo to afford 3.52 g of the product as a cream-colored crystalline solid; mp 74-80° C.; mass spec ES+m/z=224 (m+1).

1-(4-(2-Methoxyethoxy)phenyl)propan-1-amine (15)

A solution of 1-(4-(2-methoxyethoxy)phenyl)propan-1-one oxime (1.5 g, 6.7 mmol) in tetrahydrofuran (20 mL) was added dropwise to a stirred suspension of lithium aluminum hydride (0.78 g, 20.55 mmol) in tetrahydrofuran (48 mL) at room temperature under nitrogen. After 18 hours the mixture was heated at reflux for 3 hours, then allowed to cool. 0.8 mL of water was added drop-wise, followed by 0.8 mL of 15% aq sodium hydroxide, and then 2.4 mL of water. After several minutes the mixture was filtered, and the residue washed twice with tetrahydrofuran. The combined filtrate and washings were concentrated in vacuo, leaving 1.34 g of clear golden oil, which was flash chromatographed on a column (5×10 cm) of silica gel eluting with Hxa/EtOAc/acetone 8:1:1 to afford 0.83 g of the product as a clear golden oil; mass spec ES+m/z=210 (m+1).

2-Cyano-N-(1-(4-(2-methoxyethoxy)phenyl)propyl) acetamide (16)

Oxalyl chloride (0.19 g, 1.49 mmol) was added to a stirred solution of cyanoacetic acid (0.107 g, 1.25 mmol) in a mixture of dichloromethane (5 mL) and 2 drops of dimethylformamide under nitrogen at ice bath temperature. After 2 hours the solution was added in one portion to a solution of 1-(4-(2-methoxyethoxy)phenyl)propan-1-amine (0.25 g, 1.2 mmol) and triethylamine (0.13 g, 1.3 mmol) in tetrahydrofuran/dichloromethane 1:1 (4 mL) at 0-5° C., and the mixture was allowed to warm slowly to room temperature. After 4 hours 80 mL of water was added and after half an hour more (30 mL) dichloromethane was added. The layers were separated and the aqueous layer extracted with additional dichloromethane. The combined extracts were washed with 1N aq sodium bicarbonate, and then sat brine, and dried over magnesium sulfate. The solvent was removed in vacuo, leaving a cloudy amber syrup which was dissolved in EtOAc/Hxa 1:1 and filtered through a short column of silica gel under pressure. The effluent was concentrated in vacuo to afford 0.24 g of the product as a cloudy pale amber syrup, sufficiently pure for the next step.

(E)-3-(6-Bromopyridin-2-yl)-2-cyano-N-(1-(4-(2-methoxyethoxy)phenyl)propyl)-acrylamide (17)

Potassium t-butoxide (0.014 g, 0.127 mmol) was added to a stirred solution of 6-bromo-2-pyridinecarboxaldehyde (0.094 g, 0.51 mmol) and 2-cyano-N-(1-(4-(2-methoxyethoxy)-phenyl)propyl)acetamide (0.07 g, 0.25 mmol) in dimethylsulfoxide (10 mL) under nitrogen at room temperature. After 26 hours the mixture was shaken with water and then extracted with ethyl acetate several times. The combined extracts were washed with water and then dried over sodium sulfate. The solvent was removed in vacuo leaving 0.10 g of a clear amber syrup, which was flash chromatographed on a column (5×10 cm) of silica gel with gradient elution utilizing dichloromethane/EtOAc (10:0 gradually changing to 12:1) to afford 0.040 g of the product as a clear pale yellow syrup; mass spec ES+m/z=444, 466 (m+1, m+23).

3-(6-Bromo-pyridin-2-yl)-2-cyano-3-(2,3-dihydroxy-4-mercapto-butylsulfanyl)-N-(1-phenyl-butyl)-propionamide (19)

A solution of WP1130 (18; 0.05 g, 0.13 mmol) in acetonitrile (6 mL) was added to a stirred solution of dithiothreitol (2 g, 13 mmol) in acetonitrile (13 mL) at room temp. After 20 hours TLC [Hxa/EtOAc 1:1] showed a single product and no starting material. The mixture was filtered through a short column of silica gel in acetonitrile, and the filtrate stripped of solvent under reduced pressure. A colorless syrup was obtained. The syrup was dissolved in ethyl acetate and flash chromatographed on a column (35×70 mm) of silica gel in ethyl acetate to afford a clear yellow oil (0.02 g) which began to crystallize upon standing. Mass spec ES+; m/z=560, 562 (m+23) and 538, 540 (m+1).

3-(6-Bromopyridin-2-yl)-2-cyano-3-((2,3-dihydroxypropyl)thio)-N—((S)-1-phenylbutyl)propanamide (20)

Thioglycerol (42 μL, 0.5 mmol) was added to a stirred solution of WP1130 (19 mg, 0.05 mmol) in acetonitrile (0.5 mL). The resulting mixture was stirred at room temperature for 17 hours. The mixture was distributed between water and dichloromethane. The separated organic layer was washed with sat. brine, dried over sodium sulfate, and concentrated to an oil. Purification by preparative TLC eluting with hexanes/ethyl acetate (6:4) afforded 20 (20 mg, 82%) as a clear oil: MS (ES$^+$) m/z 492.0 (M+H)$^+$.

1-(4-(2-(Diethylamino)ethoxy)phenyl)butan-1-one (21)

2-(Diethylamino)ethyl chloride hydrochloride (624 mg, 3.65 mmol) was added to a stirred solution of p-hydroxybutyrophenone (200 mg, 1.21 mmol) in anhydrous acetone (6 mL) followed by the addition of potassium carbonate (668 mg, 4.84 mmol). The resulting mixture was heated at reflux for 48 hours. The mixture was diluted with ethyl acetate, washed with water (2×) and sat. brine, dried over sodium sulfate, and concentrated to an oil. Flash silica gel column chromatography, eluting with 1:1 hexanes/ethyl acetate, afforded 21 (315 mg, 98%) as a light yellow oil: MS (ES$^+$) m/z 264.1 (M+H)$^+$.

1-(4-(2-(Dimethylamino)ethoxy)phenyl)butan-1-one (22)

The title compound was prepared using a similar procedure as described for the preparation of 21 except that 2-(dimethylamino)ethyl chloride hydrochloride was used instead of 2-(diethylamino)ethyl chloride hydrochloride. This produced a crude oil, which was purified by flash silica gel column chromatography (gradient elution from 1:1 hexanes/ethyl acetate to ethyl acetate) to give 22 (580 mg, 81%) as a light yellow oil: MS (ES$^+$) m/z 236.1 (M+H)$^+$.

1-(4-(2-(Pyrrolidin-1-yl)ethoxy)phenyl)butan-1-one (23)

The title compound was prepared by using a similar procedure as described for the preparation of 21 except that 1-(2-chloroethyl)pyrrolidine hydrochloride was used instead of 2-(diethylamino)ethyl chloride hydrochloride. This produced a crude oil, which was purified by flash silica gel column chromatography, eluting with 3:1 hexanes/ethyl acetate, to give 23 (455 mg, 87%) as a clear oil: MS (ES$^+$) m/z 262.1 (M+H)$^+$.

1-(4-(2-Morpholinoethoxy)phenyl)butan-1-one (24)

The title compound was prepared by using a similar procedure as described for the preparation of 21 except that N-(2-chloroethyl)morpholine hydrochloride was used instead of 2-(diethylamino)ethyl chloride hydrochloride. This produced a crude oil, which was purified by silica gel column chromatography, eluting with 1:1 hexanes/ethyl acetate, to give 24 (550 mg, quantitative) as a clear oil: MS (ES$^+$) m/z 278.1 (M+H)$^+$.

1-(4-(2-(Diethylamino)ethoxy)phenyl)butan-1-amine (25)

Sodium cyanoborohydride (155 mg, 3.5 mmol) was added to a suspension of 1-(4-(2-(diethylamino)ethoxy)phenyl)butan-1-one (21; 186 mg, 0.7 mmol) and ammonium acetate (1.63 g, 21.2 mmol) in methanol (2 mL). The resulting mixture was then heated at 40° C. for 72 hours. The reaction mixture was diluted with ethyl acetate, washed with sat. aqueous NaHCO$_3$ (2×) and sat. brine, dried over sodium sulfate and concentrated to give crude 25 (110 mg, 59%) as a yellow oil: MS (ES$^+$) m/z 265.1 (M+H)$^+$. This material was taken to the next step without further purification.

1-(4-(2-(Dimethylamino)ethoxy)phenyl)butan-1-amine (26)

The title compound was prepared by using a similar procedure as described for the preparation of 25 except that 1-(4-(2-(dimethylamino)ethoxy)phenyl)butan-1-one (22) was used instead of 1-(4-(2-(diethylamino)ethoxy)phenyl)butan-1-one (21). This produced crude 26 (410 mg, 73%) as a yellow oil: MS (ES$^+$) m/z 237.1 (M+H)$^+$.

1-(4-(2-(Pyrrolidin-1-yl)ethoxy)phenyl)butan-1-amine (27)

The title compound was prepared by using a similar procedure as described for the preparation of 25 except that 1-(4-(2-(pyrrolidin-1-yl)ethoxy)phenyl)butan-1-one (23) was used instead of 1-(4-(2-(diethylamino)ethoxy)phenyl)butan-1-one (21). This produced crude 27 (188 mg, 45%) as a yellow oil: MS (ES$^+$) m/z 263.2 (M+H)$^+$.

1-(4-(2-Morpholinoethoxy)phenyl)butan-1-amine (28)

The title compound was prepared by using a similar procedure as described for the preparation of 25 except that 1-(4-(2-morpholinoethoxy)phenyl)butan-1-one (24) was used instead of 1-(4-(2-(diethylamino)ethoxy)phenyl)butan-1-one (21). This produced crude 28 (390 mg, 70%) as a light yellow oil: MS (ES$^+$) m/z 279.2 (M+H)$^+$.

2-Cyano-N-(1-(4-(2-(diethylamino)ethoxy)phenyl)butyl)acetamide (29)

To an ice cooled solution of cyanoacetic acid (37 mg, 0.43 mmol) in DMF (2 mL) was added 7-aza-1-hydroxybenzotriazole (HOAt; 59 mg, 0.43 mmol), O-(7-azabenzotriazol-1-yl)-N,N,N',N'-tetramethyluronium hexafluorophosphate (HATU; 165 mg, 0.43 mmol), diisopropylethylamine (DIPEA; 167 µL, 0.958 mmol) and 1-(4-(2-(diethylamino)ethoxy)phenyl)butan-1-amine (25; 115 mg, 0.43 mmol). The resulting mixture was then stirred at room temperature for 18 hours. The reaction mixture was diluted with ethyl acetate, washed with sat. aqueous NaHCO$_3$ (2×) and sat. brine, dried over sodium sulfate, and concentrated to a thick yellow oil. Purification by flash silica gel column chromatography, eluting with 5:95 methanol/dichloromethane, afforded 29 (116 mg, 80%) as a yellow oil: MS (ES$^+$) m/z 332.2 (M+H)+.

2-cyano-n-(1-(4-(2-(dimethylamino)ethoxy)phenyl)butyl)acetamide (30)

The title compound was prepared by using a similar procedure as described for the preparation of 29 except that 1-(4-(2-(dimethylamino)ethoxy)phenyl)butan-1-amine (26) was used instead of 1-(4-(2-(diethylamino)ethoxy)phenyl)butan-1-amine (25). This produced crude product which was purified by flash silica gel column chromatography, eluting with 5:95 methanol/dichloromethane, to give 30 (320 mg, 61%) as a thick yellow oil: MS (ES$^+$) m/z 304.1 (M+H)$^+$.

2-Cyano-N-(1-(4-(2-(pyrrolidin-1-yl)ethoxy)phenyl)butyl)acetamide (31)

The title compound was prepared by using a similar procedure as described for the preparation of 29 except that 1-(4-(2-(pyrrolidin-1-yl)ethoxy)phenyl)butan-1-amine (27) was used instead of 1-(4-(2-(diethylamino)ethoxy)phenyl)butan-1-amine (25). This produced crude product which was purified by flash silica gel column chromatography, eluting with 5:95 methanol/dichloromethane, to give 31 (140 mg, 60%) as a thick yellow oil: MS (ES$^+$) m/z 330.2 (M+H)$^+$.

2-Cyano-N-(1-(4-(2-morpholinoethoxy)phenyl)butyl)acetamide (32)

The title compound was prepared by using a similar procedure as described for the preparation of 29 except that 1-(4-(2-morpholinoethoxy)phenyl)butan-1-amine (28) was used instead of 1-(4-(2-(diethylamino)ethoxy)phenyl)butan-1-amine (25). This produced a crude product which was purified by flash silica gel column chromatography, eluting with 4:96 mixture of methanol/dichloromethane, to give 32 (370 mg, 76%) as a clear oil: MS (ES⁺) m/z 346.2 (M+H)⁺.

(E)-3-(6-Bromopyridin-2-yl)-2-cyano-N-(1-(4-(2-(diethylamino)ethoxy)phenyl)butyl)acrylamide (33)

To the solution of 2-cyano-N-(1-(4-(2-(diethylamino)ethoxy)phenyl)butyl)acetamide (29; 116 mg, 0.35 mmol) in ethanol (2 mL) was added β-alanine (499 mg, 5.6 mmol) and water (2 mL). 6-Bromopicolinaldehyde (260 mg, 1.4 mmol) was added, and the resulting mixture was then stirred at room temperature for 18 hours. The reaction mixture was diluted with ethyl acetate, washed with sat. aqueous NaHCO₃ (2×) and sat. brine, dried over sodium sulfate, and concentrated to a crude solid. Purification by flash silica gel column chromatography, eluting with 5:95 methanol/dichloromethane, afforded 33 (140 mg, 80%) as a thick yellow oil: MS (ES⁺) m/z=499.1 (M+H)⁺.

(E)-2-Cyano-N-(1-(4-(2-(diethylamino)ethoxy)phenyl)butyl)-3-(6-fluoropyridin-2-yl)acrylamide (34)

The title compound was prepared by using a similar procedure as described for the preparation of 33 except that 6-fluoropicolinaldehyde was used instead of 6-bromopicolinaldehyde. This produced crude product which was purified by flash silica gel column chromatography, eluting with 4:96 methanol/dichloromethane, to give 34 (105 mg, 61%) as a yellow oil: MS (ES⁺) m/z 439.2 (M+H)+.

(E)-3-(6-Bromopyridin-2-yl)-2-cyano-N-(1-(4-(2-(dimethylamino)ethoxy)phenyl)butyl)acrylamide (35)

The title compound was prepared by using a similar procedure as described for the preparation of 33 except that 2-cyano-N-(1-(4-(2-(dimethylamino)ethoxy)phenyl)-butyl)acetamide (30) was used instead of 2-cyano-N-(1-(4-(2-(diethylamino)ethoxy)phenyl)butyl)acetamide (29). This produced the crude product which was purified by flash silica gel column chromatography, eluting with 4:96 methanol/dichloromethane, to give 35 (120 mg, 76%) as a yellow oil: MS (ES⁺) m/z 471.1 (M+H)⁺.

(E)-2-Cyano-3-(6-fluoropyridin-2-yl)-N-(1-(4-(2-(pyrrolidin-1-yl)ethoxy)phenyl)butyl)acrylamide (36)

The title compound was prepared by using a similar procedure as described for the preparation of 33 except that 6-fluoropicolinaldehyde was used instead of 6-bromopicolinaldehyde, and 2-cyano-N-(1-(4-(2-(pyrrolidin-1-yl)ethoxy)phenyl)butyl)acetamide (31) was used instead of 2-cyano-N-(1-(4-(2-(diethylamino)ethoxy)phenyl)butyl)acetamide (29). This produced the crude product which was purified by flash silica gel column chromatography, eluting with 4:96 methanol/dichloromethane, to give 36 (65 mg, 35%) as a light yellow oil: MS (ES⁺) m/z 437.2 (M+H)⁺.

(E)-2-Cyano-3-(6-fluoropyridin-2-yl)-N-(1-(4-(2-morpholinoethoxy)phenyl)butyl)acrylamide (37)

The title compound was prepared by using a similar procedure as described for the preparation of 33 except that 6-fluoropicolinaldehyde was used instead of 6-bromopicolinaldehyde, and 2-cyano-N-(1-(4-(2-morpholinoethoxy)phenyl)butyl)acetamide (32) was used instead of 2-cyano-N-(1-(4-(2-(diethylamino)ethoxy)phenyl)butyl)acetamide (29). This produced the crude product which was purified by flash silica gel column chromatography, eluting with 4:96 methanol/dichloromethane, to give 37 (130 mg, 77%) as a light yellow oil: MS (ES⁺) m/z 453.2 (M+H)⁺.

(E)-2-Cyano-N-(1-(4-(2-(dimethylamino)ethoxy)phenyl)butyl)-3-(1H-imidazol-2-yl)acrylamide (38)

The title compound was prepared by using a similar procedure as described for the preparation of 33 except that 1H-imidazole-2-carbaldehyde was used instead of 6-bromopicolinaldehyde, and 2-cyano-N-(1-(4-(2-(dimethylamino)ethoxy)phenyl)butyl)acetamide (30) was used instead of 2-cyano-N-(1-(4-(2-(diethylamino)ethoxy)phenyl)butyl) acetamide (29). This produced the crude product which was purified by flash silica gel column chromatography, eluting with 8:92 methanol/dichloromethane, to give 38 (80 mg, 63%) as a light yellow oil: MS (ES⁺) m/z 453.2 (M+H)⁺.

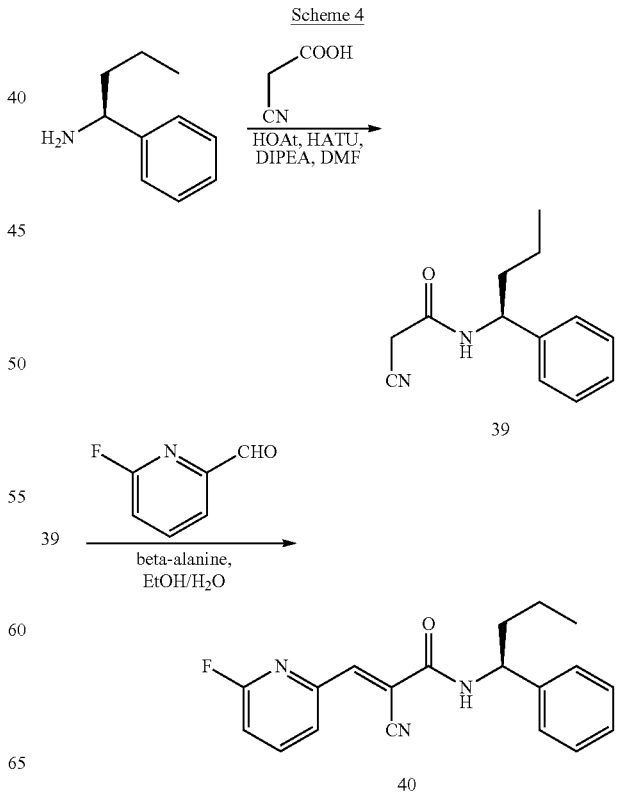

Scheme 4

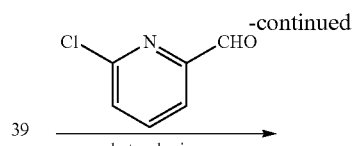

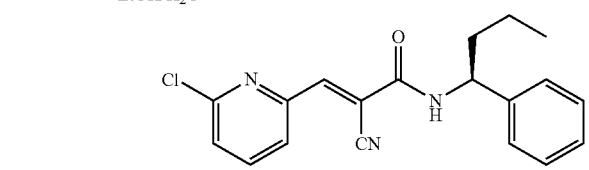

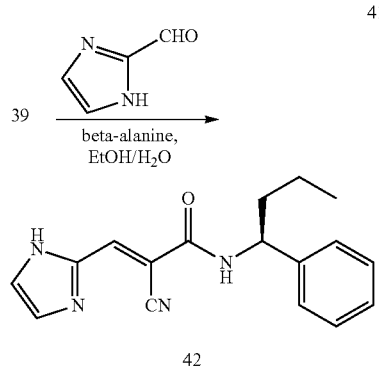

(S)-2-Cyano-N-(1-phenylbutyl)acetamide (39)

The title compound was prepared by using a similar procedure as described for the preparation of 29 except that (S)-1-phenylbutylamine was used instead of 1-(4-(2-(diethylamino)ethoxy)phenyl)butan-1-amine (25). This produced crude product which was purified by flash silica gel column chromatography, eluting with 7:3 hexanes/ethyl acetate, to give 39 (375 mg, 58%) as a white solid: MS (ES$^+$) m/z 217.1.1 (M+H)$^+$.

(S,E)-2-Cyano-3-(6-fluoropyridin-2-yl)-N-(1-phenylbutyl)acrylamide (40)

The title compound was prepared by using a similar procedure as described for the preparation of 33 except that 6-fluoropicolinaldehyde was used instead of 6-bromopicolinaldehyde, and (S)-2-cyano-N-(1-phenylbutyl)acetamide was used instead of 2-cyano-N-(1-(4-(2-(diethylamino)ethoxy)phenyl)butyl)acetamide (29), This produced the crude product which was purified by flash silica gel column chromatography, eluting with 8:2 hexanes/ethyl acetate, to give 40 (115 mg, 96%) as a clear oil: MS (ES$^+$) m/z 324.1 (M+H)$^+$.

(S,E)-2-Cyano-3-(6-chloropyridin-2-yl)-N-(1-phenylbutyl)acrylamide (41)

The title compound was prepared by using a similar procedure as described for the preparation of 33 except that 6-chloropicolinaldehyde was used instead of 6-bromopicolinaldehyde, and (S)-2-cyano-N-(1-phenylbutyl)acetamide was used instead of 2-cyano-N-(1-(4-(2-(diethylamino)ethoxy)phenyl)butyl)acetamide (29). This produced the crude product which was purified by flash silica gel column chromatography, eluting with 8:2 hexanes/ethyl acetate, to give 41 (105 mg, 95%) as a clear oil: MS (ES$^+$) m/z 340.1 (M+H)$^+$.

(S,E)-2-Cyano-3-(1H-imidazol-2-yl)-N-(1-phenylbutyl)acrylamide (42)

The title compound was prepared by using a similar procedure as described for the preparation of 33 except that 1H-imidazole-2-carbaldehyde was used instead of 6-bromopicolinaldehyde, and (S)-2-cyano-N-(1-phenylbutyl)acetamide was used instead of 2-cyano-N-(1-(4-(2-(diethylamino)ethoxy)phenyl)butyl)acetamide (29). This produced the crude product which was purified by flash silica gel column chromatography, eluting with 1:1 hexanes/ethyl acetate, to give 42 (92 mg, 94%) as a clear oil: MS (ES$^+$) m/z 295.1 (M+H)$^+$.

Scheme 5

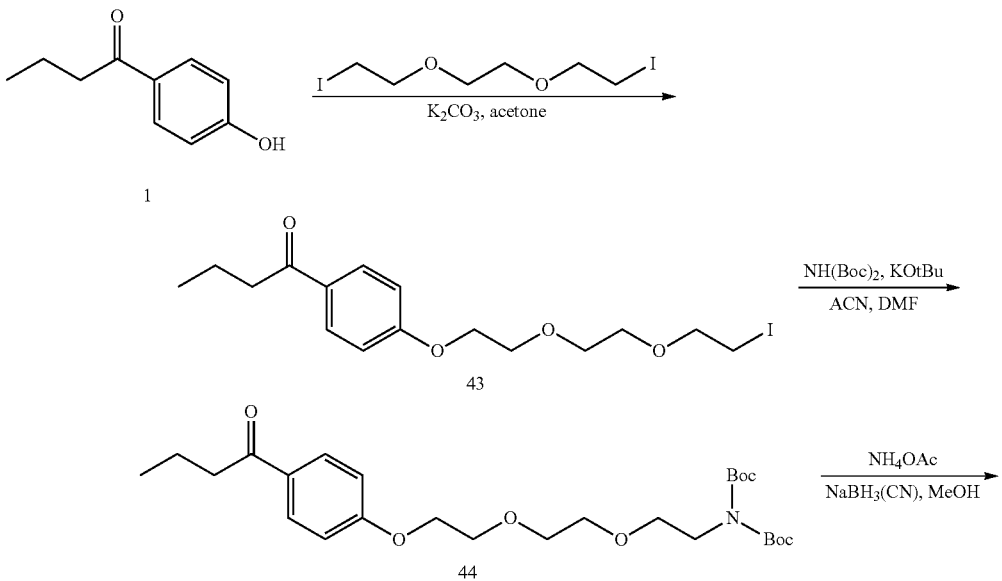

-continued
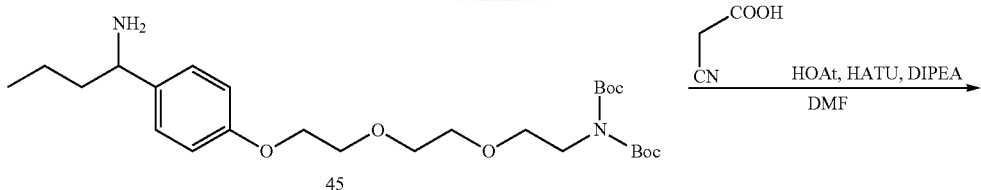
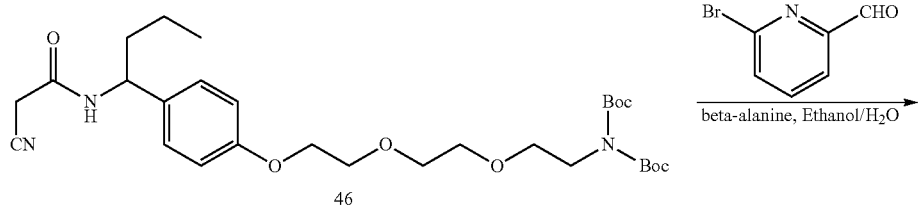
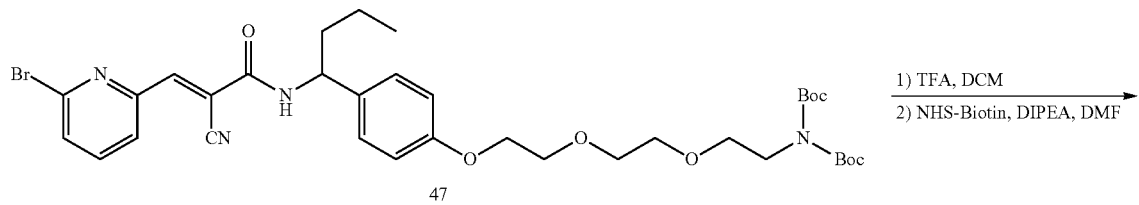
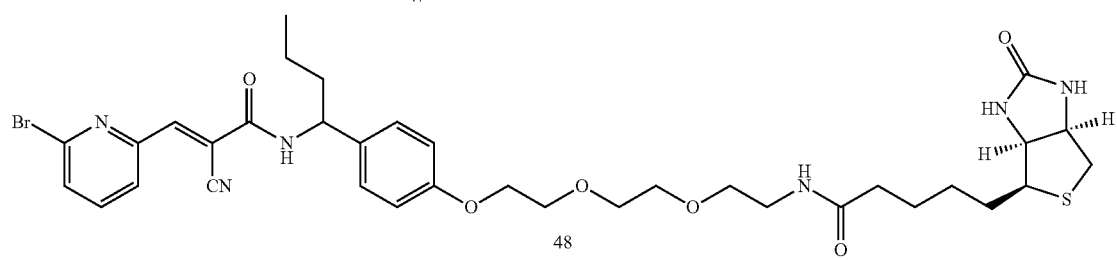
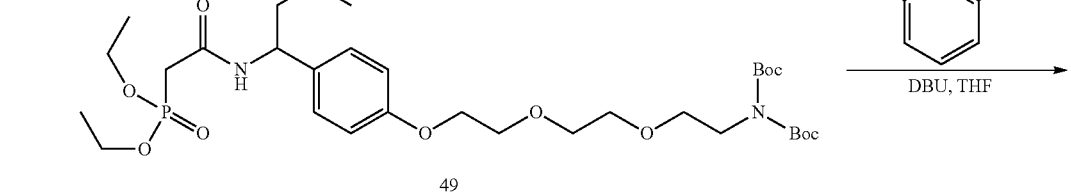
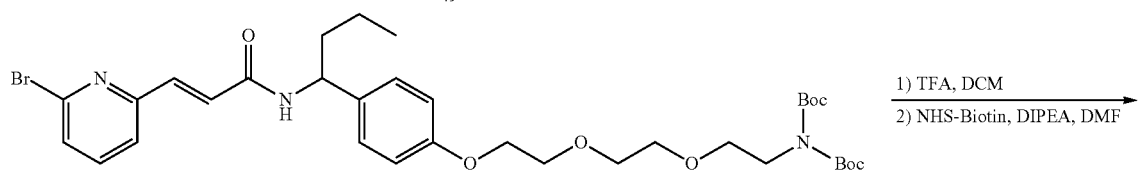
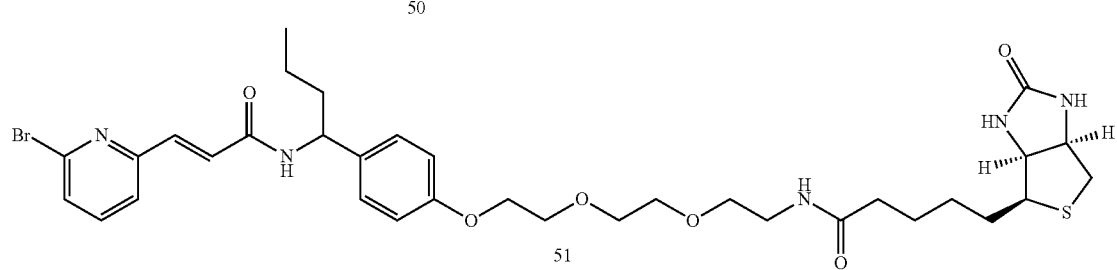

1-(4-(2-(2-(2-Iodoethoxy)ethoxy)ethoxy)phenyl) butan-1-one (43)

The title compound was prepared by using a similar procedure as described for the preparation of 21 except that 1,2-bis-(2-iodoethyloxy)ethane was used instead of 2-(diethylamino)ethyl chloride hydrochloride. This produced the crude product which was purified by flash silica gel column chromatography, eluting with 4:1 hexanes/ethyl acetate to give 43 (3.85 g, 52%) as a clear oil: MS (ES$^+$) m/z 407.0 (M+H)$^+$.

(2-(2-(2-(4-Butyrylphenoxy)ethoxy)ethoxy)ethyl) imidodicarbonic acid, 1,3-bis-tert-butyl ester (44)

Di-tert-butyliminodicarboxylate (3.05 g, 14.07 mmol) and potassium tert-butoxide (1.58 g, 14.07 mmol) were stirred in DMF (50 mL) for 15 minutes followed by the addition of 1-(4-(2-(2-(2-iodoethoxy)ethoxy)ethoxy)phenyl)butan-1-one (43; 3.81 g, 9.38 mmol). The resulting mixture was stirred under nitrogen for 18 hours, and then poured into 200 mL of ethyl acetate. This solution was washed with water (2×) and sat. brine, dried over sodium sulfate, and concentrated to afford a liquid that was purified by flash silica gel column chromatography, eluting with 3:1 hexanes/ethyl acetate to afford 44 (2.27 g, 49%) as a clear oil: MS (ES$^+$) m/z 496.2 (M+H)$^+$.

(2-(2-(2-(4-(1-Aminobutyl)phenoxy)ethoxy)ethoxy) ethyl)imidodicarbonic acid, 1,3-bis-tert-butyl ester (45)

The title compound was prepared by using a similar procedure as described for the preparation of 25 except that (2-(2-(2-(4-butyrylphenoxy)ethoxy)ethoxy)ethyl)imidodicarbonic acid, 1,3-bis-tert-butyl ester (44) was used instead of 1-(4-(2-(diethylamino)ethoxy)phenyl)butan-1-one (21). This produced the crude product which was purified by flash silica gel column chromatography, eluting with ethyl acetate, to give 45 (730 mg, 73%) as a clear oil: MS (ES$^+$) m/z 497.3 (M+H)$^+$.

(2-(2-(2-(4-(1-(2-Cyanoacetamido)butyl)phenoxy) ethoxy)ethoxy)ethyl)imidodicarbonic acid, 1,3-bis-tert-butyl ester (46)

The title compound was prepared by using a similar procedure as described for the preparation of 29 except that (2-(2-(2-(4-(1-aminobutyl)phenoxy)ethoxy)ethoxy)ethyl) imidodicarbonic acid, 1,3-bis-tert-butyl ester (45) was used instead of 1-(4-(2-(diethylamino)ethoxy)phenyl)butan-1-amine (25). This produced the crude product which was purified by flash silica gel column chromatography, eluting with 3:2 hexanes/ethyl acetate, to give 46 (95 mg, 84%) as a clear oil: MS (ES$^+$) m/z 564.3 (M+H)$^+$.

(E)-(2-(2-(2-(4-(1-(3-(6-Bromopyridin-2-yl)-2-cyanoacrylamido)butyl)phenoxy)ethoxy)ethoxy)ethyl) imidodicarbonic acid, 1,3-bis-tert-butyl ester (47)

The title compound was prepared by using a similar procedure as described for the preparation of 33 except that (2-(2-(2-(4-(1-(2-cyanoacetamido)butyl)phenoxy)ethoxy) ethoxy)ethyl)imidodicarbonic acid, 1,3-bis-tert-butyl ester (46) was used instead of 2-cyano-N-(1-(4-(2-(diethylamino) ethoxy)phenyl)butyl)acetamide (29). This produced the crude product which was purified by flash silica gel column chromatography, eluting with 7:3 hexanes/ethyl acetate, to give 47 (105 mg, 85%) as a clear oil: MS (ES$^+$) m/z 731.2 (M+H)$^+$.

N-(2-(2-(2-(4-(1-((E)-3-(6-Bromopyridin-2-yl)-2-cyanoacrylamido)butyl)phenoxy)ethoxy)ethoxy) ethyl)-5-((3aS,4S,6aR)-2-oxohexahydro-1H-thieno [3,4-d]imidazol-4-yl)pentanamide (48)

A mixture of (E)-(2-(2-(2-(4-(1-(3-(6-bromopyridin-2-yl)-2-cyanoacrylamido)butyl)phenoxy)ethoxy)ethoxy)ethyl) imidodicarbonic acid, 1,3-bis-tert-butyl ester (47; 105 mg, 0.14 mmol) and trifluoroacetic acid (0.3 mL) was stirred in dichloromethane (3 mL) for 1.5 hours. The solution was concentrated and the residue was dissolved in N,N-dimethylformamide. To this solution at ice bath temperature was added D-biotin N-hydroxysuccinimide ester (49 mg, 0.14 mmol) and DIPEA (75 µL, 0.43 mmol). The resulting mixture was stirred at this temperature for 2 hours and then partitioned between dichloromethane and water. The organic phase was washed with water (2×) and sat. brine, dried over sodium sulfate, and concentrated to afford an oil. Purification by flash silica gel column chromatography, eluting with 7:93 methanol/dichloromethane, provided 48 (55 mg, 51%) as a pale yellow oil: (MS (ES$^+$) m/z 757.2 (M+H)$^+$.

(2-(2-(2-(4-(1-(2-(Diethoxyphosphoryl)acetamido) butyl)phenoxy)ethoxy)ethoxy)ethyl)imidodicarbonic acid, 1,3-bis-tert-butyl ester (49)

A mixture of 4-dimethylaminopyridine (DMAP; 197 mg, 1.61 mmol) and 1-ethyl-3-(3-dimethylaminopropyl)carbodiimide hydrochloride (EDC.HCl; 309 mg, 1.61 mmol) was added to a stirred solution of diethylphosphonoacetic acid (129 µL, 0.805 mmol) and (2-(2-(2-(4-(1-aminobutyl)phenoxy)ethoxy)ethoxy)ethyl)imidodicarbonic acid, 1,3-bis-tert-butyl ester (45; 400 mg, 0.805 mmol) in N,N-dimethylformamide (10 mL). The resulting mixture was stirred under nitrogen for 3 hours at room temperature, and then poured into 100 mL of ethyl acetate. This solution was washed with 1N aqueous HCl (2×) and sat. brine, dried over sodium sulfate, and concentrated to an oil. Purification by flash silica gel column chromatography, eluting with ethyl acetate, afforded 49 (540 mg, quantitative) as a clear oil: MS (ES$^+$) m/z 675.3 (M+H)$^+$.

(E)-(2-(2-(2-(4-(1-(3-(6-Bromopyridin-2-yl)acrylamido)butyl)phenoxy)ethoxy)ethoxy)ethyl)imidodicarbonic acid, 1,3-bis-tert-butyl ester (50)

To a suspension of NaH (52 mg 60% in mineral oil, 1.31 mmol) in tetrahydrofuran (1.0 mL) at ice bath temperature was added a solution of (2-(2-(2-(4-(1-(2-(diethoxyphosphoryl)acetamido)butyl)phenoxy)ethoxy)ethoxy)ethyl)imidodicarbonic acid, 1,3-bis-tert-butyl ester (49; 295 mg, 0.43 mmol) in tetrahydrofuran (2 mL). The resulting mixture was stirred at room temperature for 30 minutes and then treated drop-wise with 6-bromopicolinaldehyde (81 mg, 0.43 mmol) in tetrahydrofuran (2 mL). The mixture was stirred for another 30 minutes, and then carefully quenched with water. The solution was extracted with ethyl acetate (3×), and the combined organic extracts were washed with sat. brine, dried over sodium sulfate, and concentrated to an oil. Purification by flash silica gel column chromatography, eluting with 7:3 hexanes/ethyl acetate, afforded 50 (205 mg, 67%) as a clear oil: MS (ES$^+$) m/z 706.2 (M+H)$^+$.

N-(2-(2-(2-(4-(1-((E)-3-(6-Bromopyridin-2-yl)acry-lamido)butyl)phenoxy)ethoxy)ethoxy)ethyl)-5-((3aS,4S,6aR)-2-oxohexahydro-1H-thieno[3,4-d]imidazol-4-yl)pentanamide (51)

The title compound was prepared by using a similar procedure as described for the preparation of 48 except that acrylamide 50 was used instead of cyanoacrylamide 47. This produced the crude product which was purified by flash silica gel column chromatography, eluting with 7:93 methanol/dichloromethane, to give 51 (50 mg, quantitative) as a clear oil: MS (ES$^+$) m/z 731.2 (M+H)$^+$.

Assessing Compounds for Activity Against DUB

Compounds were screened for DUB inhibitory and apoptotic activity in a panel of CML, myeloma and Mantle cell lymphoma cell lines, and compared to WP1130. The effects on cell growth and survival by selected compounds are compared to WP1130 in Table 1, e.e., a compound that is more sensitive is one that has a greater inhibitory activity compared to WP1130, while a compound that is less sensitive is one that has a lesser inhibitory activity compared to WP1130. Selected compounds were also tested for DUB inhibition in intact cells (Table 2) and in isolated DUB (Usp9x-UCH domain) enzyme preparations (Table 3). General descriptions of the methods employed in these assays can be found, e.g., in Kapuria, et al., A novel small molecule deubiquitinase inhibitor blocks Jak2 signaling through Jak2 ubiquitination, *Cell Signal,* 2011, in press; Kapuria, et al., Deubiquitinase inhibition by small-molecule WP1130 triggers aggresome formation and tumor cell apoptosis. *Cancer Res,* 2010. 70(22): p. 9265-76; Sun, et al., Bcr-Abl ubiquitination and Usp9x inhibition block kinase signaling and promote CML cell apoptosis. *Blood,* 2011. 117(11): p. 3151-62; Kapuria, et al., Protein cross-linking as a novel mechanism of action of a ubiquitin-activating enzyme inhibitor with anti-tumor activity. *Biochem Pharmacol,* 2011. 82(4): p. 341-9; and Bartholomeusz, et al., Activation of a novel Bcr/Abl destruction pathway by WP1130 induces apoptosis of chronic myelogenous leukemia cells. *Blood,* 2007. 109(8): p. 3470-8.

TABLE 1

| Compound | MTT Cell Line | MTT Activity relative to WP1130 |
|---|---|---|
| 6 | WDT2 | More sensitive |
| 7 | WDT2 | More sensitive |
| 17 | K562 | Less sensitive |
| 20 | K562 | More sensitive |
| 33 | Z138 | Less sensitive |
| 34 | Z138 | Less sensitive |
| 35 | Z138 | Less sensitive |
| 36 | Z138 | Less sensitive |
| 37 | Z138 | Less sensitive |
| 38 | Z138 | Less sensitive |
| 41 | Z138 | Less sensitive |
| 42 | Z138 | Less sensitive |
| 40 | Z138 | Less sensitive |

TABLE 2

| Compound | Western Cell Line | Western Targets |
|---|---|---|
| 8 | H929, WDT2, Z138 | USP9X and DUB activity: no effect |
| 9 | H929, WDT2, Z138 | USP9X and DUB activity: down-regulated in all three cells lines |
| 10 | H929, WDT2, Z138 | USP9X and DUB activity: no effect |
| 11 | H929, WDT2, Z138 | USP9X and DUB activity: no effect |

TABLE 2-continued

| Compound | Western Cell Line | Western Targets |
|---|---|---|
| 20 | SET, HEL | pStat5: down-regulated; DUB activity: no effect; Mcl: down-regulated in HEL and no effect in SET. |
| 36 | Z138 | USP9X and DUB activity and Mcl1: down-regulated a little but much less sensitive than WP1130. |
| 37 | Z138 | USP9X and DUB activity and Mcl1: down-regulated but less sensitive than WP1130 by two-fold. |

TABLE 3

| Compound | AMC Assay on USP9X-UCH Activity relative to WP1130 |
|---|---|
| 33 | Same |
| 34 | No inhibition |
| 35 | Inconclusive |
| 36 | No inhibition |
| 37 | No inhibition |
| 38 | Inconclusive |
| 40 | Less sensitive |
| 41 | Inconclusive |
| 42 | Less sensitive |

Compound Activity Against Viruses

Compounds were also tested against various viruses, as noted in Table 4. Norwalk virus genome titers were measured by qRT-PCR for after 24 hrs of WP1130 treatment in a replicon-containing cell line (Chang, Sosnovtsev et al. 2006). All other experiments were carried out as follows: cells were pre-treated with 5 µM of compound for 30 min at 37 C. Virus infection was performed on ice for 1 hr after which unbound virus was washed off the cells. Cells were incubated for an additional 8-12 hr in the presence of compound before measuring viral titers by plaque assay (Wobus, Karst et al. 2004).

Pre-treatment of cells (30 min with 5 µM) with WP1130 led to a 2-2.5 log reduction in viral titers as determined by plaque assay for the following viruses: murine norovirus, La Crosse virus, encephalomyocarditis virus, and Sindbis virus. Also a 50% reduction in viral genome titers is observed by qRT-PCR for the human norovirus Norwalk in a replicon cell line. The effects were not dependent on cell type as multiple cell lines were tested (murine macrophage RAW 264. 7, primary murine macrophages, African green monkey kidney epithelial cells Vero, human neuronal cells Be2-c, human hepatocytes Huh-7 cells).

A similar reduction (2-2.5 logs) in viral titers by plaque assay was observed for murine norovirus and La Crosse virus using compound 33 in RAW 264.7 cells and Be2-c cells, respectively.

Additional compounds were only tested against murine norovirus in RAW 264.7 cells by the plaque assay. Compounds 35, 40, and 41 reduced viral titers by 2 logs. Compounds 38 and 42 were less effective and reduced viral titers by 0.5 log.

Additional compounds were only tested against murine norovirus in RAW 264.7 cells by plaque assay. Compounds 35, 41, 40, 34, and 36 reduced viral titers by 2 logs. Compound 37 was less effective and reduced viral titers by 1 log, while 38 and 42 reduced viral titers by 0.5 log.

The biotinylated compound 48 reduced murine norovirus titers by 1.5 logs in a plaque assay, while the biotinylated null probe 51 did not reduce murine norovirus titers.

TABLE 4

| Compound | Virus | Cell type | Log inhibition by plaque assay |
|---|---|---|---|
| HWP1130 | Murine norovirus (MNV) | Murine macrophages (RAW264.7, or bone marrow derived) | 2 |
| | La Crosse virus (LaCV) | | 2.5 |
| | Encephalomyocarditis virus | Human neurons (Be2-c) | 2 |
| | Sindbis virus | African green monkey epithelial cells (Vero) | 2 |
| | Norwalk virus replicon | Human hepatoma (HuH-7) | 50% |

```
SEQUENCE LISTING

<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: Synthetic primer

<400> SEQUENCE: 1
gaattccgcc accatggtga gcaagggcg                                29

<210> SEQ ID NO 2
<211> LENGTH: 36
<212> TYPE: DNA
<213> ORGANISM: Artificial Sequence
<220> FEATURE:
<223> OTHER INFORMATION: Synthetic primer

<400> SEQUENCE: 2
gatatcgact tgtacagctc gtccatgccg agagtg                        36
```

TABLE 4-continued

| Compound | Virus | Cell type | Log inhibition by plaque assay |
|---|---|---|---|
| 33 | MNV | Murine macrophages | 2 |
| | LaCV | Human neurons | 2.5 |
| 34 | MNV | Murine macrophages | 2 |
| 35 | MNV | Murine macrophages | 2 |
| 36 | MNV | Murine macrophages | 2 |
| 37 | MNV | Murine macrophages | 1 |
| 38 | MNV | Murine macrophages | 0.5 |
| 41 | MNV | Murine macrophages | 2 |
| 42 | MNV | Murine macrophages | 0.5 |
| 40 | MNV | Murine macrophages | 2 |
| 48 | MNV | Murine macrophages | 1.5 |
| 51 | MNV | Murine macrophages | 0 |

Compound Activity Against Fungi

WP1130 also blocks the replication of the apicomplexan *Toxoplasma gondii* in primary human foreskin fibroblasts. Cells were treated with WP1130 and infected with tachyziotes (RH strain) (MOI 1) for 24 hr before performing immunofluorescence and counting parasite-containing vacuoles. A ~3-fold increase was observed in the number of vacuoles containing only 1 parasite and a ~5-fold decrease in the vacuoles containing 4 parasites.

Compound Activity Against Bacterial Infections

Treatment of RAW264.7 macrophages with 5 μM WP1130 led to a 3-10 fold reduction in *Listeria monocytogenes* titers over an 8 hr infection as determined by measuring intracellular colony forming units over time. Macrophages were exposed to bacterial inoculum at an MOI of 1 for 30 min. Similar effects were observed in primary bone marrow-derived macrophages activated with lipopolysaccharide and interferon-gamma prior to WP-1130 treatment and infection. WP1130 treatment also decreased survival of methicillin-resistant *Staphylococcus aureus* (MRSA) within RAW264.7 macrophages 3-4 fold over an 8 hr infection. This effect was also observed in HeLa human cervical epithelial cells during MRSA infection. A similar reduction in bacterial survival was observed for MRSA using 33 and 40 in RAW 264.7 cells.

What is claimed:

1. A compound having a formula (II) or (IIa):

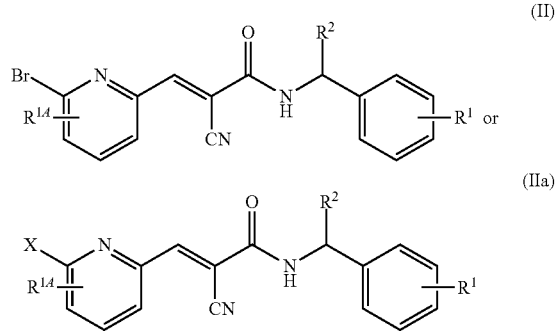

wherein $R^1$ is selected from the group consisting of —O$(CH_2)_m$NEt$_2$; —O$(CH_2)_m$NMe$_2$; —O$(CH_2)_m$NHEt; —O$(CH_2)_m$NHMe; —O$(CH_2)_m$morpholinyl; —O$(CH_2)_m$substituted morpholinyl; —O$(CH_2)_m$sulfoxymorpholinyl; —O$(CH_2)_m$substituted sulfoxymorpholinyl; —O$(CH_2)_m$pyrrolidinyl; —O$(CH_2)_m$substituted pyrrolidinyl; —O$(CH_2)_m$piperazinyl; —O (CH$_2$)$_m$substituted piperazinyl; —O(CH$_2$)$_m$piperidinyl; —O(CH$_2$)$_m$substituted piperidinyl; —O(CH$_2$)$_m$N(Me)(CH$_2$)$_2$NMe$_2$; —O(CH$_2$)$_m$N(Me)(CH$_2$)$_2$NHMe; —O(CH$_2$)$_m$N(Me)(CH$_2$)$_2$NEt$_2$; —O(CH$_2$)$_m$N(Me)(CH$_2$)$_2$NHEt; —O(CH$_2$)$_m$O(CH$_2$)$_2$NMe$_2$; —O(CH$_2$)$_m$O(CH$_2$)$_2$NHMe; —O(CH$_2$)$_m$O(CH$_2$)$_2$NEt$_2$; —O(CH$_2$)$_m$O(CH$_2$)$_2$NHEt; —O(CH$_2$)$_m$O(CH$_2$)$_2$heterocycloalkyl; and —O(CH$_2$)$_m$O(CH$_2$)$_2$substituted heterocycloalkyl;

R$^{14}$ is selected from the group consisting of H, amido, substituted amido, halide, —(CH$_2$)$_m$R$^9$, —NH(CH$_2$)$_m$R$^9$, —NHC(O)(CH$_2$)$_m$R$^9$, —C(O)NH(CH$_2$)$_m$R$^9$ and —O(CH$_2$)$_m$R$^9$;

X is fluoro or chloro;

R$^2$ is alkyl, substituted alkyl, cycloalkyl, substituted cycloalkyl, aryl, substituted aryl, heteroaryl, or substituted heteroaryl, R$^9$ is amino, substituted amino, hydroxy, alkoxy, substituted alkoxy, cycloheteroalkyl, or substituted cycloheteroalkyl; and m is 2, 3, or 4, or a pharmaceutically acceptable salt thereof.

2. The compound of claim 1, where R$^2$ is C$_{1-6}$ alkyl or C$_{3-6}$ cycloalkyl, and is optionally substituted with one or more of hydroxy, amino, substituted amino, alkoxy, and substituted alkoxy.

3. The compound of claim 1, wherein R$^{14}$ is selected from the group consisting of H, —(CH$_2$)$_m$R$^9$, —NH(CH$_2$)$_m$R$^9$, —NHC(O)(CH$_2$)$_m$R$^9$, —C(O)NH(CH$_2$)$_m$R$^9$ and —O(CH$_2$)$_m$R$^9$.

4. The compound of claim 1, wherein R$^9$ is selected from the group consisting of OH, NH$_2$, NHMe, N(Me)$_2$, N(Et)$_2$, O(CH$_2$)$_2$NH$_2$, NH(CH$_2$)$_2$OH, N(Me)(CH$_2$)$_2$N(Me$_2$),

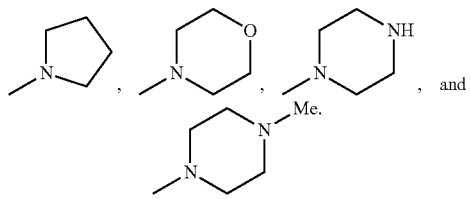

and

5. A compound selected from the group consisting of

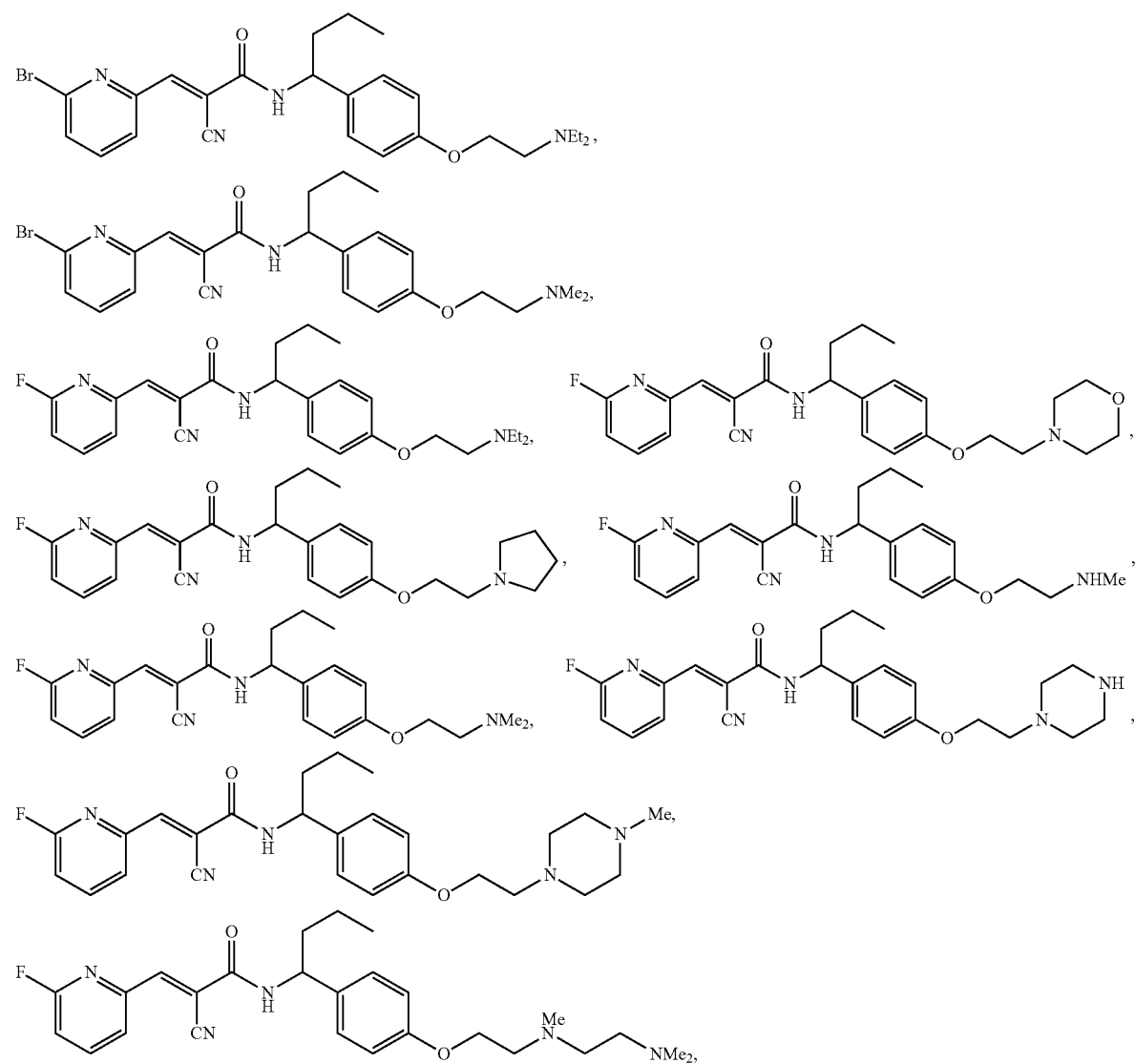

-continued

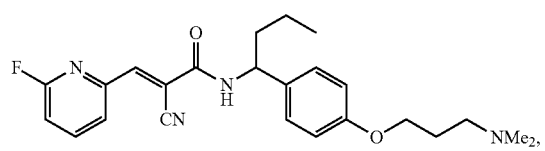
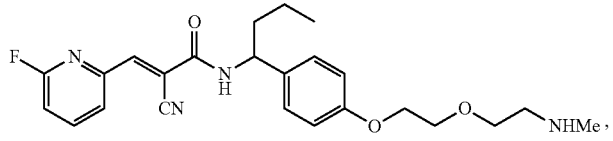
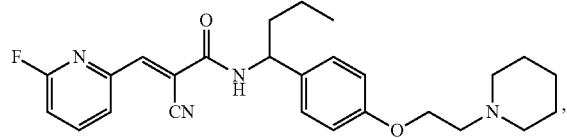
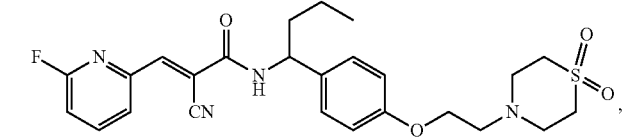
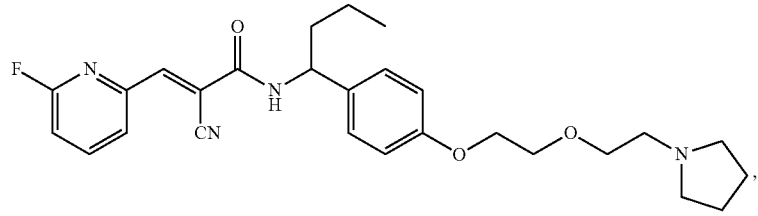
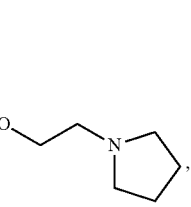
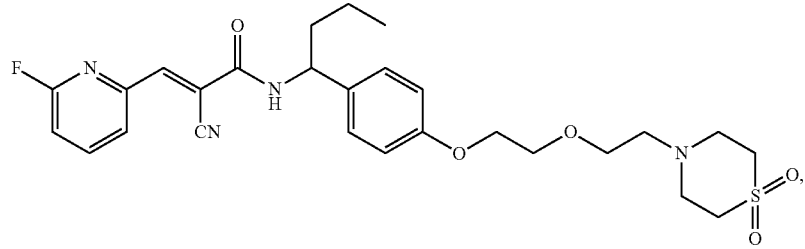
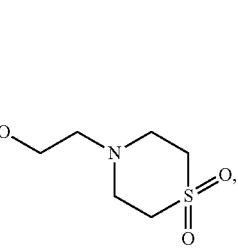
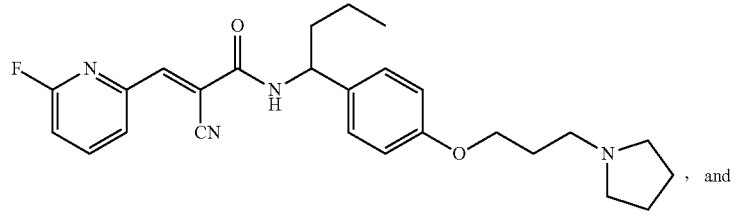
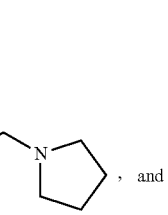
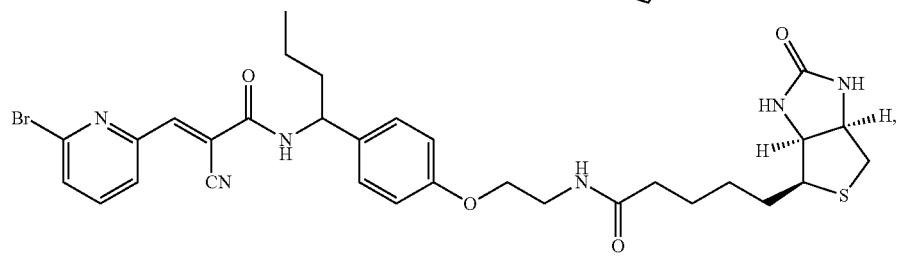

or a pharmaceutically acceptable salt thereof.

6. A method of inhibiting proliferation in a cell comprising contacting the cell with a compound of claim 1 in an amount to inhibit proliferation.

7. The method of claim 6, wherein the cell is a cancer cell.

8. The method of claim 6, wherein the compound inhibits a deubiquitinase (DUB) endogenous to the cell.

9. The compound of claim 1, wherein $R^{14}$ is selected from the group consisting of $-(CH_2)_mR^9$, $-NH(CH_2)_mR^9$, $-NHC(O)(CH_2)_mR^9$, $-C(O)NH(CH_2)_mR^9$ and $-O(CH_2)_mR^9$.

10. The compound of claim 1, wherein $R^{14}$ is halide.

11. A method of inhibiting a deubiquitinase (Dub) comprising contacting the Dub with the compound of claim 1 or a pharmaceutically acceptable salt thereof in an amount sufficient to inhibit the Dub.

12. A method of inhibiting a pathogenic infection in a cell comprising contacting a pathogen or the cell with the compound of claim 1 or a pharmaceutically acceptable salt thereof in an amount sufficient to inhibit the pathogenic infection.

13. The method of claim 12, wherein the pathogenic infection is due to a condition selected from the group consisting of gastroenteritis, encephalitis, a respiratory tract infection, SARS, influenza, a virus-induced cancer, rabies, a hemorrhagic fever, Rift valley fever, listeriosis, and toxoplasmosis.

14. The method of claim 12, wherein the pathogen is a virus.

15. A composition comprising the compound of claim 1 and a pharmaceutically acceptable excipient.

16. The compound of claim 1, wherein X is fluoro.

17. The compound of claim 1, wherein X is chloro.

18. The compound of claim 1, wherein $R^1$ is selected from the group consisting of $-O(CH_2)_mNEt_2$; $-O(CH_2)_mNMe_2$; $-(CH_2)_mNHEt$; and $-O(CH_2)_mNHMe$.

19. The compound of claim 18, wherein $R^2$ is alkyl.
20. The compound of claim 18, wherein $R^{1A}$ is hydrogen.
21. The compound of claim 1, wherein $R^{1A}$ is hydrogen.
22. A method of inhibiting a deubiquitinase (Dub) comprising contacting the Dub with the compound of claim 5 or a pharmaceutically acceptable salt thereof in an amount sufficient to inhibit the Dub.

* * * * *

UNITED STATES PATENT AND TRADEMARK OFFICE
CERTIFICATE OF CORRECTION

PATENT NO.       : 8,809,377 B2  Page 1 of 1
APPLICATION NO.  : 13/241802
DATED            : August 19, 2014
INVENTOR(S)      : Nicholas J. Donato et al.

It is certified that error appears in the above-identified patent and that said Letters Patent is hereby corrected as shown below:

In the Claims:

At Column 78, line 67, "-$(CH_2)_m$NHEt;" should be -- -$O(CH_2)_m$NHEt; --.

Signed and Sealed this
Tenth Day of November, 2015

Michelle K. Lee
*Director of the United States Patent and Trademark Office*